(12) United States Patent
Yu

(10) Patent No.: US 10,836,757 B1
(45) Date of Patent: Nov. 17, 2020

(54) POLYMORPHIC FORMS OF METOPIMAZINE

(71) Applicant: Neurogastrx, Inc., Woburn, MA (US)

(72) Inventor: Shu Yu, Suzhou Industrial Park (CN)

(73) Assignee: NEUROGASTRX, INC., Woburn, MA (US)

( * ) Notice: Subject to any disclaimer, the term of this patent is extended or adjusted under 35 U.S.C. 154(b) by 0 days.

(21) Appl. No.: 16/838,402

(22) Filed: Apr. 2, 2020

Related U.S. Application Data

(60) Provisional application No. 63/003,998, filed on Apr. 2, 2020.

(51) Int. Cl.
*C07D 417/06* (2006.01)
*A61K 31/5415* (2006.01)

(52) U.S. Cl.
CPC ........ *C07D 417/06* (2013.01); *C07B 2200/13* (2013.01)

(58) Field of Classification Search
CPC .................... C07D 417/06; A61K 31/5415
See application file for complete search history.

(56) References Cited

U.S. PATENT DOCUMENTS

| | | | |
|---|---|---|---|
| 4,158,707 A | 6/1979 | Steffen et al. |
| 4,309,421 A | 1/1982 | Ghyczy et al. |
| 4,412,999 A | 11/1983 | Remy et al. |
| 4,439,196 A | 3/1984 | Higuchi |
| 4,447,224 A | 5/1984 | DeCant, Jr. et al. |
| 4,447,233 A | 5/1984 | Mayfield |
| 4,475,196 A | 10/1984 | La Zor |
| 4,486,194 A | 12/1984 | Ferrara |
| 4,487,603 A | 12/1984 | Harris |
| 4,710,570 A | 12/1987 | Thien |
| 4,925,678 A | 5/1990 | Ranney |
| 4,959,217 A | 9/1990 | Sanders et al. |
| 4,992,445 A | 2/1991 | Lawter et al. |
| 5,001,139 A | 3/1991 | Lawter et al. |
| 5,023,252 A | 6/1991 | Hseih |
| 5,164,386 A | 11/1992 | Cereda et al. |
| 5,164,405 A | 11/1992 | McFarlane et al. |
| 5,167,616 A | 12/1992 | Haak et al. |
| 5,169,383 A | 12/1992 | Gyory et al. |
| 5,225,182 A | 7/1993 | Sharma |
| 5,244,925 A | 9/1993 | Wretlind et al. |
| 5,246,935 A | 9/1993 | Jeppesen et al. |
| 5,434,174 A | 7/1995 | Gidda et al. |
| 5,674,205 A | 10/1997 | Pasricha et al. |
| 6,184,209 B1 | 2/2001 | Smith |
| 6,239,122 B1 | 5/2001 | Steele |
| 6,274,549 B1 | 8/2001 | Dyrberg et al. |
| 6,528,521 B2 | 3/2003 | Ruff et al. |
| 7,122,198 B1 | 10/2006 | Singh et al. |
| 7,358,271 B2 | 4/2008 | Barbeau |
| 7,615,207 B2 | 11/2009 | Lin |
| 7,930,033 B2 | 4/2011 | Chen et al. |
| 7,960,429 B2 | 6/2011 | Mangel |
| 8,095,218 B2 | 1/2012 | Gross et al. |
| 8,329,009 B2 | 12/2012 | Osipchuk et al. |
| 8,349,818 B2 | 1/2013 | DeLuca et al. |
| 9,132,134 B2 | 9/2015 | De Colle et al. |
| 9,808,467 B2 | 11/2017 | De Colle et al. |
| 9,844,554 B2 | 12/2017 | De Colle et al. |
| 2002/0164777 A1 | 11/2002 | Kelly et al. |
| 2003/0031707 A1 | 2/2003 | Rubin |
| 2003/0176421 A1 | 9/2003 | Watson et al. |
| 2005/0004155 A1 | 1/2005 | Boyd et al. |
| 2005/0203185 A1 | 9/2005 | Remenar et al. |
| 2006/0217391 A1 | 9/2006 | Landau |
| 2006/0258732 A1 | 11/2006 | Dinan et al. |
| 2006/0287221 A1 | 12/2006 | Knudsen et al. |
| 2007/0129307 A1 | 6/2007 | Tan et al. |
| 2009/0042871 A1 | 2/2009 | Coats et al. |
| 2009/0054319 A1 | 2/2009 | Talley et al. |
| 2009/0253634 A1 | 10/2009 | Currie et al. |
| 2009/0326004 A1 | 12/2009 | Kumar et al. |
| 2011/0282411 A1 | 11/2011 | Knudson et al. |
| 2011/0319343 A1 | 12/2011 | Shailubhai |
| 2012/0010228 A1 | 1/2012 | Luehr et al. |
| 2012/0053121 A1 | 3/2012 | Besner et al. |
| 2012/0077745 A1 | 3/2012 | Polvino |
| 2012/0101089 A1 | 4/2012 | Agarwal et al. |
| 2012/0115910 A1 | 5/2012 | Seeman |
| 2012/0164139 A1 | 6/2012 | Pasricha et al. |
| 2012/0283411 A9 | 11/2012 | Currie et al. |
| 2018/0200258 A1 | 7/2018 | De Colle et al. |
| 2019/0314384 A1 | 10/2019 | De Colle et al. |

FOREIGN PATENT DOCUMENTS

| | | |
|---|---|---|
| CN | 102548555 A | 7/2012 |
| DE | 2235998 A1 | 2/1973 |
| EP | 2581085 A1 | 4/2013 |
| FR | 2845914 A | 4/2004 |
| IN | 360/CHE/2010 | 8/2011 |

(Continued)

OTHER PUBLICATIONS

U.S. Appl. No. 16/862,762, filed Apr. 30, 2020, De Colle et al.
Abell, et al. "Treatment of gastroparesis: a multidisciplinary clinical review," Neurogastroenterol Motil., 2006, 18, 263-283.
Acosta, et al. "Prokinetics in gastroparesis," Gastroenterol Clin North Am. Mar. 2015;44(I):97-111. doi: 10.1016/j.gtc.2014.11.008. Epub Dec. 23, 2014.
Agrawal, et al., "University of Miami Division of Clinical Pharmacology Therapeutic Rounds: Update on Diagnosis and Treatment of Gastroparesis," American Journal of Therapeutics, Lippincott Williams & Wilkins, US, vol. 6, No. 2: 97-109, Mar. 1, 1999.
Angelo, et al., "High-performance liquid chromatographic method with fluorescence detection for the simultaneous determination of metopimazine and its acid metabolite in serum," J Chromatogr. Nov. 24, 1989;496(2):472-7.
Arbus, et al., "Use of metopimazine in certain vomitings from central origin," Therapeutique. May 1971;47(5):469-71.

(Continued)

*Primary Examiner* — Bruck Kifle
(74) *Attorney, Agent, or Firm* — White & Case LLP

(57) ABSTRACT

Provided herein are novel polymorphic forms of metopimazine mesylate. These polymorphic forms are useful in methods, compositions, and kits for the treatment of an enteric nervous system disorder.

24 Claims, 5 Drawing Sheets

(56) References Cited

FOREIGN PATENT DOCUMENTS

| | | |
|---|---|---|
| IN | 2528/MUM/2013 | 6/2015 |
| WO | WO-2004082667 A1 | 9/2004 |
| WO | WO-2008134540 A1 | 11/2008 |
| WO | WO-2011107653 A1 | 9/2011 |
| WO | WO-2013028909 A1 | 2/2013 |

OTHER PUBLICATIONS

Arnaud, et al., "Value of metopimazine (Vogalene) in the prevention and treatment of postoperative vomiting in ocular surgery. (Apropos of 100 cases)," Arch Ophtalmol Rev Gen Ophtalmol. Jan. 1972;32(I):63-8.

Babar, I. et al., "Gastroparesis Patient Treatment Survey, Survey 17-190," GuidePoint, pp. 1-18, May 26, 2017.

Badji, et al., "Comparative study of the effects of metoclopramide and metopimazine on the duodenojejunal motility during the interdigestive period: a manometric study in healthy subjects," Ann Gastroenterol Hepatol (Paris). Dec. 1988;24(7):369-74. [with Certified English Translation].

Ballestar, et al., "Clinical study of metopimazine in gastroenterology," Rev Esp Enferm Apar Dig. Jul. 1980;58(I):41-6. (with Machine Translation of Introduction).

Barale, et al., "Comparative study of the intestinal spasmolytic properties of metoclopramide and metopimazine," Anesth Analg (Paris). Jan.-Feb. 1977;34(I):47-54.

Berga, et al., "Comparison of clebopride, domperidone, metopimazine, and trimebutine as antiemetics and inducers of gastrointestinal peristalsis," Arch Farmacol Toxicol. Apr. 1981;7(I): 189-92. (with Machine Translation).

Berry, et al., "The prevention of radiation sickness. Report of a double blind random clinical trial using prochlorperazine and metopimazine," Clin Radiol. Oct. 1971;22(4):534-7.

Bertrand, et al., "Action of metopimazine on gastric motility. Double-blind study using external digestive electromyography," Nouv Presse Med. Oct. 4, 1975;4(32):2319-20. [with Certified English Translation].

Bethune-Volters, et al., "A randomized, double-blind trial assessing the efficacy and safety of sublingual metopimazine and ondansetron in the prophylaxis of chemotherapy-induced delayed emesis", Anti-Cancer Drugs, vol. 12(2): 217-224 (2006).

Blanes, et al., "Comparative study "in vitro" of transdermal absorption of a series of antiemetic drugs," Eur J Drug Metab Pharmacokinet. 1991;Spec No. 3:410-4.

Bloch, et al., "Comparison of the efficacy and safety of combinations of metopimazine or ondansetron with methylprednisolone in the prevention of delayed emesis in patients receiving chemotherapy," Curr Med Res Opin. Nov. 2005;21(I 1): 1763-71.

Bounoure, et al., "Effect of iontophoresis and penetration enhancers on transdermal absorption of metopimazine," J Dermatol Sci. Dec. 2008;52(3): 170-7. doi:10.1016/j.jdermsci.2008.06.009. Epub Aug. 3, 2008.

Camilleri, et al., "Clinical guideline: management of gastroparesis," Am J Gastroenterol. Jan. 2013;108(I):18-37; quiz 38. doi: 10.1038/ajg.2012.373. Epub Nov. 13, 2012.

Camilleri, "Clinical practice. Diabetic gastroparesis," N Engl J Med. Feb. 22, 2007;356(8):820-9.

Calpena, et al., "A comparative in vitro study of transdermal absorption of antiemetics," J Pharm Sci. Jan. 1994;83(I):29-33.

Casanova, et al., "A comparative study of alizapride and metopimazine," (author's transl). Sem Hop. Feb. 1982 II;58(6):345-8.

Champion, "Management of idiopathic, diabetic and miscellaneous gastroparesis with cisapride," Scand J Gastroenterol Suppl. 165: 44-52; discussion 52-3 1989 abstract only.

Chu, et al., "A controlled clinical study of metopimazine and perphenazine in treatment of radiation nausea and vomiting," Clin Pharmacol Ther. Nov.-Dec. 1969;10(6):800-9.

Clavel, et al., "Improved control of emesis and quality of life with ondansetron in breast cancer," Oncology. May-Jun. 1993;50(3): 180-5.

Cournot, et al., "Antiemetic effect of metopimazine measured by the apomorphine test," Mar.-Apr. 1987;42(2): 183-6. (with English abstract).

Croom, et al., "Metopimazine a review of its use in the treatment of chemotherapy-induced nausea and vomiting," Am. J. Cancer. 2006; 5(2): 123-136.

Davis, et al., "A Systematic Review of the Treatment of Nausea and/or Vomiting in Cancer Unrelated to Chemotherapy or Radiation," vol. 39, No. 4. pp. 756-767 (2010).

Debray, et al., "Treatment of vomiting in infants and children induced by acute infectious pathology," A comparative study of alizapride versus metopimazine. Dec. 1990;37(10):683-7.

Des Varannes. Comments on the use of metopimazine in France. Attn. C. De Colle. Neurogastrx Inc. Jun. 16, 2015.

Diaz, et al., "The [$^3$H]dofetilide binding assay is a predictive screening tool for hERG blockade and proarrhythmia: Comparison of intact cell and membrane preparations and effects of altering [$K^+$]$_o$, " J Pharmacol Toxicol Methods. Nov.-Dec. 2004;50(3): 187-99.

Djeddi, et al., "Effect of Domperidone on QT Interval in Neonates," The Journal of Pediatrics. 2008: 153(5):663-666.

Dorval, et al., "Dyspepsia: modern concept and therapeutic approaches," Gastro-Enterology, Jan. 14, 1989; 111(2):105-109 [with Certified English Translation].

Dupuis, et al., "Optimizing emetic control in children receiving antineoplastic therapy: beyond the guidelines," Pediatric Drugs. 2010; 12(1):51-61. doi: 10.2165/11316190-000000000-00000. Review.

Dupuis, et al., "Options for the prevention and management of acute chemo therapy—induced nausea and vomiting in children," Pediatric Drugs. 2003;5(9):597-613. Review.

Ellebaek, et al., "Optimizing antiemetic therapy in multiple-day and multiple cycles of chemotherapy," Curr Opin Support Palliat Care. Mar. 2008;2(I):28-34. doi: 10.1097/SPC.0b013e3282f44a75.

European search report and opinion dated May 13, 2016 for EP application No. 13869541.

Fedorak, et al., "A novel colon-specific steroid prodrug enhances sodium chloride absorption in rat colitis," Am J Physiol. Aug. 1995;269(2 Pt I):G210-8.

Fieni, et al., "Clinical protocol for pregnancy termination in bitches using prostaglandin F2 alpha," J Reprod Fertil Suppl. 1997;51:245-50.

Frédéric, et al., "Percutaneous absorption of metopimazine and effect of cyclodextrins," Drug Dev Ind Pharm. May 2008;34(5):478-84. doi: 10.1080/03639040701743873.

Furness, "The enteric nervous system and neurogastroenterology," Nature Reviews Gastroenterology and Hepatol. 2012; 9:286-294.

Gaillot, et al., "Metabolic behavior of methopimazine as a function of route of administration. Impact of the first-pass effect on systemic bioavailability," Farmaco Prat. Jan. 1980;35(I):3-22.

Gazy, et al., "Differential pulse cathodic voltammetric determination of floctafenine and metopimazine," J Pharm Biomed Anal. Mar. 12, 2007;43(4): 1535-9. Epub Dec. 11, 2006.

Ghoos, et al., "Measurement of gastric emptying rate of solids by means of a carbon-labeled octanoic acid breath test," Gastroenterology. Jun. 1993;104(6):1640-7.

Gosselin, et al., "Manometric effects of metopimazine on the lower esophageal sphincter," (author's transl.). Sem Hop. Feb. 8-15, 1981;57(5-6):291-5. English abstract.

Guerin, et al., "Therapeutic value of metopimazine as an antiemetic in cancerology," Presse Med. May 17, 1969;77(24):893.

Hansen, "The enteric nervous system III: a target for pharmacological treatment," Pharmacol Toxicol. Jul. 2003;93(I): 1-13.

Harer, et al., "Chronic Unexplained Nausea and Vomiting or Gastric Neuromuscular Dysfunction (GND)? An Update on Nomenclature, Pathophysiology and Treatment, and Relationship to Gastroparesis," Current Treatment Options Gastroenterology. DO1 10.1007/s11938-016-0113-z, 12 pages, Oct. 8, 2016.

Hasler, "Symptomatic management for gastroparesis. Antiemetics, analgesics, and symptom modulators," Gastroenterol. Clin. N. Am. 2015; 44:113-126.

(56) References Cited

OTHER PUBLICATIONS

Herrstedt, et al., "Treatment of chemotherapy-induced nausea and vomiting," Ugeskr Laeger, Jan. 24, 1994, 156(4):453-460 Review. Danish with English summary on p. 459.

Herrstedt, et al., "Bioavailability of the antiemetic metopimazine given as a microenema," Br J Clin Pharmacol. Jun. 1996;41(6):613-5.

Herrstedt, et al., "Dose-finding study of oral metopimazine," Support Care Cancer. Jan. 1997;5(I):38-43.

Herrstedt, et al., "Interaction of the antiemetic metopimazine and anticancer agents with brain dopamine $D_2$, 5-hydroxytryptamine$_3$, histamine $H_1$, muscarine cholinergic and alpha$_1$-adrenergic receptors," Cancer Chemotherapy Pharmacology. 1993;33(I):53-6.

Herrstedt, et al., "Ondansetron plus metopimazine compared with ondansetron alone in patients receiving moderately emetogenic chemotherapy," N Engl J Med. Apr. 15, 1993;328(15):1076-80.

Herrstedt, et al., "Randomized, double-blind comparison of ondansetron versus ondansetron plus metopimazine as antiemetic prophylaxis during platinum-based chemotherapy in patients with cancer," J Clin Oncol. Apr. 1997; 15(4): 1690-6.

Herrstedt, et al., "Randomized, double-blind trial comparing the antiemetic effect of tropisetron plus metopimazine with tropisetron plus placebo in patients receiving multiple cycles of multiple-day cisplatin-based chemotherapy," Support Care Cancer. Apr. 2007;15(4):417-26. Epub Nov. 9, 2006.

Herrstedt, et al., "The effect of food on serum concentrations of metopimazine," Br J Clin Pharmacol. Aug. 1990;30(2):237-43.

Herrstedt, J. "Chemotherapy-induced nausea and vomiting with special emphasis on metopimazine," Dan Med Bull. Sep. 1998;45(4):412-22. Review.

Herrstedt, J. "Development of antiemetic therapy in cancer patients," Acta Oncol. 1995;34(5):637-40. Review.

Hershcovici, "Pharmacological management of GERD: where does it stand now?," Trends Pharmacol Sci. Apr. 2011;32(4):258-64.

Higuchi, et al., "Pro-drugs as novel drug delivery systems," American Chemical Society. ACS symposium series 14. 1975.

Hiyama, Toru et al., "Treatment of functional dyspepsia with serotonin agonists: A meta-analysis of randomized controlled trials," Journal of Gastroenterology and Hepatology, 22; 1566-1570 (2007).

Hochhaus, et al., "A selective HPLC/RIA for dexamethasone and its prodrug dexamethasone-21-sulphobenzoate sodium in biological fluids," Biomedical Chromatography. Nov.-Dec. 1992;6(6):283-6.

Hondeghem, "Domperidone: Limited Benefits With Significant Risk for Sudden Cardiac Death," Journal of Cardiovascular Pharmacology. 2013; 61(3):218-225.

Hubert-Roux, et al., "Fragmentation pathways of metopimazine and its metabolite using ESI-MS(n), HR-MS and H/D exchange," J Mass Spectrom. Oct. 2010;45(10): pp. 1121-1129. doi: 10.1002/jms.I790.

Huttunen, et al., "Pro-drugs—from serendipity to rational design," Pharmacol Rev. Sep. 2011; 63(3): pp. 750-771. doi: 10.1124/pr.110.003459. Epub Jul. 7, 2011.

International search report and written opinion dated May 21, 2014 for PCT/US2013/076733.

International Application No. PCT/US2015/037258 International Preliminary Report on Patentability dated Dec. 27, 2016.

Israel, et al., "Treatment of nausea and vomiting related to anticancerous multiple combination chemotherapy: results of two controlled studies," J Int Med Res. 1978;6(3):235-40.

Jadot, et al., "Comparative statistical study of two antiemetics, metoclopramide and metopimazine, effects on the oestrus cycle in the female rat," (author's transl). Pathol Biol (Paris). Jan. 1980;28(I):68-72. French with English Summary.

Janssen, et al., "The Relation Between Symptom Improvement and Gastric Emptying in the Treatment of Diabetic and Idiopathic Gastroparesis," The American Journal of Gastroenterology, vol. 108, Sep. 2013, pp. 1382-1391.

Jolliet, et al., "Evidence of lowest brain penetration of an antiemetic drug, metopimazine, compared to domperidone, metoclopramide and chlorpromazine, using an in vitro model of the blood-brain barrier," Pharmacol Res. Jul. 2007;56(1): pp. 11-17. Epub Dec. 19, 2006.

Khamales, et al., "A randomized, double-blind trial assessing the efficacy and safety of sublingual metopimazine and ondansetron in the prophylaxis of chemotherapy-induced delayed emesis," Anticancer Drugs. Feb. 2006;17(2):217-24. Erratum in: Anticancer Drugs. Jun. 2006;17(5):599.

Kilgore, et al., "Investigational use of metomidate hydrochloride as a shipping additive for two ornamental fishes," J Aquat Anim Health. Sep. 2009;21(3):133-9. doi: 10.1577/H08-030.1.

Knowles, et al., "New perspectives in the diagnosis and management of enteric neuropathies," Nature Reviews Gastroenterology and Hepatology. 2013; 10:206-218.

Larsen, et al., "Prodrug forms for the sulfonamide group. I. Evaluation of N-acyl derivatives, N-sulfonylamidines, N-sulfonylsulfilimines and sulfonylureas as possible prodrug derivatives," Int. J. Pharm. 1987; 37:87-95.

Larsen, et al., "Prodrug forms for the sulfonamide group. II. Water-soluble amino acid derivatives of N-methylsulfonamides as possible prodrugs," Int. J. Pharm. 1988; 47:103-110.

Laverdant, et al., "Functional manifestations of irritable bowel. Treatment by metopimazine. Manifestations fonctionnelles du colon irritable. Traiment para la metopimazine," Lyon Medical. Jan. 1, 1981; 245(4):183-185 (in French with English abstract).

Lebeau, et al., "The efficacy of a combination of ondansetron, methylprednisolone and metopimazine in patients previously uncontrolled with a dual antiemetic treatment in cisplatin-based chemotherapy," The French Ondansetron Study Group. Ann Oncol. Sep. 1997;8(9):887-92.

Li, et al., "Physiological modulation of intestinal motility by enteric dopaminergic neurons and the D2 receptor: analysis of dopamine receptor expression, location, development, and function in wild-type and knock-out mice," J Neurosci. Mar. 8, 2006;26(10):2798-807.

Llau, et al., "Drug-induced parkinsonian syndromes: a 10-year experience at a regional center of pharmaco-vigilance," Rev Neurol (Paris). Nov. 1994;150(11):757-62.

Mallet, et al., "Pharmacokinetic study of metopimazine by oral route in children," Pharmacology Research and Perspectives, vol. 3, Issue 3, pp. 1-7, 2015.

Mcleod, et al., "A glucocorticoid prodrug facilitates normal mucosal function in rat colitis without adrenal suppression," Gastroenterology. Feb. 1994;106(2):405-13.

Metopimazine Label—Summary of Product Characteristics, dated Aug. 16, 2011 (agence-prd.ansm.sante.fr/php/ecodex/frames.php?specid=68318931&typedoc=R&ref=R0195277.htm )(5 pages) [with Certified English Translation].

Merck. The Merck Index. Eleventh Ed. 1989. Monograph 4116 Fluphenazine. 655-656.

Monges, et al., "Clinical study of oral solution of Vogalene (metopimazine)," Etude clinique du solute buvable de Vogalene. Mediterranee Medicale. Jan. 1, 1975; 3(66):81-82 (in French with English machine translation).

Moertel, et al., "Controlled studies of metopimazine for the treatment of nausea and vomiting," J Clin Pharmacol. Jul. 1973;13(7):283-7.

Mozaffari, Shilan et al., "Metabolic and toxicological considerations for the latest drugs used to treat irritable bowel syndrome," Expert Opinion on Drug Metabolism & Toxicology, 9(4): 403-421 (2013).

Naguib, et al., "Development and validation of stability indicating HPLC and HPTLC methods for determination of sulpiride and mebeverine hydrochloride in combination," Eur JMedChem. Sep. 2010;45(9):3719-25. doi: 10.1016/j.ejmech.2010.05.021. Epub May 15, 2010.

Naguib, et al., "Stability indicating HPTLC method for determination of Metopimazine in pharmaceutical formulation and human plasma," Ben-Sue University Journal of Basic and Applied Science: 52-62 (2014).

Nathan, et al., "A pilot study of ondansetron plus metopimazine vs. ondansetron monotherapy in children receiving highly emetogenic

(56) References Cited

OTHER PUBLICATIONS chemotherapy: a Bayesian randomized serial N-of-1 trials design," Support Care Cancer. Mar. 2006;14(3):268-76. Epub Jul. 29, 2005.
Niemegeers, CJ., "Antiemetic specificity of dopamine antagonists," Psychopharmacology (Berl). 1982;78(3):210-3.
Nippon Naika Gakkai Zasshi, "Methods for Treating GI Tract Disorders," The Journal of the Japanese Society of Internal Medicine, vol. 2, pp. 122-127 (2006) [with Certified English Translation].
Norcliffe-Kaufmann, et al., "Hyperdopaminergic crises in familial dysautonomia: A randomized trial of carbidopa," Neurology. Apr. 23, 2013;80(17):1611-7. doi: 10.1212/WNL.0b013e31828fl8f0. Epub Apr. 3, 2013.
Obermayr, et al., "Development and developmental disorders of the enteric nervous system," Nature Reviews Gastroenterology and Hepatology. 2013; 10:43-57.
Ontario Health Technology Assessment Series, vol. 6, No. 16, p. 10 (2006).
Palfreyman, et al., "α-difluoromethyl DOPA, a new enzyme-activated irreversible inhibitor of aromatic L-amino acid decarboxylase," J Neurochem. Oct. 1978;31(4):927-32.
Paradis, et al., "A new antiemetic: The Vogalene (metopimazine or 9965 RP)," Laval Med. Dec. 1967;38(10):901-7. (machine translation).
Parkman, et al., "Gastroparesis and Functional Dyspepsia: Excerpts from the AGA/ANMS Meeting," Neurogastroenterol. Motil, Feb. 2010, 22(2): 113-133. doi:10.1111/j.1365-2982.2009.01434.x.
Parkman, et al, "Domperidone Treatment for Gastroparesis: Demographic and Pharmacogenetic Characterization of Clinical Efficacy and Side-Effects," Digestive Diseases and Sciences, Kluwer Academic Publishers-Plenum Publishers, NE, vol. 56, No. 1, pp. 115-124, Nov. 10, 2010.
Parkman, et al., "American Gastroenterological Association technical review on the diagnosis and treatment of gastroparesis," Gastroenterology. Nov. 2004; 127(5): 1592-622.
Parkman, et al., "Effect of nortriptyline on symptoms of idiopathic gastroparesis: the NORIG randomized clinical trial," JAMA. Dec. 25, 2013;310(24):2640-9. doi: 10.1001/jama.2013.282833.
Parrish, et al., "Nutrition Intervention for the Patient with Gastroparesis: An Update," Practical Gastroenterology. Aug. 2005; 29-66.
Pasricha, et al., "Toward a Better Drug for Gastroparesis: The Problem with a Moving Target," Gastroenterology, 2016, vol. 151, Issue 1, pp. 20-22.
Payne, et al., "Mechanisms of ligand binding and efficacy at the human D2(short) dopamine receptor," J Neurochem. Sep. 2002;82(5): 1106-17.
Pimentel, M. et al., "Low-Dose Nocturnal Tegaserod or Erythromycin Delays Symptom Recurrence After Treatment of Irritable Bowel Syndrome Based on presumed Bacterial Overgrowth," Gastroenterology & Hepatology 5(6);435-442 (Jun. 2009).
Priest, et al., "Role of hERG potassium channel assays in drug development," Channels (Austin). Mar.-Apr. 2008;2(2):87-93. Epub Mar. 5, 2008.
Quigley, Eamonn, "Prokinetics in the Management of Functional Gastrointestinal Disorders," Journal of Neurogastroenterology and Motility, 21(3); 330-336 (Jul. 2015).
Ray, K., "Motility: Mapping gastric dysrhythmias in gastroparesis—a slow wave of electrical activity," Nature Reviews Gastroenterology and Hepatology. 2012; 9:363.
Reddymasu, et al., "Pharmacotherapy of gastroparesis," Expert Opin Pharmacother. Feb. 2009;10(3):469-84.
Regina, et al., "Clinical tolerance of a new antidepressant—Milnacipran. L'Encephale". May-Jun. 1999;25(3):252-8. (English Abstract).
Rodary, et al., "Double blind randomized trial of metopimazine: for postoperative nausea and vomiting after cholecystectomy," Ann Anesthesiol Fr. 1979;20(2): 118-20.
Roila, et al., "Antiemetic effects of ondansetron and metopimazine," N Engl J Med. Oct. 28, 1993;329(18): 1356-7.
Sanguinetti, et al., "hERG potassium channels and cardiac arrhythmia," Nature. Mar. 23, 2006;440(7083):463-9.
Saphir, A., "Fighting nausea in the '90s: more and better antiemetics can help," J Natl Cancer Inst. Sep. 3, 1997;89(17):1252-5.
Seigneuric, et al., "Extrapyramidal syndrome. Possible role of metopimazine," Presse Med. Apr. 2, 1983;12(15):962-3.
Sigsgaard, et al., "Antiemetic efficacy of combination therapy with granisetron plus prednisolone plus the dopamine D2 antagonist metopimazine during multiple cycles of moderately emetogenic chemotherapy in patients refractory to previous antiemetic therapy," Support Care Cancer. May 2000;8(3):233-7.
Sigsgaard, et al., "Ondansetron plus metopimazine compared with ondansetron plus metopimazine plus prednisolone as antiemetic prophylaxis in patients receiving multiple cycles of moderately emetogenic chemotherapy," J Clin Oncol. Apr. 1, 2001; 19(7):2091-7.
Sigsgaard, et al., "Granisetron compared with prednisolone plus metopimazine as anti-emetic prophylaxis during multiple cycles of moderately emetogenic chemotherapy," Br J Cancer. May 1999;80(3-4):412-8.
Simmons, et al., "Granisetron transdermal system improves refractory nausea and vomiting in gastroparesis," Dig Dis Sci. Jun. 2014;59(6):1231-4. doi: 10.1007/s 10620-014-3097-3. Epub Mar. 11, 2014.
Sindelar, et al., "Modified Syntheses of 2-(Methylthio)-10-(2-(1-Methyl-2-Piperdinyl)Ethyl)Phenothiazine (Thioridazine) and 1-(3-(2-(Methylsulfonyl)-10-Phenothiazinyl)Propyl)-Piperidine-4-Carboxamide (Metopimazine)," Collect. Czech Chem Commun., vol. 55, pp. 1586-1601, 1990.
Sinkula, et al., "Rationale for design of biologically reversible drug derivatives: prodrugs," J Pharm Sci. Feb. 1975;64(2):181-210.
Stern, et al., "Electrogastrography: current issues in validation and methodology," Psychophysiology. Jan. 1987;24(I):55-64.
Stroyer, et al., "Clinical evaluation of an antiemetic, metopimazine (Vogalene) in an open and double-blind trial," Ugeskr Laeger. Jul. 12, 1976;138(29):1769-70. Danish with English Summary on p. 1770.
Thomforde, et al., "Evaluation of an inexpensive screening scintigraphic test of gastric emptying," JNucl Med. Jan. 1995;36(I):93-6.
Tonini, et al., "Effects of metopimazine on gastro-intestinal and biliary tract smooth muscle in vitro," Arch Int Pharmacodyn Ther. Jan. 1980;243(I): 139-148.
Tonini, et al., "Effects of metopimazine on motility of the gastrointestinal tract," Farmaco Prat. Oct. 1980;35(10):516-23.
Valeyre, et al., "Tolerance and efficacy of mefloquine as the first line treatment of uncomplicated P. falciparum malaria in children," Pathol Biol (Paris). Feb. 2008;56(I):21-8. doi: 10.1016/j.patbio. 2007.09.003. Epub Jan. 4, 2008. French.
Vallejo, et al., "Toxicity and dose response of intravenous (i.v.) metopimazine (MPZ) as preventive of high-dose cisplatin (CDDP)-induced emesis," Proc Am Soc Clin Oncol. 1988; 7:286.
Viala, et al., "A double-blind study of alizapride in nausea and emesis induced by cancer chemotherapeutic agents," (author's transl.). Sem Hop. Feb. 11, 1982 ;58(6):371-4.
Uezono, et al, "Gastrointestinal Motility Control Receptors Expressed in the Enteric Plexus and Gastrointestinal Function Improving Agents Targeting Such Receptors", Journal of Clinical and Experimental Medicine vol. 238 No. 10, pp. 904-908 Sep. 3, 2011 [with English Certification].

POLYMORPHIC FORMS OF METOPIMAZINE

RELATED APPLICATION

This application claims the benefit of priority to U.S. Provisional Patent Application No. 63/003,998, filed Apr. 2, 2020, which application is hereby incorporated by reference in its entirety.

BACKGROUND

The enteric nervous system (ENS) comprises about one hundred million neurons embedded in the lining of the gastrointestinal system. The ENS innervates the gastrointestinal system, including the esophagus, the stomach (e.g., gastric area), and the intestines. Motor neurons of the ENS control stomach muscle contractility, peristalsis, and churning of intestinal contents. It has been estimated that about 50% of the body's dopamine is found in the ENS.

Gastrointestinal (GI) tract disorders affect many people. Irritable bowel syndrome (IBS), a disorder in which the intestine functions abnormally due to dysfunction of the muscles or nerves of the GI tract, affects 10 to 15% of the adult population. Symptoms of IBS include constipation, diarrhea, and abdominal pain. Functional dyspepsia (dyspepsia caused by a dysfunction of the muscles or nerves associated with the upper GI tract) affects 10 to 20% of the adult population. Gastroparesis, a disorder causing inadequate grinding of food by the stomach and delayed gastric emptying, affects up to 10% of the general population. Gastroesophageal reflux disorder (GERD), a chronic digestive disease that occurs when stomach acid and/or bile backs up into the esophagus, has been estimated to affect up to 35% of infants in the first few months of life and more than half of the general population in the US.

In addition, gastrointestinal disorders can be associated with a number of other diseases. For example, some of the earliest symptoms of Parkinson's disease, a disorder characterized by neurodegeneration of dopamine neurons, include, e.g., constipation and other gastrointestinal symptoms, likely due to degeneration or dysfunction of ENS dopamine neurons. Another example is diabetes, one of the most common causes of gastroparesis, as chronic high blood sugar can damage the vagus nerve which modulates the enteric nervous system. Multiple sclerosis is another disease that is associated with ENS disorders such as, e.g., gastroparesis. Migraine headaches are commonly associated with gastric stasis. Chemotherapy-induced nausea and/or vomiting have been estimated to affect 85% of cancer patients undergoing chemotherapy and can result in discontinuation of treatment. If the chemotherapy-induced nausea and/or vomiting are not properly managed, it can cause dehydration and poor quality of life and may result in discontinuation of chemotherapy.

ENS dysfunction has been implicated in several of the disorders described above. For example, impaired or dysfunctional ENS neuronal signaling has been strongly implicated as a causative factor for gastroparesis.

There are currently no adequate treatments for these disorders. For example, IBS treatments lubiprostone and linaclotide are used to mimic infectious diarrhea in order to treat constipation; however, these agents do not correct the underlying ENS dysfunction and are marginally effective. The dopamine $D_2$ receptor antagonists domperidone and metoclopramide have been previously indicated for the treatment of nausea and vomiting, however, their use is discouraged due to significant safety issues, in particular for extended periods of time. Two significant safety concerns relate to (1) unwanted cardiac side effects caused by, e.g., interaction of the agents with ion channels involved in cardiac action potentials, and (2) unwanted motor dysfunction caused by the actions of the dopamine antagonists which cross the blood brain barrier into the brain. For example, it has been established that many dopamine receptor antagonists inhibit hERG channels (a type of potassium channel) to cause drug-induced long QT syndrome, a heart condition characterized by abnormal cardiac action potential rhythms. Long QT syndrome can increase risk of cardiac arrhythmias, which may lead to sudden cardiac death. Indeed, the dopamine $D_2$ antagonist domperidone has been shown to inhibit hERG activity and increase risk of long QT syndrome, and increase risk of sudden cardiac death. This has resulted in an FDA ban on the use of domperidone in the United States and an initiated review of the safety of domperidone use by the European Medicines Agency. Metoclopramide cannot be taken for more than 12 weeks and has a black box warning for CNS-related side effects such as tardive dyskinesia, a difficult-to-treat and often incurable disorder characterized by involuntary, repetitive body movements.

SUMMARY OF THE APPLICATION

The present application provides a crystalline form of metopimazine mesylate. In certain embodiments, the crystalline form comprises less than 10 wt. % of amorphous forms. In certain embodiments, the crystalline form is in non-solvate form. In certain such embodiments, the crystalline form comprises less than 10 wt. % of solvate forms. In certain embodiments of the foregoing, the present application provides a crystalline form of metopimazine mesylate wherein the crystalline form comprises metopimazine mesylate Crystal Form A.

The present application provides a crystalline form of metopimazine mesylate characterized by an X-ray powder diffraction pattern comprising a peak at the following 2θ value: 18.75°. In certain embodiments, the crystalline form of metopimazine mesylate is characterized by an X-ray powder diffraction pattern comprising a peak at the following 2θ value: 15.91° and 18.75°. In certain embodiments, the crystalline form of metopimazine mesylate is characterized by an X-ray powder diffraction pattern comprising a peak at the following 2θ value: 15.91°, 18.75°, and 24.44°.

The present application provides a crystalline form of metopimazine mesylate characterized by an X-ray powder diffraction pattern comprising one or more of the following 2θ values: 9.37°, 15.26°, 15.91°, 18.75°, 19.09°, 20.80°, 21.22°, 21.77°, and 24.44°. In certain embodiments, the crystalline form is characterized by an X-ray powder diffraction pattern comprising two or more of the following 2θ values: 9.37°, 15.26°, 15.91°, 18.75°, 19.09°, 20.80°, 21.22°, 21.77°, and 24.44°. In certain embodiments, the crystalline form is characterized by an X-ray powder diffraction pattern comprising three or more of the following 2θ values: 9.37°, 15.26°, 15.91°, 18.75°, 19.09°, 20.80°, 21.22°, 21.77°, and 24.44°.

The present application provides a crystalline form of metopimazine mesylate characterized by a differential scanning calorimetry pattern comprising a single endotherm comprising an onset temperature range of 208° C. to 212° C. In certain embodiments, the single endotherm comprises an onset temperature range of 208° C. to 211° C. In certain embodiments, the single endotherm comprises an onset temperature range of 209° C. to 210° C. In certain embodiments of any of the foregoing, the single endotherm comprises a peak temperature range of 213° C. to 214° C. In certain embodiments of any of the foregoing, the single endotherm comprises an enthalpy of transition of 95-100 J/g. In certain such embodiments, the single endotherm comprises an enthalpy of transition of 96-98 J/g. In further embodiments, the single endotherm comprises an enthalpy of transition of 97-98 J/g.

The present application provides a crystalline form of metopimazine mesylate characterized by a thermogravimetric analysis profile comprising a total weight loss of 0.4% up to 150.0° C.

In certain embodiments of any of the foregoing, the composition comprises less than 10 wt. % of other crystalline forms. In certain such embodiments, the composition comprises less than 1 wt. % of other crystalline forms. In certain embodiments of the foregoing, the composition comprises less than 10 wt. % of amorphous forms. In certain such embodiments, the composition comprises less than 1 wt. % of amorphous forms.

The present application provides a pharmaceutical composition comprising any of the foregoing crystalline forms and a pharmaceutically acceptable excipient. In certain embodiments, the pharmaceutical composition is suitable for administering orally, intraduodenally, intracolonically, enterally, topically, intranasally, non-orally, buccally, sublingually, by inhalation, or rectally. In certain embodiments, the composition is suitable for administering orally. In certain embodiments, the composition is suitable for administering sublingually. In certain embodiments of the foregoing, the pharmaceutical composition is formulated as a tablet, a capsule, an oil, a gel, a paste, a powder, a suspension, a syrup, an enema, a suppository, an emulsion, or a solution, an extended-release formulation, or a modified-release formulation. In certain such embodiments, the composition is formulated as an extended release formulation. In further embodiments, the composition is formulated as a capsule.

In certain embodiments of any of the foregoing pharmaceutical compositions, the composition comprises 5 mg of the crystalline form of metopimazine mesylate. In certain embodiments, the composition comprises 10 mg of the crystalline form of metopimazine mesylate. In certain embodiments, the composition comprises 15 mg of the crystalline form of metopimazine mesylate. In certain embodiments, the composition comprises 20 mg of the crystalline form of metopimazine mesylate.

In certain embodiments of any of the foregoing pharmaceutical compositions, the composition is suitable for administration one time per day. In certain embodiments, the composition is suitable for administration two times per day. In certain embodiments, the composition is suitable for administration three times per day. In certain embodiments, the composition is suitable for administration four times per day.

In certain embodiments of any of the foregoing pharmaceutical compositions, between about 5 mg and about 160 mg of the crystalline form of metopimazine mesylate is administered per day. In certain embodiments, the composition is suitable for administration of more than 20 mg of the crystalline form of metopimazine mesylate per day.

The present application provides a method of treating an enteric nervous system disorder in a human subject in need thereof, comprising administering to the subject any of the foregoing pharmaceutical compositions. In certain embodiments, the enteric nervous system disorder is a chronic disorder. In other embodiments, the enteric nervous system disorder is an acute disorder. In certain embodiments, the enteric nervous system disorder is selected from the group consisting of gastroparesis, Irritable Bowel Syndrome, lysosomal storage disorders, intestinal dysmotility, ganglioneuroma, multiple endocrine neoplasia type 2B (MEN2B), gastrointestinal neuropathy, functional dyspepsia, gastroesophageal reflux disease (GERD), and intestinal neuronal dysplasia. In certain embodiments of the foregoing, the enteric nervous system disorder comprises a symptom selected from the group consisting of early satiety, postprandial fullness, abdominal fullness, nausea, vomiting, delayed gastric emptying, diarrhea, abdominal pain, gas, bloating, gastroesophageal reflux, reduced appetite, and constipation. In certain embodiments, the enteric nervous system disorder symptom comprises nausea. In other embodiments, the enteric nervous system disorder symptom comprises vomiting.

The present application provides a method of treating gastroparesis in a human subject in need thereof, comprising administering to the subject any of the foregoing pharmaceutical compositions. In certain embodiments, the gastroparesis is diabetic gastroparesis. In other embodiments, the gastroparesis is idiopathic gastroparesis. In certain embodiments of the foregoing, the gastroparesis comprises a symptom selected from the group consisting of early satiety, post-prandial fullness, abdominal fullness, nausea, vomiting, delayed gastric emptying, diarrhea, abdominal pain, gas, bloating, gastroesophageal reflux, reduced appetite, and constipation. In certain such embodiments, the gastroparesis symptom comprises nausea. In other embodiments, the gastroparesis symptom comprises vomiting.

The present application provides a method of treating nausea associated with gastroparesis in a human subject in need thereof, comprising administering to the subject any of the foregoing pharmaceutical compositions.

The present application provides a method of treating vomiting associated with gastroparesis in a human subject in need thereof, comprising administering to the subject any of the foregoing pharmaceutical compositions.

The present application provides a method of improving gastric emptying in a human subject in need thereof, comprising administering to the subject any of the foregoing pharmaceutical compositions.

The present application provides a method of treating functional and motility disorders of the GI tract in a human subject in need thereof, comprising administering to the subject any of the foregoing pharmaceutical compositions.

In certain embodiments of any of the foregoing methods, the pharmaceutical composition is administered to the subject chronically. In other embodiments of any of the foregoing methods, the pharmaceutical composition is administered to the subject acutely.

In certain embodiments of any of the foregoing methods, the pharmaceutical composition is administered to the subject for at least 6 days. In certain such embodiments, the pharmaceutical composition is administered to the subject for at least 7 days. In certain embodiments, the subject for at least four weeks. In certain embodiments, the pharmaceutical composition is administered to the subject for at least 12 weeks.

In certain embodiments of any of the foregoing methods, the pharmaceutical composition is administered to the subject one time per day. In certain embodiments, the pharmaceutical composition is administered to the subject two times per day. In certain embodiments, the pharmaceutical composition is administered to the subject three times per day. In certain embodiments, the pharmaceutical composition is administered to the subject four times per day.

In certain embodiments of any of the foregoing methods, between about 5 mg and about 160 mg of the metopimazine mesylate is administered to the subject per day. In certain such embodiments, more than 20 mg of metopimazine mesylate is administered to the subject per day.

DETAILED DESCRIPTION OF THE APPLICATION

Figure 1:
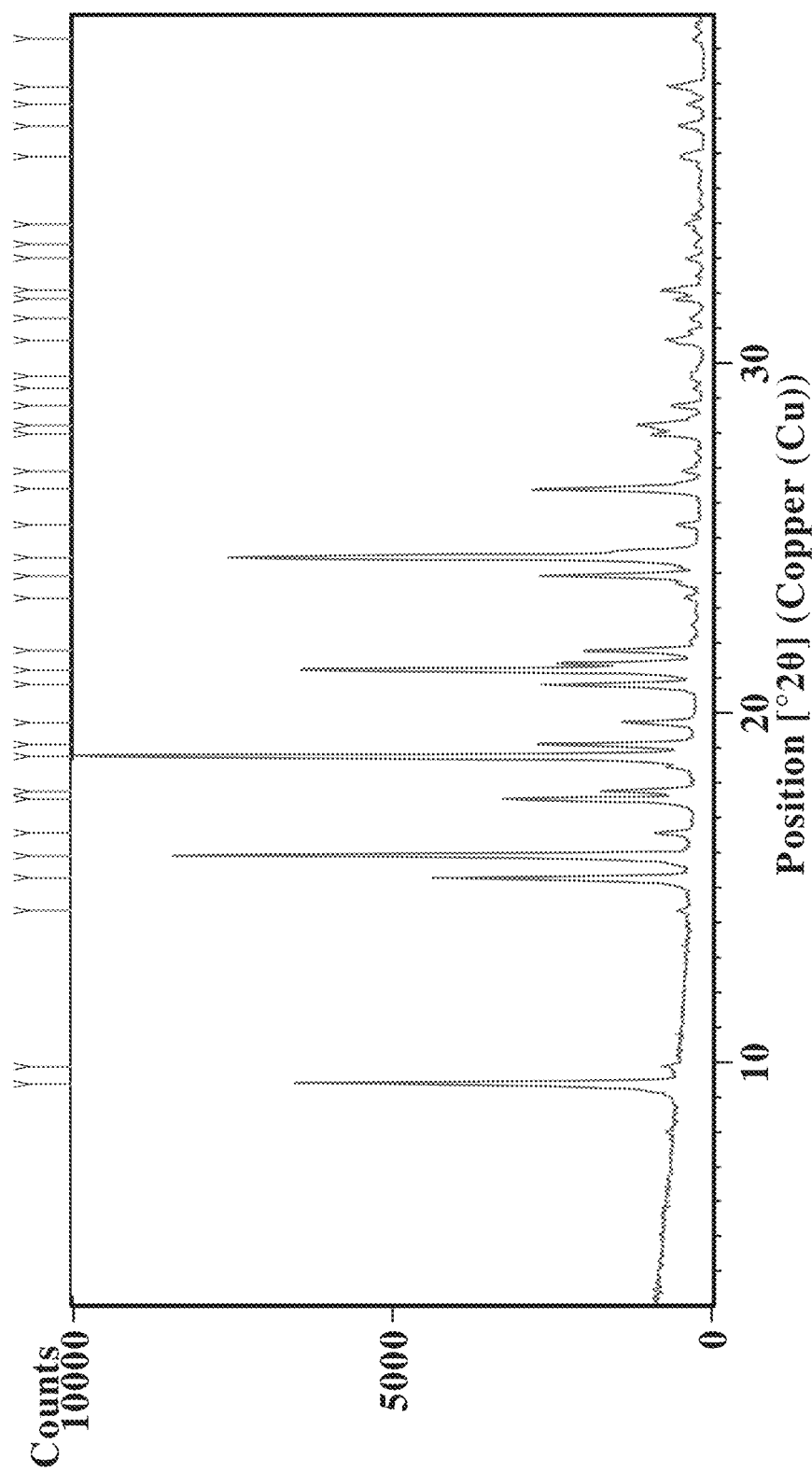
FIG. 1 depicts the X-ray powder diffractogram (XRPD) of metopimazine mesylate Crystal Form A.

The present application provides a crystalline form of metopimazine mesylate,

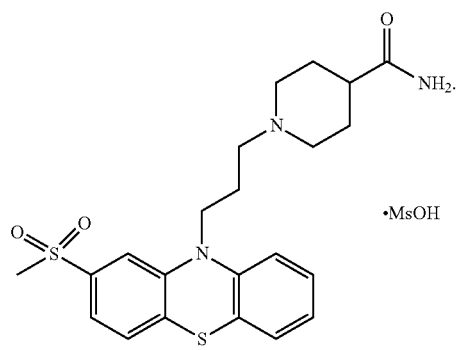 [SMILES: "·MsOH" ; CS(=O)(=O)c1ccc2c(c1)N(CCCN1CCC(C(N)=O)CC1)c1ccccc1S2]

In certain embodiments of the present application, the crystalline form of metopimazine mesylate comprises less than 10 wt. % of other crystalline forms, such as less than 5 wt. %, less than 4 wt. %, less than 3 wt. %, less than 2 wt. %, less than 1 wt. %, less than 0.1 wt. %, or less than 0.01 wt. % of other crystalline forms.

In certain embodiments of the present application, the crystalline form of metopimazine mesylate comprises less than 10 wt. % of amorphous forms, such as less than 5 wt. %, less than 4 wt. %, less than 3 wt. %, less than 2 wt. %, less than 1 wt. %, less than 0.1 wt. %, or less than 0.01 wt. % of amorphous forms.

In certain embodiments of the present application, the crystalline form of metopimazine mesylate comprises less than 10 wt. % of other forms (e.g., other crystalline forms of metopimazine mesylate or other amorphous forms of metopimazine mesylate), such as less than 5 wt. %, less than 4 wt. %, less than 3 wt. %, less than 2 wt. %, less than 1 wt. %, less than 0.1 wt. %, or less than 0.01 wt. % of other forms (e.g., other crystalline forms of metopimazine mesylate or other amorphous forms of metopimazine mesylate).

In certain embodiments of the present application, the crystalline form of metopimazine mesylate is in a non-solvate form. In certain such embodiments of the present application, the crystalline form of metopimazine mesylate comprises less than 10 wt. % of solvate forms, such as less than 5 wt. %, less than 4 wt. %, less than 3 wt. %, less than 2 wt. %, less than 1 wt. %, less than 0.1 wt. %, or less than 0.01 wt. % of solvate forms.

In certain embodiments of the present application, the crystalline form of metopimazine mesylate is in a non-hydrate form. In certain such embodiments, the crystalline form of metopimazine mesylate includes between about 10% metopimazine mesylate non-hydrate and about 100% metopimazine mesylate non-hydrate. For example, the crystalline form of metopimazine mesylate includes about 10% metopimazine mesylate non-hydrate, about 20% metopimazine mesylate non-hydrate, about 30% metopimazine mesylate non-hydrate, about 40% metopimazine mesylate non-hydrate, about 50% metopimazine mesylate non-hydrate, about 60% metopimazine mesylate non-hydrate, about 70% metopimazine mesylate non-hydrate, about 80% metopimazine mesylate non-hydrate, about 90% metopimazine mesylate non-hydrate, or about 95% metopimazine mesylate non-hydrate. In certain such embodiments of the present application, the crystalline form of metopimazine mesylate comprises less than 10 wt. % of hydrate forms, such as less than 5 wt. %, less than 4 wt. %, less than 3 wt. %, less than 2 wt. %, less than 1 wt. %, less than 0.1 wt. %, or less than 0.01 wt. % of hydrate forms.

In certain embodiments of the present application, the crystalline form of metopimazine mesylate is in a solvate form, such as a hydrate form (e.g., mono-hydrate form). In certain such embodiments, the crystalline form of metopimazine mesylate includes between about 10% metopimazine mesylate mono-hydrate and about 100% metopimazine mesylate mono-hydrate. For example, the crystalline form of metopimazine mesylate includes about 10% metopimazine mesylate mono-hydrate, about 20% metopimazine mesylate non-hydrate, about 30% metopimazine mesylate mono-hydrate, about 40% metopimazine mesylate mono-hydrate, about 50% metopimazine mesylate mono-hydrate, about 60% metopimazine mesylate mono-hydrate, about 70% metopimazine mesylate mono-hydrate, about 80% metopimazine mesylate mono-hydrate, about 90% metopimazine mesylate mono-hydrate, or about 95% metopimazine mesylate mono-hydrate. In certain such embodiments of the present application, the crystalline form of metopimazine mesylate comprises less than 10 wt. % of other solvate forms or non-solvate forms, such as less than 5 wt. %, less than 4 wt. %, less than 3 wt. %, less than 2 wt. %, less than 1 wt. %, less than 0.1 wt. %, or less than 0.01 wt. % of other solvate forms or non-solvate forms.

The present application provides metopimazine mesylate Crystal Form A,

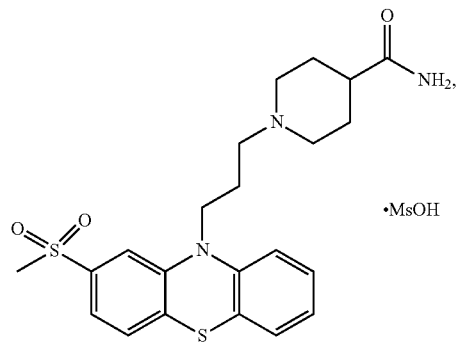 [SMILES: "·MsOH" ; CS(=O)(=O)c1ccc2c(c1)N(CCCN1CCC(C(N)=O)CC1)c1ccccc1S2]

characterized by an X-ray powder diffraction (XRPD) pattern comprising one or more of the 2-theta (2θ) values provided in Table 1. The diffraction pattern was recorded with Cu, Kα radiation.

TABLE 1

Peaks identified on XRPD for metopimazine mesylate Crystal Form A

| Pos. [°2θ] | Height [cts] | FWHM Left [°2θ] | d-spacing [Å] | Rel. Int. [%] |
|---|---|---|---|---|
| 9.37 | 4920.97 | 0.1535 | 9.44 | 50.55 |
| 9.87 | 263.66 | 0.1023 | 8.96 | 2.71 |
| 14.33 | 157.71 | 0.1535 | 6.18 | 1.62 |
| 15.26 | 4020.53 | 0.1023 | 5.81 | 41.30 |
| 15.91 | 8116.56 | 0.1023 | 5.57 | 83.38 |
| 16.55 | 551.07 | 0.1023 | 5.36 | 5.66 |
| 17.52 | 2956.27 | 0.1023 | 5.06 | 30.37 |
| 17.75 | 1422.83 | 0.1023 | 5.00 | 14.62 |
| 18.75 | 9734.71 | 0.1279 | 4.73 | 100.00 |
| 19.09 | 2488.96 | 0.1023 | 4.65 | 25.57 |
| 19.72 | 1116.67 | 0.1279 | 4.50 | 11.47 |
| 20.80 | 2397.36 | 0.1023 | 4.27 | 24.63 |
| 21.22 | 6352.12 | 0.1023 | 4.19 | 65.25 |
| 21.77 | 1801.77 | 0.1023 | 4.08 | 18.51 |
| 23.29 | 179.97 | 0.1023 | 3.82 | 1.85 |
| 23.91 | 2465.28 | 0.1023 | 3.72 | 25.32 |
| 24.44 | 7334.27 | 0.1023 | 3.64 | 75.34 |
| 25.37 | 346.61 | 0.1023 | 3.51 | 3.56 |
| 26.39 | 2648.50 | 0.1023 | 3.38 | 27.21 |
| 26.92 | 265.75 | 0.1279 | 3.31 | 2.73 |
| 27.96 | 766.29 | 0.1023 | 3.19 | 7.87 |
| 28.23 | 980.13 | 0.1535 | 3.16 | 10.07 |
| 28.78 | 457.50 | 0.1279 | 3.10 | 4.70 |
| 29.27 | 115.22 | 0.1023 | 3.05 | 1.18 |
| 29.64 | 137.61 | 0.2558 | 3.01 | 1.41 |
| 30.67 | 569.41 | 0.1023 | 2.92 | 5.85 |
| 31.29 | 166.89 | 0.1535 | 2.86 | 1.71 |
| 31.84 | 407.68 | 0.1023 | 2.81 | 4.19 |
| 32.09 | 647.44 | 0.1535 | 2.79 | 6.65 |
| 32.99 | 257.23 | 0.1279 | 2.72 | 2.64 |
| 33.40 | 118.31 | 0.1535 | 2.68 | 1.22 |
| 33.99 | 283.82 | 0.1023 | 2.64 | 2.92 |
| 35.91 | 333.91 | 0.2047 | 2.50 | 3.43 |
| 36.80 | 388.57 | 0.1791 | 2.44 | 3.99 |
| 37.41 | 242.65 | 0.1535 | 2.40 | 2.49 |
| 37.92 | 565.14 | 0.1535 | 2.37 | 5.81 |
| 39.27 | 174.37 | 0.1279 | 2.29 | 1.79 |

In certain embodiments, metopimazine mesylate Crystal Form A is characterized by an XRPD pattern comprising at least two 2θvalues selected from those set forth in Table 1. In certain embodiments, the metopimazine mesylate Crystal Form A is characterized by an XRPD pattern comprising at least three, at least four, at least five, at least six, at least seven, at least eight, or at least nine 2θvalues selected from those set forth in Table 1. In certain embodiments, the metopimazine mesylate Crystal Form A is characterized by one or more of the 2θvalues in the range of from about 5 to about 25° 2θ in Table 1. In certain embodiments, the metopimazine mesylate Crystal Form A is characterized by at least two of the 2θvalues in the range of from about 5 to about 25° 2θ in Table 1. In certain embodiments, the metopimazine mesylate Crystal Form A is characterized by at least three, at least four, at least five, at least six, at least seven, at least eight, or at least nine of the 2θvalues in the range of from about 5 to about 25° 2θ in Table 1. In certain embodiments, the metopimazine mesylate Crystal Form A is characterized by an XRPD pattern comprising the 2θvalues selected from those set forth in Table 1. It will be appreciated by a person skilled in the art that the XRPD intensities may vary between different samples and different sample preparations for a variety of reasons including preferred orientation. It will also be appreciated by a person skilled in the art that smaller shifts in the measured Angle and hence the d-spacing may occur for a variety of reasons including variation of Sample Surface level in the diffractometer. It will further be appreciated by a person skilled in the art that the 2θdegrees provided in Table 1 will generally be reproducible to within a range of from about ±0.10 2θdegrees to about ±0.20 2θdegrees, with a preferred range being about ±0.10 2θdegrees. See e.g., United States Pharmacopoeia XXV (2002), p. 2088-2089.

In certain embodiments, metopimazine mesylate Crystal Form A is characterized by an XRPD pattern comprising one or more of the following 2θvalues: 9.37°, 15.26°, 15.91°, 18.75°, 19.09°, 20.80°, 21.22°, 21.77°, and 24.44°±0.10-0.20 2θ. In certain embodiments, metopimazine mesylate Crystal Form A is characterized by an XRPD)pattern comprising two or more of the following 2θvalues: 9.37°, 15.26°, 15.91°, 18.75°, 19.09°, 20.80°, 21.22°, 21.77°, and 24.44°±0.10-0.20 2θ. In certain embodiments, metopimazine mesylate Crystal Form A is characterized by an XRPD pattern comprising three or more of the following 2θvalues: 9.37°, 15.26°, 15.91°, 18.75°, 19.09°, 20.80°, 21.22°, 21.77°, and 24.44°±0.10-0.20 2θ. In certain embodiments, metopimazine mesylate Crystal Form A is characterized by an XRPD pattern comprising four or more of the following 2θvalues: 9.37°, 15.26°, 15.91°, 18.75°, 19.09°, 20.80°, 21.22°, 21.77°, and 24.44°±0.10-0.20 2θ. In certain embodiments, metopimazine mesylate Crystal Form A is characterized by an XRPD pattern comprising five or more of the following 2θvalues: 9.37°, 15.26°, 15.91°, 18.75°, 19.09°, 20.80°, 21.22°, 21.77°, and 24.44°±0.10-0.20 2θ.

In certain embodiments, metopimazine mesylate Crystal Form A is characterized by an XRPD pattern comprising a peak at the following 2θvalue 18.75°±0.10-0.20 2θ. In certain embodiments, metopimazine mesylate Crystal Form A is characterized by an XRPD pattern comprising peaks at the following 2θvalues 15.91° and 18.75°±0.10-0.20 2θ. In certain embodiments, metopimazine mesylate Crystal Form A is characterized by an XRPD pattern comprising peaks at the following 2θvalues 15.91°, 18.75°, and 24.44°±0.10-0.20 2θ. In certain embodiments, metopimazine mesylate Crystal Form A is characterized by an XRPD pattern comprising peaks at the following 2θvalues 15.91°, 18.75°, 21.22°, and 24.44°±0.10-0.20 2θ. In certain embodiments, metopimazine mesylate Crystal Form A is characterized by an XRPD pattern comprising peaks at the following 2θvalues 9.37°, 15.91°, 18.75°, 21.22°, and 24.44°±0.10-0.20 2θ. In certain embodiments, metopimazine mesylate Crystal Form A is characterized by an XRPD pattern comprising peaks at the following 2θvalues 9.37°, 15.26°, 15.91°, 18.75°, 21.22°, and 24.44°±0.10-0.20 2θ.

The present application provides metopimazine mesylate Crystal Form A, characterized by an XRPD pattern comprising at least two D-spacing values selected from those set forth in Table 1. In certain embodiments, the metopimazine mesylate Crystal Form A is characterized by an XRPD pattern comprising at least three, at least four, at least five, or at least six D-spacing values selected from those set forth in Table 1. In certain embodiments, the metopimazine mesylate Crystal Form A is characterized by an XRPD pattern comprising the D-spacing values selected from those set forth in Table 1.

In certain embodiments, the metopimazine mesylate Crystal Form A is characterized by an XRPD pattern as set forth in Table 1. In certain embodiments, the metopimazine mesylate Crystal Form A exhibits an XRPD pattern as set forth in FIG. 1.

Figure 3:
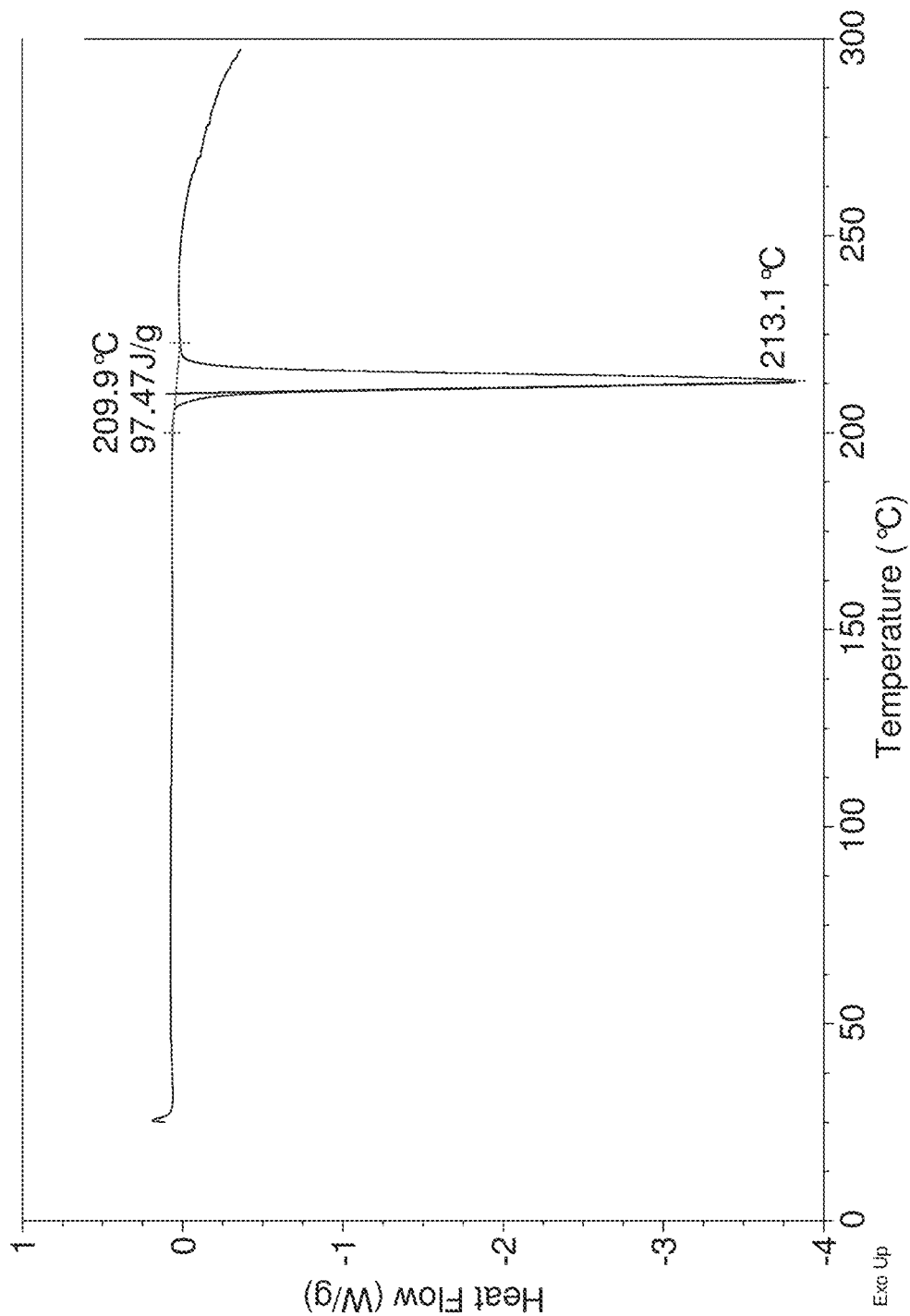
FIG. 3 depicts the differential scanning calorimetry (DSC) plot for metopimazine mesylate Crystal Form A.

In certain embodiments, the metopimazine mesylate Crystal Form A is characterized by a differential scanning calorimetry (DSC) pattern comprising a single endotherm with an onset temperature range of 208° C. to 212° C., or 208° C. to 211° C., such as 209° C. to 210° C. (e.g., 209.9° C.). In certain embodiments, the metopimazine mesylate Crystal Form A is characterized by a DSC pattern comprising a single endotherm with a peak temperature range of 213° C. to 214° C. (e.g., 213.1° C.). It will be appreciated by a person skilled in the art that the endotherm given above and in FIG. 3 will typically be reproducible to within a range of from ±0.5 to 3° C., such as ±2° C., ±1° C., or ±0.5° C. In certain embodiments, the metopimazine mesylate Crystal Form A is characterized by a DSC pattern comprising a single endotherm with an enthalpy of transition of 95-100 J/g, such as 96-98 J/g, 97-98 J/g, or 97.5 J/g (e.g., 97.47 J/g). In certain embodiments, the metopimazine mesylate Crystal Form A is characterized by a DSC pattern as set forth in FIG. 3.

Figure 2:
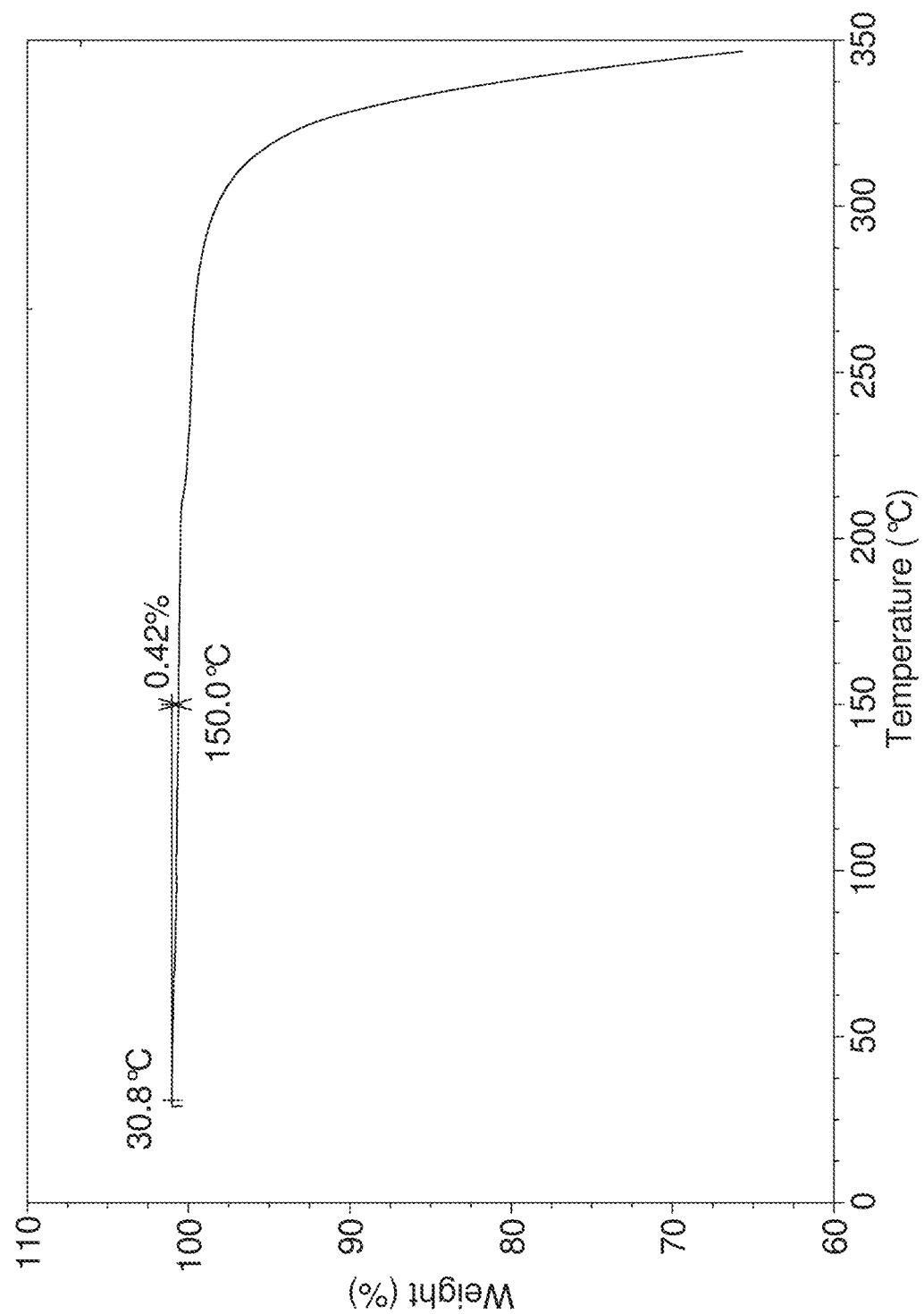
FIG. 2 depicts the thermogravimetric analysis (TGA) plot for metopimazine mesylate Crystal Form A.

In certain embodiments, the metopimazine mesylate Crystal Form A is characterized by a thermogravimetric analysis (TGA) profile with a total weight loss of 0.4% (e.g., 0.42%) up to 150.0° C. In certain embodiments, the metopimazine mesylate Crystal Form A is characterized by a TGA profile as set forth in FIG. 2.

In certain embodiments of the present application, the metopimazine mesylate Crystal Form A comprises less than 10 wt. % of other crystal forms (e.g., metopimazine mesylate hydrate Crystal Form B), such as less than 5 wt. %, less than 4 wt. %, less than 3 wt. %, less than 2 wt. %, less than 1 wt. %, less than 0.1 wt. %, or less than 0.01 wt. % of other crystal forms (e.g., metopimazine mesylate hydrate Crystal Form B).

In certain embodiments of the present application, the metopimazine mesylate Crystal Form A comprises less than 10 wt. % of amorphous forms, such as less than 5 wt. %, less than 4 wt. %, less than 3 wt. %, less than 2 wt. %, less than 1 wt. %, less than 0.1 wt. %, or less than 0.01 wt. % of amorphous forms.

In certain embodiments of the present application, metopimazine mesylate Crystal Form A comprises less than 10 wt. % of other forms (e.g., other crystalline forms of metopimazine mesylate, such as metopimazine mesylate Crystal Form B, or other amorphous forms of metopimazine mesylate), such as less than 5 wt. %, less than 4 wt. %, less than 3 wt. %, less than 2 wt. %, less than 1 wt. %, less than 0.1 wt. %, or less than 0.01 wt. % of other forms (e.g., other crystalline forms of metopimazine mesylate, such as metopimazine mesylate Crystal Form B, or other amorphous forms of metopimazine mesylate).

In certain embodiments of the present application, the metopimazine mesylate Crystal Form A is in a non-solvate form. In certain such embodiments of the present application, the metopimazine mesylate Crystal Form A comprises less than 10 wt. % of solvate forms, such as less than 5 wt. %, less than 4 wt. %, less than 3 wt. %, less than 2 wt. %, less than 1 wt. %, less than 0.1 wt. %, or less than 0.01 wt. % of solvate forms.

In certain embodiments of the present application, the metopimazine mesylate Crystal Form A is in a non-hydrate form. In certain such embodiments of the present application, the metopimazine mesylate Crystal Form A comprises less than 10 wt. % of hydrate forms, such as less than 5 wt. %, less than 4 wt. %, less than 3 wt. %, less than 2 wt. %, less than 1 wt. %, less than 0.1 wt. %, or less than 0.01 wt. % of hydrate forms.

The present application provides metopimazine mesylate hydrate Crystal Form B,

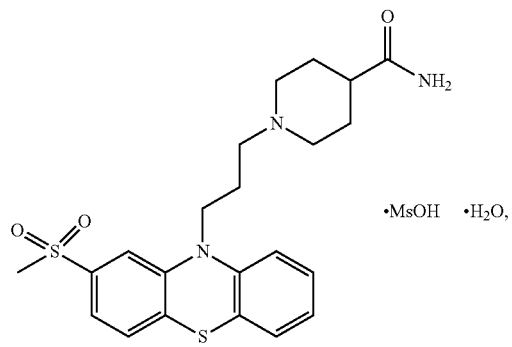 [SMILES: "·MsOH" ; CS(=O)(=O)c1ccc2c(c1)N(CCCN1CCC(C(N)=O)CC1)c1ccccc1S2 ; "·H2O,"]

characterized by an XRPD pattern comprising one or more of the 2θ values selected from those set forth in Table 2. The diffraction pattern was recorded with Cu, Kα radiation.

TABLE 2

Peaks identified on XRPD for metopimazine mesylate hydrate Crystal Form B

| Pos. [°2θ] | Height [cts] | FWHM Left [°2θ] | d-spacing [Å] | Rel. Int. [%] |
|---|---|---|---|---|
| 4.64 | 189.84 | 0.1023 | 19.06 | 14.72 |
| 8.57 | 131.03 | 0.1535 | 10.31 | 10.16 |
| 10.71 | 363.36 | 0.2047 | 8.26 | 28.18 |
| 11.12 | 384.47 | 0.1023 | 7.96 | 29.82 |
| 11.75 | 193.62 | 0.1535 | 7.53 | 15.02 |
| 12.51 | 266.85 | 0.3070 | 7.07 | 20.70 |
| 13.47 | 184.58 | 0.1023 | 6.57 | 14.32 |
| 13.87 | 118.39 | 0.1535 | 6.38 | 9.18 |
| 15.82 | 359.17 | 0.1535 | 5.60 | 27.86 |
| 16.30 | 661.61 | 0.1023 | 5.44 | 51.31 |
| 16.90 | 1289.39 | 0.1535 | 5.25 | 100.00 |
| 17.29 | 205.33 | 0.1535 | 5.13 | 15.92 |
| 17.60 | 331.98 | 0.1023 | 5.04 | 25.75 |
| 17.89 | 325.45 | 0.1023 | 4.96 | 25.24 |
| 18.42 | 899.37 | 0.2047 | 4.82 | 69.75 |
| 18.88 | 506.01 | 0.1023 | 4.70 | 39.24 |
| 19.16 | 543.26 | 0.1535 | 4.63 | 42.13 |
| 20.00 | 749.52 | 0.1535 | 4.44 | 58.13 |
| 20.66 | 212.79 | 0.1535 | 4.30 | 16.50 |
| 21.44 | 394.26 | 0.1535 | 4.14 | 30.58 |
| 22.02 | 439.23 | 0.1535 | 4.04 | 34.07 |
| 22.47 | 476.08 | 0.2047 | 3.96 | 36.92 |
| 23.21 | 519.15 | 0.1535 | 3.83 | 40.26 |
| 23.61 | 520.30 | 0.1023 | 3.77 | 40.35 |
| 24.79 | 259.37 | 0.1023 | 3.59 | 20.12 |
| 25.51 | 700.65 | 0.1023 | 3.49 | 54.34 |
| 26.09 | 158.11 | 0.1023 | 3.42 | 12.26 |
| 26.57 | 235.61 | 0.1535 | 3.36 | 18.27 |
| 27.12 | 309.01 | 0.1023 | 3.29 | 23.97 |
| 27.77 | 169.04 | 0.1535 | 3.21 | 13.11 |
| 28.39 | 168.22 | 0.1023 | 3.14 | 13.05 |
| 28.78 | 229.49 | 0.1535 | 3.10 | 17.80 |
| 32.94 | 117.10 | 0.2303 | 2.72 | 9.08 |
| 36.31 | 80.65 | 0.2558 | 2.47 | 6.25 |

In certain embodiments, metopimazine mesylate Crystal Form B is characterized by an XRPD pattern comprising at least two 2θ values selected from those set forth in Table 2. In certain embodiments, the metopimazine mesylate Crystal Form B is characterized by an XRPD pattern comprising at least three, at least four, at least five, at least six, at least seven, at least eight, or at least nine 2θ values selected from those set forth in Table 2. In certain embodiments, the metopimazine mesylate Crystal Form B is characterized by one or more of the 2θ values in the range of from about 5 to about 25° 2θ in Table 2. In certain embodiments, the metopimazine mesylate Crystal Form B is characterized by at least two of the 2θ values in the range of from about 5 to about 25° 2θ in Table 2. In certain embodiments, the metopimazine mesylate Crystal Form B is characterized by at least three, at least four, at least five, at least six, at least seven, at least eight, or at least nine of the 2θ values in the range of from about 5 to about 25° 2θ in Table 2 In certain embodiments, the metopimazine mesylate hydrate Crystal Form B is characterized by an XRPD pattern comprising the 2θ values selected from those set forth in Table 2. It will further be appreciated by a person skilled in the art that the 2θ degrees provided in Table 2 will generally be reproducible to within a range of from about ±0.10 2θ degrees to about ±0.20 2θ degrees, with a preferred range being about ±0.10 2θ degrees. See e.g., United States Pharmacopoeia XXV (2002), p. 2088-2089.

In certain embodiments, metopimazine mesylate Crystal Form B is characterized by an XRPD pattern comprising one or more of the following 2θ values: 4.64°, 10.71°, 11.12°, 16.30°, 16.90°, 17.89°, 20.00°, and 27.12°±0.10-0.20 2θ. In certain embodiments, metopimazine mesylate Crystal Form B is characterized by an XRPD pattern comprising two or more of the following 2θ values: 4.64°, 10.71°, 11.12°, 16.30°, 16.90°, 17.89°, 20.00°, and 27.12°±0.10-0.20 2θ. In certain embodiments, metopimazine mesylate Crystal Form B is characterized by an XRPD pattern comprising three or more of the following 2θ values 4.64°, 10.71°, 11.12°, 16.30°, 16.90°, 17.89°, 20.00°, and 27.12°±0.10-0.20 2θ. In certain embodiments, metopimazine mesylate Crystal Form B is characterized by an XRPD pattern comprising four or more of the following 2θ values: 4.64°, 10.71°, 11.12°, 16.30°, 16.90°, 17.89°, 20.00°, and 27.12°±0.10-0.20 2θ. In certain embodiments, metopimazine mesylate Crystal Form B is characterized by an XRPD pattern comprising five or more of the following 2θ values: 4.64°, 10.71°, 11.12°, 16.30°, 16.90°, 17.89°, 20.00°, and 27.12°±0.10-0.20 2θ.

In certain embodiments, metopimazine mesylate Crystal Form B is characterized by an XRPD pattern comprising a peak at the following 2θ value 16.90°±0.10-0.20 2θ. In certain embodiments, metopimazine mesylate Crystal Form B is characterized by an XRPD pattern comprising peaks at the following 2θ values 16.90° and 20.00°±0.10-0.20 2θ. In certain embodiments, metopimazine mesylate Crystal Form B is characterized by an XRPD pattern comprising peaks at the following 2θ values 16.30°, 16.90°, and 20.00°±0.10-0.20 2θ. In certain embodiments, metopimazine mesylate Crystal Form B is characterized by an XRPD pattern comprising peaks at the following 2θ values 11.12°, 16.30°, 16.90°, and 20.00°±0.10-0.20 2θ. In certain embodiments, metopimazine mesylate Crystal Form B is characterized by an XRPD pattern comprising peaks at the following 2θ values 10.71°, 16.30°, 16.90°, and 20.00°±0.10-0.20 2θ. In certain embodiments, metopimazine mesylate Crystal Form B is characterized by an XRPD pattern comprising peaks at the following 2θ values 16.30°, 16.90°, 17.89°, and 20.00°±0.10-0.20 2θ. In certain embodiments, metopimazine mesylate Crystal Form B is characterized by an XRPD pattern comprising peaks at the following 2θ values 16.30°, 16.90°, 20.00° and 27.12°±0.10-0.20 2θ. In certain embodiments, metopimazine mesylate Crystal Form B is characterized by an XRPD pattern comprising peaks at the following 2θ values 10.71°, 11.12°, 16.30°, 16.90°, and 20.00°±0.10-0.20 2θ. In certain embodiments, metopimazine mesylate Crystal Form B is characterized by an XRPD pattern comprising peaks at the following 2θ values 10.71°, 11.12°, 16.30°, 16.90°, 17.89°, 20.00° and 27.12°±0.10-0.20 2θ.

The present application provides metopimazine mesylate hydrate Crystal Form B, characterized by an XRPD pattern comprising at least two D-spacing values selected from those set forth in Table 2. In certain embodiments, the metopimazine mesylate hydrate Crystal Form B is characterized by an XRPD pattern comprising at least three, at least four, at least five, or at least six D-spacing values selected from those set forth in Table 2. In certain embodiments, the metopimazine mesylate hydrate Crystal Form B is characterized by an XRPD pattern comprising the D-spacing values selected from those set forth in Table 2.

In certain embodiments, the metopimazine mesylate hydrate Crystal Form B is characterized by an XRPD pattern as set forth in Table 2.

Figure 5:
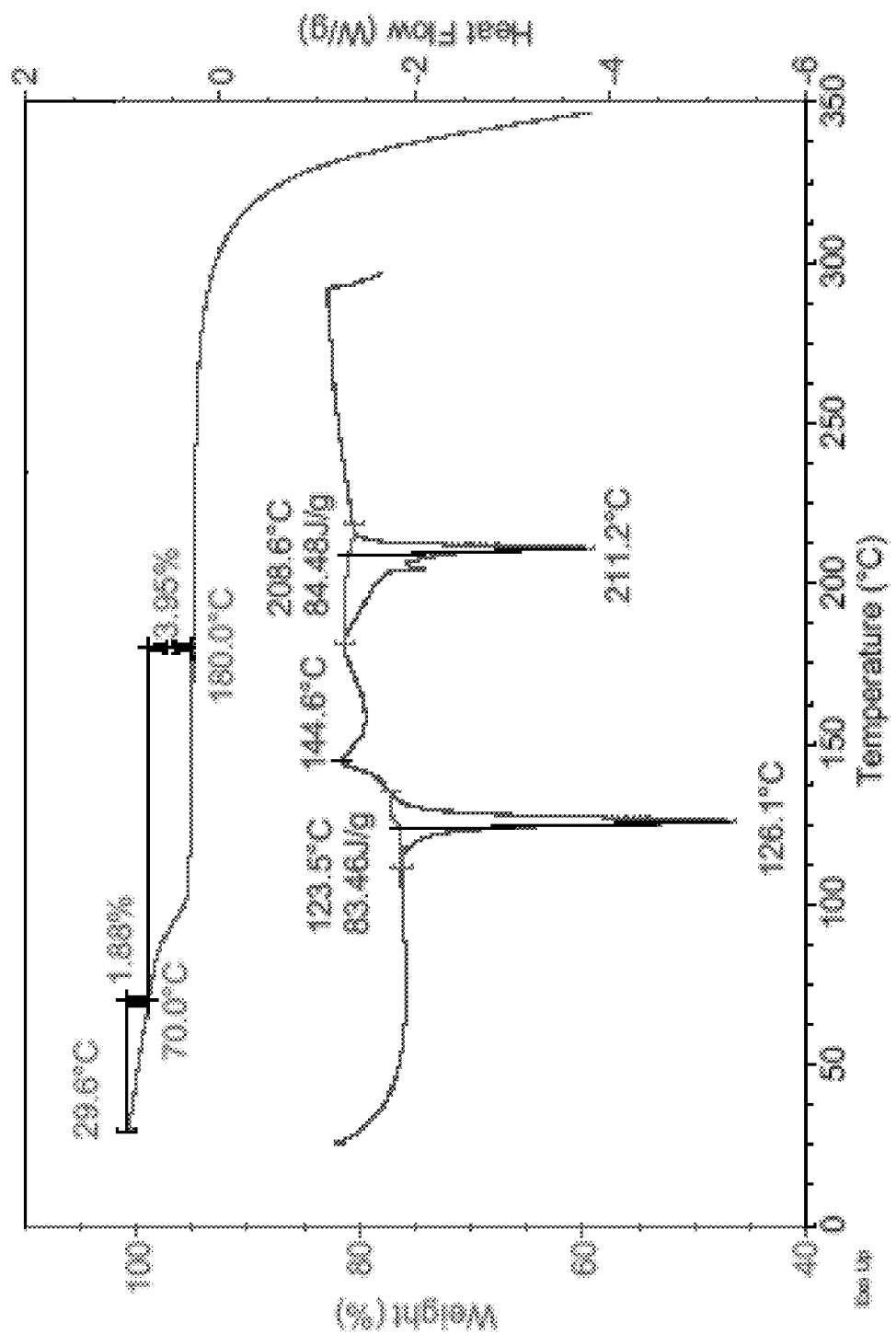
FIG. 5 depicts the TGA and DSC plots for metopimazine mesylate Crystal Form B.

In certain embodiments, the metopimazine mesylate Crystal Form B is characterized by a DSC pattern comprising two endothermic peaks and a single exothermic peak. In certain such embodiments, the metopimazine mesylate Crystal Form B is characterized by a DSC pattern comprising a first endothermic peak having an onset temperature range of 122° C. to 125° C., or 123° C. to 124° C. (e.g., 123.5° C.). In certain embodiments, the metopimazine mesylate Crystal Form B is characterized by a DSC pattern comprising a first endotherm with a peak temperature range of 125° C. to 127° C., such as 126° C. to 127° C. (e.g., 126.1° C.). In certain such embodiments, the metopimazine mesylate Crystal Form B is characterized by a DSC pattern comprising a first endotherm with an enthalpy of transition of 81-86 J/g, such as 82-85 J/g, 83-84 J/g, or 83.5 J/g (e.g., 83.47 J/g). In certain such embodiments, the metopimazine mesylate Crystal Form B is characterized by a DSC pattern comprising a second endothermic peak having an onset temperature range of 207° C. to 210° C., or 208° C. to 209° C. (e.g., 208.6° C.). In certain embodiments, the metopimazine mesylate Crystal Form B is characterized by a DSC pattern comprising a second endotherm with a peak temperature range of 210° C. to 212° C., such as 211° C. to 212° C. (e.g., 211.2° C.). In certain such embodiments, the metopimazine mesylate Crystal Form B is characterized by a DSC pattern comprising a second endotherm with an enthalpy of transition of 82-87 J/g, such as 83-86 J/g, 84-85 J/g, or 84.5 J/g (e.g., 84.48 J/g). In certain such embodiments, the metopimazine mesylate Crystal Form B is characterized by a DSC pattern comprising a single exothermic peak with a peak temperature range of 143° C. to 146° C., such as 144° C. to 145° C. (e.g., 144.6° C.). It will be appreciated by a person skilled in the art that the endotherms and exotherm given above and in FIG. 5 will typically be reproducible to within a range of from ±0.5 to 3° C., such as ±2° C., ±1° C., or ±0.5° C. In certain embodiments, the metopimazine mesylate Crystal Form B is characterized by a DSC pattern as set forth in FIG. 5.

In certain embodiments, the metopimazine mesylate Crystal Form B is characterized by a TGA profile with a total weight loss of 5.5-6% (e.g., 5.8%) up to 180.0° C. In certain embodiments, the metopimazine mesylate Crystal Form B is characterized by a TGA profile as set forth in FIG. 5.

In certain embodiments of the present application, the metopimazine mesylate hydrate Crystal Form B comprises less than 10 wt. % of other crystal forms (e.g., metopimazine mesylate Crystal Form A), such as less than 5 wt. %, less than 4 wt. %, less than 3 wt. %, less than 2 wt. %, less than 1 wt. %, less than 0.1 wt. %, or less than 0.01 wt. % of other crystal forms (e.g., metopimazine mesylate Crystal Form A).

In certain embodiments of the present application, the metopimazine mesylate hydrate Crystal Form B comprises less than 10 wt. % of amorphous forms, such as less than 5 wt. %, less than 4 wt. %, less than 3 wt. %, less than 2 wt. %, less than 1 wt. %, less than 0.1 wt. %, or less than 0.01 wt. % of amorphous forms.

In certain embodiments of the present application, metopimazine mesylate Crystal Form B comprises less than 10 wt. % of other forms (e.g., other crystalline forms of metopimazine mesylate, such as metopimazine mesylate Crystal Form A, or other amorphous forms of metopimazine mesylate), such as less than 5 wt. %, less than 4 wt. %, less than 3 wt. %, less than 2 wt. %, less than 1 wt. %, less than 0.1 wt. %, or less than 0.01 wt. % of other forms (e.g., other crystalline forms of metopimazine mesylate, such as metopimazine mesylate Crystal Form A, or other amorphous forms of metopimazine mesylate).

In certain embodiments of the present application, the metopimazine mesylate Crystal Form B is in mono-hydrate form. In certain such embodiments of the present application, the metopimazine mesylate Crystal Form B comprises less than 10 wt. % of other solvate forms or non-solvate forms, such as less than 5 wt. %, less than 4 wt. %, less than 3 wt. %, less than 2 wt. %, less than 1 wt. %, less than 0.1 wt. %, or less than 0.01 wt. % of other solvate forms or non-solvate forms.

The present application provides a pharmaceutical composition comprising metopimazine mesylate Crystal Form A, and a pharmaceutically acceptable carrier. In certain such embodiments, the pharmaceutical composition includes between about 10% metopimazine mesylate Crystal Form A and about 100% metopimazine mesylate Crystal Form A. For example, the pharmaceutical composition includes about 10% metopimazine mesylate Crystal Form A, about 20% metopimazine mesylate Crystal Form A, about 30% metopimazine mesylate Crystal Form A, about 40% metopimazine mesylate Crystal Form A, about 50% metopimazine mesylate Crystal Form A, about 60% metopimazine mesylate Crystal Form A, about 70% metopimazine mesylate Crystal Form A, about 80% metopimazine mesylate Crystal Form A, about 90% metopimazine mesylate Crystal Form A, or about 95% metopimazine mesylate Crystal Form A.

In certain embodiments of the present application, pharmaceutical composition comprising metopimazine mesylate Crystal Form A comprises less than 10 wt. % of other forms of metopimazine mesylate (e.g., other crystalline forms of metopimazine mesylate, such as metopimazine mesylate Crystal Form B, or other amorphous forms of metopimazine mesylate), such as less than 5 wt. %, less than 4 wt. %, less than 3 wt. %, less than 2 wt. %, less than 1 wt. %, less than 0.1 wt. %, or less than 0.01 wt. % of other forms of metopimazine mesylate (e.g., other crystalline forms of metopimazine mesylate, such as metopimazine mesylate Crystal Form B, or other amorphous forms of metopimazine mesylate).

The present application provides a pharmaceutical composition comprising metopimazine mesylate Crystal Form B, and a pharmaceutically acceptable carrier. In certain such embodiments, the pharmaceutical composition includes between about 10% metopimazine mesylate Crystal Form B and about 100% metopimazine mesylate Crystal Form B. For example, the pharmaceutical composition includes about 10% metopimazine mesylate Crystal Form B, about 20% metopimazine mesylate Crystal Form B, about 30% metopimazine mesylate Crystal Form B, about 40% metopimazine mesylate Crystal Form B, about 50% metopimazine mesylate Crystal Form B, about 60% metopimazine mesylate Crystal Form B, about 70% metopimazine mesylate Crystal Form B, about 80% metopimazine mesylate Crystal Form B, about 90% metopimazine mesylate Crystal Form B, or about 95% metopimazine mesylate Crystal Form B.

In certain embodiments of the present application, pharmaceutical composition comprising metopimazine mesylate Crystal Form B comprises less than 10 wt. % of other forms of metopimazine mesylate (e.g., other crystalline forms of metopimazine mesylate, such as metopimazine mesylate Crystal Form A, or other amorphous forms of metopimazine mesylate), such as less than 5 wt. %, less than 4 wt. %, less than 3 wt. %, less than 2 wt. %, less than 1 wt. %, less than 0.1 wt. %, or less than 0.01 wt. % of other forms of metopimazine mesylate (e.g., other crystalline forms of metopimazine mesylate, such as metopimazine mesylate Crystal Form A, or other amorphous forms of metopimazine mesylate).

In certain embodiments of any of the pharmaceutical compositions comprising a crystalline form of metopimazine mesylate (e.g., metopimazine mesylate Crystal Form A or metopimazine mesylate Crystal Form B) as described herein, the composition is suitable for administering orally, intraduodenally, intracolonically, parenterally, enterally, intraperitoneally, topically, transdermally, ophthalmically, intranasally, locally, non-orally, via spray, subcutaneously, intravenously, intratonsillary, intramuscularly, buccally, sublingually, rectally, intra-arterially, by infusion, or intrathecally. In certain embodiments, the composition is suitable for administering orally. In certain embodiments, the composition is suitable for administering sublingually.

In certain embodiments of any of the pharmaceutical compositions comprising a crystalline form of metopimazine mesylate (e.g., metopimazine mesylate Crystal Form A or metopimazine mesylate Crystal Form B) as described herein, the pharmaceutical composition is formulated as a tablet, a capsule, a cream, a lotion, an oil, an ointment, a gel, a paste, a powder, a suspension, a syrup, an enema, a suppository, an emulsion, or a solution, an extended-release formulation, or a modified-release formulation. In certain embodiments, the composition is formulated as an extended release formulation. In certain embodiments, the composition is formulated as a capsule.

In certain embodiments of any of the pharmaceutical compositions comprising a crystalline form of metopimazine mesylate (e.g., metopimazine mesylate Crystal Form A or metopimazine mesylate Crystal Form B) as described herein, the composition comprises 5 mg of the metopimazine mesylate. In certain embodiments of any of the foregoing pharmaceutical compositions comprising a crystalline form of metopimazine mesylate (e.g., metopimazine mesylate Crystal Form A or metopimazine mesylate Crystal Form B), the composition comprises 10 mg of the crystalline form of metopimazine mesylate (e.g., metopimazine mesylate Crystal Form A or metopimazine mesylate Crystal Form B). In certain embodiments of any of the foregoing pharmaceutical compositions comprising a crystalline form of metopimazine mesylate (e.g., metopimazine mesylate Crystal Form A or metopimazine mesylate Crystal Form B), the composition comprises 15 mg of the crystalline form of metopimazine mesylate (e.g., metopimazine mesylate Crystal Form A or metopimazine mesylate Crystal Form B). In certain embodiments of any of the foregoing pharmaceutical compositions comprising a crystalline form of metopimazine mesylate (e.g., metopimazine mesylate Crystal Form A or metopimazine mesylate Crystal Form B), the composition comprises 20 mg of the crystalline form of metopimazine mesylate (e.g., metopimazine mesylate Crystal Form A or metopimazine mesylate Crystal Form B).

In certain embodiments of any of the pharmaceutical compositions comprising a crystalline form of metopimazine mesylate (e.g., metopimazine mesylate Crystal Form A or metopimazine mesylate Crystal Form B) as described herein, the composition is suitable for administration one time per day. In other embodiments of any of the foregoing pharmaceutical compositions comprising a crystalline form of metopimazine mesylate (e.g., metopimazine mesylate Crystal Form A or metopimazine mesylate Crystal Form B), the composition is suitable for administration two times per day. In certain embodiments of any of the foregoing pharmaceutical compositions comprising a crystalline form of metopimazine mesylate (e.g., metopimazine mesylate Crystal Form A or metopimazine mesylate Crystal Form B), the composition is suitable for administration three times per day. In other embodiments of any of the foregoing pharmaceutical compositions comprising a crystalline form of metopimazine mesylate (e.g., metopimazine mesylate Crystal Form A or metopimazine mesylate Crystal Form B), the composition is suitable for administration four times per day.

In certain embodiments of any of the pharmaceutical compositions comprising a crystalline form of metopimazine mesylate (e.g., metopimazine mesylate Crystal Form A or metopimazine mesylate Crystal Form B) as described herein, between about 5 mg and about 160 mg of the crystalline form of metopimazine mesylate (e.g., metopimazine mesylate Crystal Form A or metopimazine mesylate Crystal Form B) is administered per day. In certain embodiments of any of the pharmaceutical compositions comprising a crystalline form of metopimazine mesylate (e.g., metopimazine mesylate Crystal Form A or metopimazine mesylate Crystal Form B) as described herein, between about 5 mg and about 240 mg of the crystalline form of metopimazine mesylate (e.g., metopimazine mesylate Crystal Form A or metopimazine mesylate Crystal Form B) is administered per day, such as about 5 mg, about 10 mg, about 15 mg, about 20 mg, about 30 mg, about 40 mg, about 50 mg, about 60 mg, about 80 mg, about 90 mg, about 100 mg, about 120 mg, about 150 mg, about 160 mg, about 180 mg, about 200 mg, about 240 mg of the crystalline form of metopimazine mesylate (e.g., metopimazine mesylate Crystal Form A or metopimazine mesylate Crystal Form B) is administered per day. In certain embodiments of any of the pharmaceutical compositions comprising a crystalline form of metopimazine mesylate (e.g., metopimazine mesylate Crystal Form A or metopimazine mesylate Crystal Form B) as described herein, the composition is suitable for administration of more than 20 mg of the crystalline form of metopimazine mesylate (e.g., metopimazine mesylate Crystal Form A or metopimazine mesylate Crystal Form B) per day. In certain embodiments of any of the pharmaceutical compositions comprising a crystalline form of metopimazine mesylate (e.g., metopimazine mesylate Crystal Form A or metopimazine mesylate Crystal Form B) as described herein, the composition is suitable for administration of more than 30 mg of the crystalline form of metopimazine mesylate (e.g., metopimazine mesylate Crystal Form A or metopimazine mesylate Crystal Form B) per day.

The present application provides a method of treating an enteric nervous system disorder in a human subject in need thereof, comprising administering to the subject a pharmaceutical composition comprising a crystalline form of metopimazine mesylate (e.g., metopimazine mesylate Crystal Form A or metopimazine mesylate Crystal Form B) as disclosed herein. In certain embodiments, the enteric nervous system disorder is a chronic disorder. In certain embodiments, the enteric nervous system disorder is an acute disorder. In certain embodiments, the enteric nervous system disorder is selected from the group consisting of gastroparesis, Irritable Bowel Syndrome, lysosomal storage disorders, intestinal dysmotility, ganglioneuroma, multiple endocrine neoplasia type 2B (MEN2B), gastrointestinal neuropathy, functional dyspepsia, gastroesophageal reflux disease (GERD), and intestinal neuronal dysplasia.

In certain embodiments, the enteric nervous system disorder comprises a symptom selected from the group consisting of early satiety, post-prandial fullness, abdominal fullness, nausea, vomiting, delayed gastric emptying, diarrhea, abdominal pain, gas, bloating, gastroesophageal reflux, reduced appetite, and constipation. In certain embodiments, the enteric nervous system disorder symptom comprises nausea. In certain embodiments, the enteric nervous system disorder symptom comprises vomiting.

The present application provides a method of treating gastroparesis in a human subject in need thereof, comprising administering to the subject a pharmaceutical composition comprising a crystalline form of metopimazine mesylate (e.g., metopimazine mesylate Crystal Form A or metopimazine mesylate Crystal Form B) as disclosed herein. In certain embodiments, the gastroparesis is diabetic gastroparesis. In certain embodiments, the gastroparesis is idiopathic gastroparesis. In certain embodiments, the gastroparesis comprises a symptom selected from the group consisting of early satiety, post-prandial fullness, abdominal fullness, nausea, vomiting, delayed gastric emptying, diarrhea, abdominal pain, gas, bloating, gastroesophageal reflux, reduced appetite, and constipation. In certain embodiments, the gastroparesis symptom comprises nausea. In certain embodiments, the gastroparesis symptom comprises vomiting.

The present application provides a method of treating nausea associated with gastroparesis in a human subject in need thereof, comprising administering to the subject a pharmaceutical composition comprising a crystalline form of metopimazine mesylate (e.g., metopimazine mesylate Crystal Form A or metopimazine mesylate Crystal Form B) as disclosed herein.

The present application provides a method of treating vomiting associated with gastroparesis in a human subject in need thereof, comprising administering to the subject a pharmaceutical composition comprising a crystalline form of metopimazine mesylate (e.g., metopimazine mesylate Crystal Form A or metopimazine mesylate Crystal Form B) as disclosed herein.

The present application provides a method of improving gastric emptying in a human subject in need thereof, comprising administering to the subject a pharmaceutical composition comprising a crystalline form of metopimazine mesylate (e.g., metopimazine mesylate Crystal Form A or metopimazine mesylate Crystal Form B) as disclosed herein.

The present application provides a method of treating functional and motility disorders of the GI tract in a human subject in need thereof, comprising administering to the subject a pharmaceutical composition comprising a crystalline form of metopimazine mesylate (e.g., metopimazine mesylate Crystal Form A or metopimazine mesylate Crystal Form B) as disclosed herein.

In certain embodiments of any of the methods disclosed herein, the pharmaceutical composition is administered to the subject chronically. In other embodiments of any of the methods disclosed herein, the pharmaceutical composition is administered to the subject acutely. In certain embodiments of any of the methods disclosed herein, the pharmaceutical composition is administered to the subject for at least 6 days. In certain embodiments of any of the methods disclosed herein, the pharmaceutical composition is administered to the subject for at least 7 days. In certain such embodiments, wherein the pharmaceutical composition is administered to the subject for at least four weeks. In certain further embodiments, wherein the pharmaceutical composition is administered to the subject for at least 12 weeks.

In certain embodiments of any of the methods disclosed herein, the pharmaceutical composition is administered to the subject one time per day. In certain embodiments, the pharmaceutical composition is administered to the subject two times per day. In certain embodiments, the pharmaceutical composition is administered to the subject three times per day. In certain embodiments, the pharmaceutical composition is administered to the subject four times per day.

In certain embodiments of any of the methods disclosed herein, between about 5 mg and about 160 mg of the crystalline form of metopimazine mesylate (e.g., metopimazine mesylate Crystal Form A or metopimazine mesylate Crystal Form B) is administered to the subject per day. In certain embodiments of any of the methods disclosed herein, more than 20 mg of a crystalline form of metopimazine mesylate (e.g., metopimazine mesylate Crystal Form A or metopimazine mesylate Crystal Form B) is administered to the subject per day. In certain embodiments of any of the methods disclosed herein, more than 30 mg of a crystalline form of metopimazine mesylate (e.g., metopimazine mesylate Crystal Form A or metopimazine mesylate Crystal Form B) is administered to the subject per day. In certain embodiments of any of the methods as described herein, between about 5 mg and about 240 mg of the crystalline form of metopimazine mesylate (e.g., metopimazine mesylate Crystal Form A or metopimazine mesylate Crystal Form B) is administered to the subject per day, such as about 5 mg, about 10 mg, about 15 mg, about 20 mg, about 30 mg, about 40 mg, about 50 mg, about 60 mg, about 80 mg, about 90 mg, about 100 mg, about 120 mg, about 150 mg, about 160 mg, about 180 mg, about 200 mg, about 240 mg of the crystalline form of metopimazine mesylate (e.g., metopimazine mesylate Crystal Form A or metopimazine mesylate Crystal Form B) is administered to the subject per day. In certain embodiments of any of the methods disclosed herein, about 5 mg of the crystalline form of metopimazine mesylate (e.g., metopimazine mesylate Crystal Form A or metopimazine mesylate Crystal Form B) is administered to the subject one time, two times, three times, or four times per day. In certain embodiments of any of the methods disclosed herein, about 10 mg, about 15 mg, about 20 mg, about 30 mg, about 40 mg, about 50 mg, or about 60 mg of the crystalline form of metopimazine mesylate (e.g., metopimazine mesylate Crystal Form A or metopimazine mesylate Crystal Form B) is administered to the subject one time, two times, three times, or four times per day. In certain embodiments of any of the methods disclosed herein, about 40 mg of a crystalline form of metopimazine mesylate (e.g., metopimazine mesylate Crystal Form A or metopimazine mesylate Crystal Form B) is administered to the subject four times per day. In certain embodiments of any of the methods disclosed herein, about 60 mg of a crystalline form of metopimazine mesylate (e.g., metopimazine mesylate Crystal Form A or metopimazine mesylate Crystal Form B) is administered to the subject four times per day.

Definitions

As used in the specification and claims, the singular forms "a", "an" and "the" include plural references unless the context clearly dictates otherwise. For example, the term "a cell" includes a plurality of cells, including mixtures thereof.

The term "agonist," as used herein, generally refers to a molecule such as a compound, a drug, an enzyme activator or a hormone modulator that binds to a specific receptor and triggers a response in the cell. An agonist generally mimics the action of an endogenous ligand (such a, e.g., dopamine) that binds to the same receptor.

The term "amorphous," as used herein, refers to solids of disordered arrangements of molecules that do not possess a distinguishable crystal lattice.

The term "antagonist," as used herein, refers to a molecule such as a compound, which diminishes, inhibits, or prevents a cellular response to a receptor activated by an agonist. Antagonists can include, but are not limited to, competitive antagonists, non-competitive antagonists, uncompetitive antagonists, partial agonists and inverse agonists. Competitive antagonists can reversibly bind to receptors at the same binding site (active site) as the endogenous ligand or agonist, without necessarily activating the receptor. Non-competitive antagonists (also known as allosteric antagonists) can bind to a distinctly separate binding site from the agonist, exerting their action to that receptor via another binding site. Non-competitive antagonists generally do not compete with agonists for binding. Binding of a non-competitive antagonist to the receptor may result in a decreased affinity of an agonist to that receptor. Alternatively, binding of a non-competitive antagonist to a receptor may prevent a conformational change in the receptor required for agonist-mediated receptor activation. Uncompetitive antagonists may require receptor activation by an agonist before they can bind to a separate allosteric binding site. Partial agonists can refer to molecules which, at a given receptor, might differ in the amplitude of the functional response that they elicit after maximal receptor occupancy. Although they are agonists, partial agonists can act as a competitive antagonist if co-administered with a full agonist, as it competes with the full agonist for receptor occupancy and producing a net decrease in the receptor activation observed with the full agonist alone. An inverse agonist can have effects similar to an antagonist, but causes a distinct set of downstream biological responses. Constitutively active receptors which exhibit intrinsic or basal activity can have inverse agonists, which not only block the effects of binding agonists like a classical antagonist, but also inhibit the basal activity of the receptor.

As use herein, the term "crystal' or "crystals" or "crystalline' or "crystalinic' refers to any solid that has a short or long range order of the molecules, atoms or ions in a fixed lattice arrangement. Salt Crystals of the Present Invention may be in a single crystal form. Therefore, the Salt Crystals of the Present Invention may be in a triclinic, monoclinic, orthorhombic, tetragonal, rhobohedral, hexagonal or cubic crystal form or mixtures thereof. In particular, the Salt Crystals of the Present Invention are dry crystalline form.

As used herein, "gastrointestinal (GI) tract" refers to portions of the digestive tract where substantial absorption is observed. As one of skill would readily appreciate, substantial absorption is generally observed in the oral cavity, small intestine (e.g., duodenum, jejunum, and ileum), and large intestine (e.g., colon).

As used herein, "metopimazine mesylate" refers to 1-(3-(2-(methylsulfonyl)-10H-phenothiazin-10-yl)propyl)piperidine-4-carboxamide methanesulfonic acid.

As used herein, the "oral cavity" generally refers to the mouth and includes the lips, the lining inside the cheeks and lips, the tongue, the upper and lower gums, the floor of the mouth under the tongue, the sublingual mucosa, the roof of the mouth, and the area behind the wisdom teeth.

As used herein, a compound that is "peripherally restricted" generally refers to a compound that does not substantially cross an intact blood brain barrier of a subject. The term also encompasses compounds that may cross an intact blood brain barrier, but upon administration to a subject is rapidly metabolized to a form that does not substantially cross an intact blood brain barrier of the subject. A compound may be considered "peripherally restricted" if, upon administration to a subject, less than 50%, less than 45%, less than 40%, less than 35%, less than 30%, less than 25%, less than 20%, less than 15%, less than 10%, less than 9%, less than 8%, less than 7%, less than 6%, less than 5%, less than 4%, less than 3%, less than 2%, less than 1%, less than 0.5%, less than 0.1% of the compound crosses an intact blood brain barrier of the subject.

The term "solvate" refers to crystalline solid adducts containing either stoichiometric or nonstoichiometric amounts of a solvent incorporated within the crystal structure. Therefore, the term "non-solvate" form herein refers to salt crystals that are free or substantially free of solvent molecules within the crystal structures of the invention. Similarly, the term "non-hydrate form herein refers to salt crystals that are free or substantially free of water molecules within the crystal structures of the invention.

As used herein, the terms "treatment" or "treating" are used interchangeably herein. These terms refer to an approach for obtaining beneficial or desired results including but not limited to a therapeutic benefit and/or a prophylactic benefit. A therapeutic benefit can mean eradication or amelioration of the underlying disorder being treated. Also, a therapeutic benefit can be achieved with the eradication or amelioration of one or more of the physiological symptoms associated with the underlying disorder such that an improvement is observed in the subject, notwithstanding that the subject may still be afflicted with the underlying disorder. A prophylactic effect includes delaying or eliminating the appearance of a disease or condition, delaying or eliminating the onset of symptoms of a disease or condition, slowing, halting, or reversing the progression of a disease or condition, or any combination thereof. For prophylactic benefit, the compositions may be administered to a subject at risk of developing a particular disease, or to a subject reporting one or more of the physiological symptoms of a disease, even though a diagnosis of this disease may not have been made.

A "sub-therapeutic amount" of an agent is an amount less than the effective amount for that agent. When combined with an effective or sub-therapeutic amount of one or more additional agents, the sub-therapeutic amount can produce a result desired by the physician, due to, for example, synergy in the resulting efficacious effects, or reduced adverse effects.

A "synergistically effective" therapeutic amount or "synergistically effective" amount of an agent or therapy is an amount which, when combined with an effective or sub-therapeutic amount of one or more additional agents, produces a greater effect than when either of the agents are used alone. In some embodiments, a synergistically effective therapeutic amount of an agent or therapy produces a greater effect when used in combination than the additive effects of any of the individual agents when used alone. The term "greater effect" encompasses not only a reduction in symptoms of the disorder to be treated, but also an improved side effect profile, improved tolerability, improved patient compliance, improved efficacy, or any other improved clinical outcome.

The term "co-administration," "administered in combination with," and their grammatical equivalents, as used herein, encompass administration of two or more agents to an animal so that both agents and/or their metabolites are present in the subject at the same time. Co-administration includes simultaneous administration in separate compositions, administration at different times in separate compositions, or administration in a composition in which both agents are present.

The terms "determining", "measuring", "evaluating", "assessing," "assaying," and "analyzing" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

Exemplary Subjects

The pharmaceutical compositions as disclosed herein can be used for the treatment of a disorder in a subject in need thereof. The subject may be suffering from, may be diagnosed with, may be exhibiting a symptom of, or may be suspected of having the disorder. The disorder can be a gastrointestinal disorder, an enteric nervous system disorder, or other disorder. The disorder may be characterized by a hypomotility of at least a portion of the gastrointestinal tract. For example, the disorder can be characterized by hypomotility of the stomach and/or intestine. The hypomotility may be caused by aberrant ENS neuronal signaling, for example, by aberrant dopamine signaling activity.

In some embodiments, the enteric nervous system disorder is gastroparesis. The terms "gastroparesis" and "delayed gastric emptying" are used interchangeably herein to refer to a disorder that, e.g., slows or stops the movement of food from the stomach to the small intestine. Normally, the muscles of the stomach, which are controlled by the vagus nerve, contract to break up food and move it through the gastrointestinal (GI) tract. Gastroparesis can occur, for example, when the vagus nerve is damaged by illness or injury, causing the stomach muscles stop working normally. In subjects with gastroparesis, food can move slowly from the stomach to the small intestine or may stop moving altogether. Accordingly, the subject may be suffering from, may be diagnosed with, may be exhibiting a symptom of, or may be suspected of having gastroparesis.

A subject may be suspected of having gastroparesis if the subject exhibits or has exhibited a symptom of gastroparesis. Symptoms of gastroparesis can include gastroesophageal reflux (GER), also called acid reflux or acid regurgitation. Gastroesophageal reflux generally refers to a condition in which stomach contents flow back up into the esophagus. Other symptoms associated with gastroparesis include, but are not limited to, early satiety, postprandial fullness, abdominal fullness, abdominal pain and/or burning sensation in the stomach area, abdominal bloating, lack of appetite, anorexia, malnutrition, nausea, and vomiting. A symptom of gastroparesis can be mild, moderate or severe, and can occur frequently or infrequently. A symptom of gastroparesis can vary in severity over time in the same subject. Accordingly, the subject may exhibit or has exhibited GER, early satiety, postprandial fullness, abdominal fullness, abdominal pain and/or burning sensation in the stomach area, abdominal bloating, lack of appetite, anorexia, malnutrition, nausea, and/or vomiting.

The subject may be diagnosed with gastroparesis. Gastroparesis may be diagnosed by any means known to those of skill in the art or otherwise described herein. Gastroparesis may be diagnosed, e.g., through a physical exam, medical history, blood tests, tests to rule out blockage or structural problems in the GI tract, gastric emptying assays, and assays of GI contractile activity. Tests may also identify a nutritional disorder or underlying disease. Tests that are useful in diagnosing gastroparesis include, but are not limited to, upper gastrointestinal (GI) endoscopy, upper GI series, ultrasound tests, gastric emptying scintigraphy, gastric emptying breath test, antral manometry, electrogastrography, and/or electrogastroenterography.

Upper GI endoscopy can be used to rule out other conditions that could result in delayed gastric emptying (such as, e.g., a physical obstruction). Upper GI endoscopy typically involves use of an endoscope (e.g., a small, flexible tube with a light) to visualize the upper GI tract, including, e.g., the esophagus, stomach, and duodenum (the first part of the small intestine). The endoscope is generally used to image the stomach and/or duodenum. A small camera mounted on the endoscope can transmit a video image to a monitor, allowing close examination of the intestinal lining. Upper GI endoscopy may show physical blockage of the upper GI tract, for example, a large bezoar (e.g., solid collections of food, mucus, vegetable fiber, hair, or other material). In some embodiments, the subject is diagnosed with gastroparesis if the subject exhibits a symptom of gastroparesis and upper GI endoscopy does not reveal a physical blockage causing the delayed gastric emptying.

An upper GI series may be performed to look at the small intestine. The test may be performed at a hospital or outpatient center by an x-ray technician, and the images may be interpreted by a radiologist. During the procedure, the subject may stand or sit in front of an x-ray machine and drink barium, a chalky liquid. Barium may coat the small intestine, making signs of gastroparesis show up more clearly on x rays. Gastroparesis may be indicated in cases wherein the x-ray shows food in the stomach after fasting. In some embodiments, the subject is diagnosed with gastroparesis if an upper GI series reveals food in the stomach after fasting.

Ultrasound can be useful in ruling out other syndromes which may share symptoms in common with gastroparesis. Such other syndromes include gallbladder disease and pancreatitis. Ultrasound generally uses a device, called a transducer, that bounces safe, painless sound waves off organs to create an image of their structure. The procedure can be performed in a health care provider's office, outpatient center, or hospital by a specially trained technician. Ultrasound images may be interpreted by a radiologist. The subject may be diagnosed with gastroparesis if the subject exhibits a symptom of gastroparesis and other syndromes such as, e.g., gallbladder disease, pancreatitis, are ruled out by, for example, ultrasound.

Gastric emptying scintigraphy can be used to diagnose gastroparesis in a subject. Gastric emptying scintigraphy can involve ingestion of a bland meal—such as eggs or an egg substitute—that contains a small amount of radioactive material. The radioactive material may be 99-M Technetium (TC) sulfur colloid or other radioactive ligand. The test may be performed in a radiology center or hospital. An external camera may be used to detect and/or measure radioactivity in the abdominal region. Radioactivity may be measured at timed intervals, e.g., at 1, 2, 3, and 4 hours after the meal. Gastroparesis may be positively identified in subjects exhibiting more than 10 percent of the meal within the stomach at 4 hours. Other measures of gastric emptying include, but are not limited to, the time at which 50% of the meal has been emptied out of the stomach. See, e.g., Thomforde, G. M. et al., Evaluation of an inexpensive screening scintigraphic test of gastric emptying, 36 J. Nucl. Med. 93 (1995), hereby incorporated by reference. In some embodiments, the subject is diagnosed with gastroparesis via gastric emptying scintigraphy.

A breath test useful for assessing gastric emptying can utilize radioactively labeled food (e.g., labeled with $C^{13}$-octanoic acid). $C^{13}$ from the food may be absorbed when it reaches the small bowel. The absorbed $C^{13}$ can then be rapidly metabolized in the liver to produce $^{13}CO_2$. The produced $^{13}CO_2$ may then be detected in the breath of the subject. The subject's breath may be collected and sampled at defined intervals. The samples may be analyzed for $^{13}CO_2$ by any means known in the art. The rate of appearance of $^{13}CO_2$ in the breath can be used to indicate the rate of gastric emptying. An exemplary method of performing a $C^{13}$-octanoic acid breath test is described in Ghoos, Y. S., et al., 104 Gastroenterology 1640-1647 (1993), hereby incorporated by reference. In some embodiments, the subject is diagnosed with gastroparesis via a breath test.

Manometry generally refers to the assessment of pressure changes in a lumen. Antral manometry, which can also be referred to as antro-duodenal manometry, generally refers to techniques for the evaluation of contractile activity in the distal stomach and duodenum. Intraluminal pressure of the stomach and/or duodenum can be measured through pressure sensors which are introduced into the lumen via a catheter. Measurements may be recorded over time in order to assess intraluminal pressure changes. Recordings may last for any amount of time. Intraluminal pressure changes can be used to indicate contractile patterns in the stomach and/or duodenum. Intraluminal pressure changes may be measured in a fasting state and/or after ingestion of a meal (post-prandially). Post-prandial contractile hypomotility can be indicative of gastroparesis in a subject. Accordingly, a subject may exhibit post-prandial gastric hypomotility, as determined by manometry.

Electrogastrography generally refers to techniques and methods for recording electrical activity of the stomach. Likewise, electrogastroenterography refers to techniques and methods for recording electrical activity of the stomach and small intestine. Such electrical activity can be recorded from the gastrointestinal mucosa, serosa, or the outer skin surface (cutaneously). Gastrointestinal mucosa can refer to the mucous membrane layer of the GI tract. Gastrointestinal serosa can comprise a thin layer of cells which secrete serous fluid, and a thin epithelial layer. Recordings can be made during a fasting state, and after ingestion of a meal (usually 60 minutes). Deviations from the normal frequency of electrical activity can include bradygastria and/or tachygastria. Control subjects typically exhibit an increase in electrical activity after a meal, indicative of increased GI motility. Subjects with aberrant GI motility can exhibit abnormal rhythms in activity and/or impairments in the postprandial increase. A normal frequency of GI electrical activity can be, e.g., 3 cycles per minute. Bradygastria, which can be characterized as a frequency of GI electrical activity that is decreased from normal, e.g., that is less than 2 cycles per minute for at least one minute, can be indicative of gastroparesis. In some embodiments, a subject may exhibit bradygastria. Electrogastrography (EGG) which measures electrical activity with cutaneous electrodes similar to those used in electrocardiograms can also be used to diagnose gastroparesis. (Stern, R. N. et al. EGG: Common issues in validation and methodology, 24 Psychophysiology 55-64 (1987)), hereby incorporated by reference. Accordingly, a subject may be diagnosed with gastroparesis as determined by electrogastrography.

The subject may be suffering from, may be diagnosed with, may be exhibiting a symptom of, or may be suspected of having gastroesophageal reflux disease (GERD). GERD can be a chronic condition resulting in gastroesophageal reflux. Symptoms of GERD include, e.g., heartburn, dry, chronic cough, wheezing, asthma, recurrent pneumonia, nausea, vomiting, sore throat, difficulty swallowing, pain in the chest or upper abdomen, dental erosion, bad breath, spitting up. GERD may be diagnosed with the aid of tests. Tests that are useful in the diagnosis of GERD include, e.g., upper GI series, described herein, upper endoscopy, esophageal pH monitoring, and esophageal manometry.

The subject may be suffering from, may be diagnosed with, may be exhibiting a symptom of, or may be suspected of having enteric nervous system disorder which is associated with a vestibular disorder of the ear. The vestibular disorder of the ear can be Menetrier's disease. Ménétrier's disease can be characterized by enlargement of ridges (also referred to herein as rugae) along the inside of the stomach wall, forming giant folds in the lining of the stomach. Ménétrier disease may also cause a decrease in stomach acid resulting from a reduction in acid-producing parietal cells. Symptoms of Ménétrier disease include, by way of example only, severe stomach pain, nausea, frequent vomiting, and the like.

The subject may be suffering from, may be diagnosed with, may be exhibiting a symptom of, or may be suspected of having cyclical vomiting syndrome (CVS). Cyclical vomiting syndrome can be characterized by episodes or cycles of severe nausea and vomiting that alternate with symptom-free intervals. Such episodes can last for hours, or even days. Episodes can start at the same time of day, can last the same length of time, and can occur with the same symptoms and level of intensity. Episodes can be so severe that a person has to stay in bed for days, unable to go to school or work. Other symptoms of cyclical vomiting syndrome include, e.g., abdominal pain, diarrhea, fever, dizziness, and sensitivity to light during vomiting episodes. Continued vomiting may cause severe dehydration that can be life threatening. Symptoms of dehydration include thirst, decreased. Cyclical vomiting syndrome may be diagnosed in a subject who has experienced the following symptoms for at least 3 months: vomiting episodes that start with severe vomiting—several times per hour—and last less than 1 week, three or more separate episodes of vomiting in the past year, and absence of nausea or vomiting between episodes.

The subject may be suffering from, may be diagnosed with, may be exhibiting a symptom of, or may be suspected of having Irritable Bowel Syndrome (IBS). IBS generally refers to a syndrome in which subjects experience recurrent or chronic gastrointestinal symptoms. Symptoms of IBS can include, e.g., abdominal pain, abdominal discomfort, constipation, diarrhea, mucus in the stool, abdominal bloating, or a combination of any of the above. IBS may be diagnosed when a person has had abdominal pain or discomfort at least three times a month for the last 3 months without other disease or injury that could explain the pain. The pain or discomfort of IBS may occur with a change in stool frequency or consistency or be relieved by a bowel movement. IBS can be classified into four subtypes based on a subject's usual stool consistency. The four subtypes of IBS are: IBS with constipation (IBS-C), IBS with diarrhea (IBS-D), mixed IBS (IBS-M), and unsubtyped IBS (IBS-U). A subject with IBS-C may have hard or lumpy stools at least 25 percent of the time, may have loose or watery stools less than 25 percent of the time, or a combination of the two. A subject with IBS-D may have loose or watery stools at least 25 percent of the time, hard or lumpy stools less than 25 percent of the time, or a combination of the two. A subject with IBS-M may have hard or lumpy stools at least 25 percent of the time and loose or watery stools at least 25 percent of the time. A subject with IBS-U may have hard or lumpy stools less than 25 percent of the time, loose or watery stools less than 25 percent of the time, or a combination of the two. Constipation associated with IBS may be due to slow or delayed gastric motility. In some embodiments, the subject with IBS has experienced constipation. IBS can be diagnosed in a subject by any means known in the art or otherwise described herein. For instance, IBS may be diagnosed by a health care provider. The health care provider may conduct a physical exam and may take a medical history of the subject. IBS may be diagnosed if a subject has exhibited one or more symptoms of IBS for at least 3, 4, 5, or 6 months, with one or more symptoms occurring at least three times a month for the previous 3 months. Additional tests that may be useful in the diagnosis of IBS include, but are not limited to: a stool test, lower GI series, flexible sigmoidoscopy, or colonoscopy.

The subject may be suffering from, may be diagnosed with, may be exhibiting a symptom of, or may be suspected of having functional dyspepsia (e.g., impaired digestion). Symptoms of dyspepsia include but are not limited to, e.g., chronic or recurrent pain in the upper abdomen, upper abdominal fullness, postprandial fullness, early satiety, bloating, belching, nausea, vomiting, heartburn, sour taste in the mouth. Functional dyspepsia (e.g., nonulcer dyspepsia) generally refers to dyspepsia without evidence of an organic disease that is likely to explain the symptoms of dyspepsia. An example of functional dyspepsia is dyspepsia in the absence of an ulcer. Functional dyspepsia is estimated to affect about 15% of the general population in western countries. Other exemplary ENS disorders include but are not limited to, e.g., intestinal dysmotility, ganglioneruoma, multiple endocrine neoplasia type 2B (MEN2B), gastrointestinal neuropathy, and intestinal neuronal dysplasia.

The subject may be suffering from, may be diagnosed with, may be exhibiting a symptom of, or may be suspected of having an enteric nervous system disorder caused by another underlying disease. For example, the enteric nervous system disorder can be a Parkinson's disease-induced ENS disorder. Parkinson's disease-induced ENS disorder can be related to degeneration of dopamine ENS neurons. Symptoms of a Parkinson's disease-induced ENS disorder include, e.g., constipation, nausea, vomiting, and the like. In some embodiments, a subject to be treated according to a method of the application is diagnosed with, suffering a symptom of, is suspected of having, Parkinson's disease, and further exhibits a symptom of an ENS disorder as described herein.

The subject may be suffering from, may be diagnosed with, may be exhibiting a symptom of, or may be suspected of having an enteric nervous system disorder can associated with scleroderma. Scleroderma can be characterized by hardening and tightening of the skin and connective tissues. In some embodiments, the subject is suffering from, may be diagnosed with, may be exhibiting a symptom of, or may be suspected of having gastroparesis associated with Scleroderma The subject may be suffering from, may be diagnosed with, may be exhibiting a symptom of, or may be suspected of having a diabetes-associated enteric nervous system disorder. The diabetes-associated enteric nervous system disorder can be a diabetes-associated gastroparesis. The subject may be suffering from, may be diagnosed with, may be exhibiting a symptom of, or may be suspected of having an enteric nervous system disorder associated with multiple sclerosis.

Other diseases and clinical conditions that can cause an enteric nervous system disorder such as gastroparesis include, e.g., cancer, hypothyroidism, hyperthyroidism, hyperparathyroidism, adrenal insufficiency (Addison's disease), gastric ulcer, gastritis, post-gastric surgery, such as, e.g., vagotomy (resection of the vagus nerve), antrectomy (resection of a portion of the stomach distal to the antrum of the stomach), subtotal gastrectomy (resection of a gastric tumor), gastrojejunostomy (a surgical procedure that connects two lumens of the GI tract, such as a proximal segment of stomach and a segment of the small intestine), fundoplication (a surgical procedure that wraps an upper portion of the stomach around a lower end of the esophagus), polymyositis (a persistent inflammatory muscle disease that can cause muscle weakness), muscular dystrophy (a disease that can cause progressive muscle weakness), amyloidosis (characterized by buildup of amyloid in a tissue or organ of the subject, such as in the gastrointestinal tract), intestinal pseudo-obstruction (a condition that causes symptoms that are associated with bowel obstruction but wherein no bowel obstruction is found), dermatomyositis (a disease characterized by muscular inflammation), systemic lupus erythematosus (a systemic autoimmune disease that can affect various tissues of the body, including the nervous system), eating disorders such as, e.g., anorexia and bulimia, depression, paraneoplastic syndrome, and high cervical cord lesions (e.g., lesions at spinal cord C4 or above).

The subject can be suffering a symptom of an enteric nervous system disorder. Exemplary symptoms are described herein. In some embodiments, the symptom is nausea and/or vomiting. In some embodiments, the cause of the symptom is unknown (e.g., unexplained nausea). In some embodiments, the symptom is a chronic or recurrent symptom. The subject may, for example, experience the symptom for at least 3 days, at least 5 days, at least 1 week, at least 2 weeks, at least 4 weeks, at least 1 month, at least 2 months, at least 3 months, at least 4 months, at least 5 months, at least 6 months, at least 7 months, at least 8 months, at least 9 months, at least 10 months, at least 11 months, at least 12 months (1 year), at least 1.5 years, at least 2 years, at least 3 years, at least 4 years, at least 5 years, at least 6 years, at least 7 years, at least 8 years, at least 9 years, or at least 10 years. The subject may experience the symptom 1, 2, 3, 4, 5, 6, 7, 8, 8, 10, 11, 12, 13, 14, 15, 16, 17, 18, 19, 20, 21, 22, 23, 24, 25, 26, 27, 28, 29, 30, 31, or more than 31 times a month.

The subject may be, e.g., a mouse, a rat, a hamster, a gerbil, a dog, a cat, a primates such as, e.g., a monkey or human. In some embodiments, the subject is a human. The subject may be an adult, a child, or an infant. The subject can be of any age.

Use of the Pharmaceutical Compositions

Pharmaceutical compositions as described herein can be safely administered to a subject. Pharmaceutical compositions as described herein can be administered without necessarily increasing risk of developing a deleterious cardiac side effect. For example, pharmaceutical compositions described herein may not increase risk of modulating cardiac action potential, and/or may not increase risk of inducing long QT syndrome, and/or may not increase risk of cardiac arrest, and/or may not increases risk of sudden death by cardiac arrest.

The subject may be safely administered an effective amount of a pharmaceutical composition as described herein for an unlimited amount of time. The subject may be safely administered an effective amount of the pharmaceutical composition acutely or chronically. For example, the subject may be safely administered an effective amount of the pharmaceutical composition once, for one day, for at least 2 days, for at least 3 days, for at least four days, for five days, for at least five days, for at least six days, for at least seven days (1 week), for at least 2 weeks, for at least 3 weeks, for at least 4 weeks, for at least 5 weeks, for at least 6 weeks, for at least 7 weeks, for at least 8 weeks, for at least 9 weeks, for at least 10 weeks, for at least 11 weeks, for at least 12 weeks, for at least 3 months, for at least 4 months, for at least 5 months, for at least 6 months, for at least 7 months, for at least 8 months, for at least 9 months, for at least 10 months, for at least 11 months, for at least 12 months (1 year), for at least 2 years, for at least 5 years, or for at least a decade.

Administration of a pharmaceutical composition as described herein may confer an acceptable risk that the subject will develop an unwanted cardiac side effect. Risk of pharmaceutical composition administration on developing such unwanted cardiac side effect can be determined by any means known in the art, or as described herein. For example, risk can be determined by comparing the incidence of sudden death in a population of subjects administered the pharmaceutical composition as compared to incidence of sudden death in a population of control subjects that have not been administered the pharmaceutical composition. Risk can be determined by tracking the number of subjects administered the pharmaceutical composition who experienced the unwanted cardiac side effect, and the number of subjects administered the pharmaceutical composition who did not experience the unwanted cardiac side effect. For example, if a=the number of subjects administered the pharmaceutical composition who experienced the unwanted cardiac side effect, and b=the number of subjects administered the pharmaceutical composition who did not experience the unwanted cardiac side effect, the risk of experiencing the unwanted cardiac side effect conferred by being administered the pharmaceutical composition can be calculated as a/(a+b). Relative risk (RR) may be used to compare the risk of developing an unwanted cardiac side effect conferred by administration of the pharmaceutical composition to the risk of developing the unwanted cardiac side effect in a population of subjects that have not been administered the pharmaceutical composition. For example, if a=the number of subjects administered the pharmaceutical composition who experienced the unwanted cardiac side effect, b=the number of subjects administered the pharmaceutical composition who did not experience the unwanted cardiac side effect, c=the number of subjects not administered the pharmaceutical composition who experienced the unwanted cardiac side effect, and d=the number of subjects not administered the pharmaceutical composition who did not experience the unwanted cardiac side effect, RR conferred by administration of the pharmaceutical composition can be calculated as a/(a+b)/(c/(c+d). For other example, risk can be determined by calculating an odds ratio.

The RR of administration of a pharmaceutical composition as described herein with sudden cardiac death can be less than 3.8, less than 3.7, less than 3.6, less than 3.5, less than 3.4, less than 3.3, less than 3.2, less than 3.1, less than 3.0, less than 2.9, less than 2.8, less than 2.7, less than 2.6, less than 2.5, less than 2.4, less than 2.3, less than 2.2, less than 2.1, less than 2.0, less than 1.9, less than 1.8, less than 1.7, less than 1.6, less than 1.5, less than 1.4, less than 1.3, less than 1.2, less than 1.1, less than 1.05, about 1, or less than 1.

The odds ratio of administration of a pharmaceutical composition described herein with sudden cardiac death can be an acceptable odds ratio. The term odds ratio (OR) generally refers to a measure of association between an exposure (e.g., exposure to a drug) and an outcome (e.g., sudden cardiac death). The OR can represent the odds that the outcome will occur given a particular exposure, as compared to the odds of the outcome occurring in the absence of that exposure. Odds ratios can be used in case-control studies, as well as in cross-sectional and cohort study design studies. For example, if a=the number of subjects administered the pharmaceutical composition who experienced the unwanted cardiac side effect, b=the number of subjects administered the pharmaceutical composition who did not experience the unwanted cardiac side effect, c=the number of subjects not administered the pharmaceutical composition who experienced the unwanted cardiac side effect, and d=the number of subjects not administered the pharmaceutical composition who did not experience the unwanted cardiac side effect, OR conferred by administration of the pharmaceutical composition can be calculated as ad/bc.

The OR of administration of a pharmaceutical composition described herein with sudden cardiac death can be less than 3.8, less than 3.7, less than 3.6, less than 3.5, less than 3.4, less than 3.3, less than 3.2, less than 3.1, less than 3.0, less than 2.9, less than 2.8, less than 2.7, less than 2.6, less than 2.5, less than 2.4, less than 2.3, less than 2.2, less than 2.1, less than 2.0, less than 1.9, less than 1.8, less than 1.7, less than 1.6, less than 1.5, less than 1.4, less than 1.3, less than 1.2, less than 1.1, less than 1.05, about 1, or less than 1.

Unlike other dopamine modulating drugs previously indicated for the treatment of ENS, the pharmaceutical compositions described herein for use in the treatment of ENS are peripherally restricted. Accordingly, such pharmaceutical compositions can be safely administered to a subject without increasing risk in the subject for developing motor-related dysfunction mediated by brain dopaminergic signaling. For example, such pharmaceutical compositions can be safely administered to a subject without increasing risk in the subject for developing an extrapyramidal side effect. Exemplary extrapyramidal side effects include, e.g., tardive dyskinesia (involuntary asymmetrical movements of the muscles), dystonia (characterized by sustained muscle contractions), akinesia (lack of movement), akathisia (feeling of motor restlessness), bradykinesia (slowed movements), stiffness, and tremor, twisting and/or repetitive movements, abnormal postures, muscle spasms, e.g., muscle spasms of the neck (torticullis), muscle spasms of the eyes (oculogyric crisis) tongue spasms, spasms of the jaw, and the like. Extrapyramidal symptoms can be assessed by any means known in the art or otherwise described herein. For example, extrapyramidal symptoms may be assessed using the Simpson-Angus Scale (SAS) and/or the Barnes Akathisia Rating Scale (BARS). In some embodiments the odds ratio of administration of the pharmaceutical compositions described herein for use in treating an enteric nervous system disorder with incidence of an extrapyramidal side effect is less than 4, less than 3.9, less than 3.8, less than 3.7, less than 3.6, less than 3.5, less than 3.4, less than 3.3, less than 3.2, less than 3.1, less than 3.0, less than 2.9, less than 2.8, less than 2.7, less than 2.6, less than 2.5, less than 2.4, less than 2.3, less than 2.2, less than 2.1, less than 2.0, less than 1.9, less than 1.8, less than 1.7, less than 1.6, less than 1.5, less than 1.4, less than 1.3, less than 1.2, less than 1.1, less than 1.05, about 1, or less than 1.

The pharmaceutical compositions of the application can promote gastric motility upon administration to the subject. Such pharmaceutical compositions may promote gastric motility by, for example, reducing dopamine $D_2$-receptor mediated signaling in an enteric neuron of the subject. For example, the pharmaceutical compositions can antagonize dopamine $D_2$ receptors in an enteric neuron of the subject. For other example, the pharmaceutical compositions may reduce the dopaminergic neurotransmission of an enteric neuron.

Gastric motility can be assessed by any means known to those of skill in the art or otherwise described herein. For example, gastric motility can be assessed by antral manometry, or by methods useful in the diagnosis of gastroparesis. Exemplary methods useful in the diagnosis of gastroparesis are described herein.

Administration of the pharmaceutical compositions as described herein can improve gastric motility as compared to a control subject and/or control population. The control subject can be an individual that has not been administered a pharmaceutical composition described herein. A control population can be a plurality of individuals that have not been administered a pharmaceutical composition described herein. The control subject can be a subject that is suffering from, that has been diagnosed with, be suspected of having, or exhibiting a symptom of an ENS disorder, that is not administered a pharmaceutical composition as described herein. The control subject does not necessarily need to be a different individual, but may be the same subject at a time point prior to receiving a dose of a pharmaceutical composition as described herein. The control subject may be the same subject at a time point subsequent to receiving a dose of a pharmaceutical composition as described herein, after a sufficient time has passed such that the pharmaceutical composition is no longer acting in the subject. The control subject can be a different subject. In some embodiments, administration of a the pharmaceutical composition increases gastric motility by at least 25%, 30%, 35%, 40%, 45%, 50%, 55%, 60%, 65%, 70%, 75%, 80%, 85%, 90%, 95%, 100%, or over 100% as compared to a control subject.

In some embodiments, administration of a pharmaceutical composition described herein is effective in treating a symptom of an enteric nervous system disorder in the subject. Exemplary symptoms are described herein. The symptom may be selected from the group consisting of nausea, vomiting, delayed gastric emptying, diarrhea, abdominal pain, gas, bloating, gastroesophageal reflux, reduced appetite, weight loss, and constipation. In particular cases, administration of a pharmaceutical composition described herein reduces nausea in the subject. Administration of a pharmaceutical composition as described herein may reduce severity of any of the symptoms described herein. In some cases, administration of a pharmaceutical composition as described herein reduces symptom severity by 1-5%, 2-10%, 5-20%, 10-30%, 20-50%, 40-70%, 50-80%, 70-90%, 80-95%, 90-100%. In some cases, administration of a pharmaceutical composition as described herein reduces symptom severity by at least 1%, 2%, 3%, 4%, 5%, 6%, 7%, 8%, 9%, 10%, 15%, 20%, 25%, 30%, 35%, 40%, 45%, 50%, 60%, 70%, 80%, 90%, or more than 90%.

Administration of a pharmaceutical composition as described herein may reduce frequency of onset of a symptom. In some cases, administration of a pharmaceutical composition as described herein reduces frequency of symptom onset by 1-5%, 2-10%, 5-20%, 10-30%, 20-50%, 40-70%, 50-80%, 70-90%, 80-95%, 90-100%. In some cases, administration of a pharmaceutical composition as described herein reduces frequency of symptom onset by at least 1%, 2%, 3%, 4%, 5%, 6%, 7%, 8%, 9%, 10%, 15%, 20%, 25%, 30%, 35%, 40%, 45%, 50%, 60%, 70%, 80%, 90%, or more than 90%. In some cases, administration of a pharmaceutical composition as described herein reduces frequency of symptom onset to less than 1 episode a day, less than 1 episode a week, less than 2 episodes a month, less than 1 episode a month, less than 1 episode every 2 months, less than 1 episode every 3 months, less than 1 episode every 4 months, less than 1 episode every 5 months, less than 1 episode every 6 months, less than 1 episode every 7 months, less than 1 episode every 8 months, less than 1 episode every 9 months, less than 1 episode every 10 months, less than 1 episode every 11 months, or less than 1 episode every 12 months (1 year).

hERG channel inhibition can be determined by any means known in the art or otherwise described herein. hERG channel inhibition can be assessed in vitro, for example, by utilizing hERG expressing cultured cells. hERG-expressing cultured cells for the purposes of assessing hERG channel inhibition are available from a number of commercial vendors, such as, e.g., Life Technologies, Cyprotex, and the like. hERG channel inhibition can be assessed by a variety of means known in the art, including, e.g., voltage clamp studies, hERG binding assays, and the like. Voltage clamp studies can employ the use of commercially available high throughput systems. Exemplary high-throughput systems are described in, e.g., U.S. Pat. No. 8,329,009, and US Patent Application Pub. No. 20020164777, which are hereby incorporated by reference. hERG binding assays can include competition and/or saturation binding assays using $^{3H}$dofetilide. Such assays are described in J Pharmacol Toxicol Methods. 2004 November-December; 50(3):187-99, which is hereby incorporated by reference. hERG channel inhibition can be determined by in vivo studies, for example, by assessment of cardiac action potentials in large animal models, e.g., canines.

Minimal hERG inhibition can be evidenced by an $IC_{50}$ that is higher than 0.1 µM, higher than 0.2 µM, higher than 0.3 µM, higher than 0.4 µM, higher than 0.5 µM, higher than 0.6 µM, higher than 0.7 µM, higher than 0.8 µM, higher than 0.9 µM, higher than 1 µM, higher than 2 µM, higher than 3 µM, higher than 4 µM, higher than 5 µM, higher than 6 µM, higher than 7 µM, higher than 8 µM, higher than 9 µM, higher than 10 µM, higher than 15 µM, higher than 20 µM, higher than 30 µM, higher than 40 µM, higher than 50 µM, higher than 60 µM, higher than 70 µM, higher than 80 µM, higher than 90 µM, or higher than 100 µM.

Minimal hERG inhibition can also be evidenced by measuring, at any given dose of a drug, the % inhibition of hERG-mediated tail current. hERG-mediated tail current can be measured by voltage clamp studies, e.g., by patch clamps studies. For example, hERG-mediated tail current can be measured in an hERG-expressing cell prior to contact of the cell with a test agent. hERG-mediated tail current can then be measured in the hERG-expressing cell after contact with a dose of the test agent. The differences between the hERG-mediated tail current before and after administration of the test agent can be used to determine the extent to which the test agent inhibited hERG-mediated tail current. A suitable agent for use in the disclosed methods can, at a 1 µM dose, inhibit hERG-mediated tail current by less than 50%, less than 45%, less than 40%, less than 35%, less than 30%, less than 25%, less than 20%, less than 15%, less than 10%, less than 9%, less than 8%, less than 7%, less than 6%, less than 5%, less than 4%, less than 3%, less than 2%, less than 1%, less than 0.5%, less than 0.4%, less than 0.3%, less than 0.25%, less than 0.2%, less than 0.15%, or less than 0.1%. A suitable agent for use in the disclosed methods can, at a 100 nM dose, inhibit hERG-mediated tail current by less than 20%, less than 15%, less than 10%, less than 9%, less than 8%, less than 7%, less than 6%, less than 5%, less than 4%, less than 3%, less than 2%, less than 1%, less than 0.5%, less than 0.4%, less than 0.3%, less than 0.25%, less than 0.2%, less than 0.15%, or less than 0.1%. In some embodiments, metopimazine can, at a 3 µM dose, inhibit hERG-mediated tail current by less than 50%, less than 45%, less than 40%, less than 35%, less than 30%, less than 25%, less than 20%, less than 15%, less than 10%, less than 9%, less than 8%, less than 7%, less than 6%, less than 5%, less than 4%, less than 3%, less than 2%, less than 1%, less than 0.5%, less than 0.4%, less than 0.3%, less than 0.25%, less than 0.2%, less than 0.15%, or less than 0.1%. In some embodiments, metopimazine acid can, at a 10 µM dose or higher, inhibit hERG-mediated tail current by less than 50%, less than 45%, less than 40%, less than 35%, less than 30%, less than 25%, less than 20%, less than 15%, less than 10%, less than 9%, less than 8%, less than 7%, less than 6%, less than 5%, less than 4%, less than 3%, less than 2%, less than 1%, less than 0.5%, less than 0.4%, less than 0.3%, less than 0.25%, less than 0.2%, less than 0.15%, or less than 0.1%.

Exemplary Pharmaceutical Compositions

Pharmaceutical compositions utilized in the methods of the application may include a pharmaceutically acceptable carrier. The pharmaceutically acceptable carrier for the present compositions may include, but are not limited to, amino acids, peptides, biological polymers, non-biological polymers, simple sugars or starches, inorganic salts, and gums, which may be present singly or in combinations thereof. The peptides used in the acceptable carrier may include, e.g., gelatin and/or albumin. Cellulose or its derivatives may be used in the pharmaceutically acceptable carrier. The sugar used in the acceptable carrier may be lactose and/or glucose. Other useful sugars which may be utilized in the pharmaceutical compositions include but are not limited to, fructose, galactose, lacticol, maltitol, maltose, mannitol, melezitose, myoinositol, palatinate, raffinose, stachyose, sucrose, tehalose, xylitol, hydrates thereof, and combinations of thereof. Binders may be included in the pharmaceutically acceptable carrier. Examples of binders include, but are not limited to, starches (for example, corn starch or potato starch), gelatin; natural or synthetic gums such as acacia, sodium alginate, powdered tragacanth, guar gum, cellulose or cellulose derivatives (for example, methycellulose, ethyl cellulose, cellulose acetate); microcrystalline cellulose, polyvinyl pyrrolidone, and mixtures thereof. Inorganic salts used in the acceptable carrier may be a magnesium salt, for example, magnesium chloride or magnesium sulfate. Other inorganic salts may be used, for example, calcium salts. Examples of calcium salts include, but are not limited to, calcium chloride, calcium sulfate. Other examples of substances which may be used in the pharmaceutically acceptable carrier include, but are not limited to, vegetable oils, such as peanut oil, cottonseed oil, olive oil, corn oil; polyols such as glycerin, propylene glycol, polyethylene glycol; pyrogen-free water, isotonic saline, phosphate buffer solutions; emulsifiers, such as the Tweens®; wetting agents, lubricants, coloring agents, flavoring agents, preservatives.

The term "wetting agents" may be used interchangeably with "surfactants", and refers to substances that lower the surface tension of a liquid, thus allowing the liquid to spread more easily. Surfactant which can be used to form pharmaceutical compositions and dosage forms of the application include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. A useful parameter that may be used to characterize the relative hydrophilicity and hydrophobicity of non-ionic amphiphilic compounds is the hydrophilic-lipophilic balance ("HLB" value). Surfactants with lower HLB values are more hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are generally considered to be compounds having an HLB value equal to or less than about 10. However, HLB value of a surfactant merely provides a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts, fatty acid derivatives of amino acids, glyceride derivatives of amino acids, fusidic acid salts, oligopeptides, and polypeptides, oligopeptides, and polypeptides, lecithins and hydrogenated lecithins, lysolecithins and hydrogenated lysolecithins, phospholipids and derivatives thereof, fatty acid salts, lysophospholipids and derivatives thereof, carnitine fatty acid ester salts, salts of alkylsulfates, sodium docusate, acylactylates, mono- and di-acetylated tartaric acid esters of mono- and di-glycerides, succinylated mono- and di-glycerides, citric acid esters of mono- and di-glycerides, and mixtures thereof.

Within the aforementioned group, ionic surfactants include, but are not limited to, lecithins, lysolecithin, phospholipids, lysophospholipids and derivatives thereof, carnitine fatty acid ester salts, fatty acid salts, salts of alkylsulfates, sodium docusate, acylactylates, mono- and di-acetylated tartaric acid esters of mono- and di-glycerides, succinylated mono- and di-glycerides, citric acid esters of mono- and di-glycerides, and mixtures thereof.

Ionic surfactants may be the ionized forms of lactylic esters of fatty acids, lecithin, lysolecithin, phosphatidylethanolamine, phosphatidylcholine, phosphatidylglycerol, phosphatidic acid, phosphatidylserine, lysophosphatidylcholine, lysophosphatidylserine, lysophosphatidylethanolamine, lysophosphatidylglycerol, lysophosphatidic acid, PEG-phosphatidylethanolamine, PVP-phosphatidylethanolamine, stearoyl-2-lactylate, stearoyl lactylate, succinylated monoglycerides, mono/diacetylated tartaric acid esters of mono/ diglycerides, citric acid esters of mono/diglycerides, cholylsarcosine, caproate, caprylate, caprate, laurate, myristate, palmitate, oleate, linoleate, linolenate, stearate, ricinoleate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides, alkylthioglucosides, alkylmaltosides, lauryl macrogolglycerides, polyoxyalkylene alkyl ethers such as polyethylene glycol alkyl ethers, polyoxyalkylene alkylphenols such as polyethylene glycol alkyl phenols, polyethylene glycol glycerol fatty acid esters, polyoxyalkylene alkyl phenol fatty acid esters such as polyethylene glycol fatty acids monoesters and polyethylene glycol fatty acids diesters, polyglycerol fatty acid esters, polyoxyethylene-polyoxypropylene block copolymers and mixtures thereof, polyoxyalkylene sorbitan fatty acid esters such as polyethylene glycol sorbitan fatty acid esters, hydrophilic transesterification products of a polyol with at least one member of the group consisting of glycerides, vegetable oils, hydrogenated vegetable oils, fatty acids, and sterols, polyoxyethylene sterols and derivatives or analogues thereof, polyoxyethylated vitamins and derivatives thereof, polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-12 oleate, PEG-15 oleate, PEG-20 oleate, PEG-20 laurate, PEG-32 dilaurate, PEG-32 laurate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-20 trioleate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-50 hydrogenated castor oil, PEG-40 castor oil, PEG-35 castor oil, PEG-60 castor oil, PEG-40 palm kernel oil, PEG-40 hydrogenated castor oil, PEG-60 hydrogenated castor oil, PEG-60 corn oil, PEG-6 caprate/ caprylate glycerides, PEG-8 caprate/caprylate glycerides, polyglyceryl-10 laurate, PEG-30 cholesterol, PEG-25 phyto sterol, PEG-30 soya sterol, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, but are not limited to, fatty alcohols, glycerol fatty acid esters, acetylated glycerol fatty acid esters, lower alcohol fatty acids esters, propylene glycol fatty acid esters, sorbitan fatty acid esters, polyethylene glycol sorbitan fatty acid esters, sterols and sterol derivatives, polyoxyethylated sterols and sterol derivatives, polyethylene glycol alkyl ethers, sugar ethers, sugar esters, hydrophobic transesterification products of a polyol with at least one member of the group consisting of glycerides, vegetable oils, hydrogenated vegetable oils, fatty acids and sterols, oil-soluble vitamins/vitamin derivatives, lactic acid derivatives of mono- and di-glycerides, and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

Lubricants that may be used in the pharmaceutical composition include, but are not limited to, agar, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, or mixtures thereof. Additional lubricants include, by way of example, a syloid silica gel, a coagulated aerosol of synthetic silica, or mixtures thereof. A lubricant can optionally be added, in an amount of less than about 1 weight percent of the pharmaceutical composition.

The composition may include one or more pharmaceutically acceptable additives, which may include, but are not limited to, detackifiers, anti-foaming agents, buffering agents, antioxidants, polymers, preservatives, chelating agents, odorants, opacifiers, suspending agents, fillers, plasticizers, and mixtures thereof.

In some embodiments, the pharmaceutically acceptable carrier comprises more than 90%, more than 80%, more than 70%, more than 60%, more than 50%, more than 40%, more than 30%, more than 20%, more than 10%, more than 9%, more than 8%, more than 6%, more than 5%, more than 4%, more than 3%, more than 2%, more than 1%, more than 0.5%, more than 0.4%, more than 0.3%, more than 0.2%, more than 0.1%, more than 0.09%, more than 0.08%, more than 0.07%, more than 0.06%, more than 0.05%, more than 0.04%, more than 0.03%, more than 0.02%, more than 0.01%, more than 0.009%, more than 0.008%, more than 0.007%, more than 0.006%, more than 0.005%, more than 0.004%, more than 0.003%, more than 0.002%, more than 0.001%, more than 0.0009%, more than 0.0008%, more than 0.0007%, more than 0.0006%, more than 0.0005%, more than 0.0004%, more than 0.0003%, more than 0.0002%, or more than 0.0001% of the pharmaceutical composition by w/w, w/v or v/v.

In some embodiments, the concentration of the crystalline form of metopimazine mesylate (e.g., metopimazine mesylate Crystal Form A or metopimazine mesylate Crystal Form B) in the composition comprises less than 100%, less than 90%, less than 80%, less than 70%, less than 60%, less than 50%, less than 40%, less than 30%, less than 20%, less than 10%, less than 9%, less than 8%, less than 6%, less than 5%, less than 4%, less than 3%, less than 2%, less than 1%, less than 0.5%, less than 0.4%, less than 0.3%, less than 0.2%, less than 0.1%, less than 0.09%, less than 0.08%, less than 0.07%, less than 0.06%, less than 0.05%, less than 0.04%, less than 0.03%, less than 0.02%, less than 0.01%, less than 0.009%, less than 0.008%, less than 0.007%, less than 0.006%, less than 0.005%, less than 0.004%, less than 0.003%, less than 0.002%, less than 0.001%, less than 0.0009%, less than 0.0008%, less than 0.0007%, less than 0.0006%, less than 0.0005%, less than 0.0004%, less than 0.0003%, less than 0.0002%, or less than 0.0001% of the pharmaceutical composition by w/w, w/v or v/v.

In some embodiments, the concentration of the crystalline form of metopimazine mesylate (e.g., metopimazine mesylate Crystal Form A or metopimazine mesylate Crystal Form B) is in the range of about 0.0001% to about 50%, about 0.001% to about 40%, about 0.01% to about 20%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12%, about 1% to about 10% of the pharmaceutical composition by w/w, w/v or v/v.

In some embodiments, the concentration of the crystalline form of metopimazine mesylate (e.g., metopimazine mesylate Crystal Form A or metopimazine mesylate Crystal Form B) is in the range of about 0.0001% to about 5%, about 0.001% to about 4%, about 0.01% to about 2%, about 0.02% to about 1%, or about 0.05% to about 0.5% of the pharmaceutical composition by w/w, w/v or v/v.

Described below are some non-limiting examples of pharmaceutical compositions.

Pharmaceutical Compositions for Oral Administration

The pharmaceutical composition comprising an effective amount of a crystalline form of metopimazine mesylate (e.g., metopimazine mesylate Crystal Form A or metopimazine mesylate Crystal Form B) can be formulated for oral administration. In some embodiments, the pharmaceutical composition comprising an effective amount of a crystalline form of metopimazine mesylate (e.g., metopimazine mesylate Crystal Form A or metopimazine mesylate Crystal Form B) for oral administration is a solid pharmaceutical composition. In some embodiments, the solid pharmaceutical composition may be presented as discrete (e.g., unit) oral dosage forms. Non-limiting examples of discrete oral dosage forms include tablets, capsules, caplets, gelatin capsules, sustained release formulations, lozenges, thin films, lollipops, chewing gum. In some embodiments, the discrete oral dosage form is an orally disintegrating oral dosage form, such as, e.g., an orally disintegrating tablet.

Discrete oral dosage forms such as tablets may be coated by known techniques to delay or prolong absorption in the gastrointestinal tract, thus providing a sustained action of a longer period of time. In some embodiments, the crystalline form of metopimazine mesylate (e.g., metopimazine mesylate Crystal Form A or metopimazine mesylate Crystal Form B) is mixed with one or more inert solid diluents, such as calcium carbonate or calcium phosphate. In some embodiments, the crystalline form of metopimazine mesylate (e.g., metopimazine mesylate Crystal Form A or metopimazine mesylate Crystal Form B) is presented as soft gelatin capsules, wherein the crystalline form of metopimazine mesylate (e.g., metopimazine mesylate Crystal Form A or metopimazine mesylate Crystal Form B) is mixed with water or an oil medium, such as peanut oil, or olive oil, for example.

In some embodiments, the pharmaceutical composition comprising an effective amount of a crystalline form of metopimazine mesylate (e.g., metopimazine mesylate Crystal Form A or metopimazine mesylate Crystal Form B) for oral administration is a liquid pharmaceutical composition. Non-limiting examples of liquid compositions for oral administration include hydrophilic suspensions, emulsions, liquids, gels, syrups, slurries, solutions, elixirs, softgels, tinctures, and hydrogels. In some embodiments, solid or liquid compositions comprising an effective amount of a crystalline form of metopimazine mesylate (e.g., metopimazine mesylate Crystal Form A or metopimazine mesylate Crystal Form B) for oral administration comprise various sweetening or flavoring agents, or coloring agents. Examples of coloring agents include dyes suitable for food such as those known as F.D. & C. dyes and natural coloring agents such as grape skin extract, beet red powder, beta carotene, annato, carmine, turmeric, paprika, and so forth.

Derivatives, analogues, and isomers of any of the above colored compound also may be used.

Such dosage forms may be prepared by methods well known to those skilled in the art, e.g., in a pharmacy. Such methods would comprise bringing the crystalline form of metopimazine mesylate (e.g., metopimazine mesylate Crystal Form A or metopimazine mesylate Crystal Form B) into association with the pharmaceutically acceptable carrier.

This application further encompasses anhydrous pharmaceutical compositions and dosage forms comprising an effective amount of a crystalline form of metopimazine mesylate (e.g., metopimazine mesylate Crystal Form A or metopimazine mesylate Crystal Form B), since water may facilitate the degradation of the crystalline form of metopimazine mesylate (e.g., metopimazine mesylate Crystal Form A or metopimazine mesylate Crystal Form B). In some embodiments, the anhydrous pharmaceutical compositions and dosage forms of the application are prepared using anhydrous or low moisture containing ingredients. In some embodiments, the anhydrous pharmaceutical compositions and dosage forms of the application are prepared under low humidity or low moisture conditions. The pharmaceutical compositions of the present application which contain lactose may be made anhydrous if substantial contact with moisture and/or humidity during manufacturing, packaging, and/or storage is expected. An anhydrous pharmaceutical composition comprising an effective amount of a crystalline form of metopimazine mesylate (e.g., metopimazine mesylate Crystal Form A or metopimazine mesylate Crystal Form B) may be prepared and stored such that its anhydrous nature is maintained. For example, the anhydrous compositions may be packaged using materials known to prevent exposure to water such that they can be included in suitable formulary kits, examples of which include, but are not limited to, hermetically sealed foils, plastic or the like, unit dose containers, blister packs, and strip packs.

Pharmaceutical Compositions for Injection or Parenteral Administration

In some embodiments, the pharmaceutical composition is formulated for parenteral administration. "Parenteral administration" generally refers to routes of administration other than the gastro-intestinal tract. Examples of parenteral administration include, but are not limited to, intravenous injection, intra-arterial injection, intrathecal injection (into the spinal cord), intratonsillary injection, subcutaneous injection, intramuscular injection, infusion, or implantation. Infusion may be intradermal, or subcutaneous, or through a transdermal implant. Exemplary pharmaceutical compositions for parenteral administration are disclosed in the following references which are hereby incorporated by reference: U.S. Patent Application Pub. No 2006/0287221, U.S. Pat. Nos. 5,244,925, 4,309,421, 4,158,707, and 5,164,405, all of which are hereby incorporated by reference.

Compositions formulated for parenteral administration may include aqueous solutions and/or buffers commonly used for injection and/or infusion. Commonly used aqueous buffers and/or solutions may include, but are not limited to sodium chloride solutions of about 0.9%, phosphate buffers, Lactated Ringer's solution, Acetated ringer's solution, phosphate buffered saline, citrate buffers, Tris buffers, histidine buffers, HEPES buffers, glycine buffers, N-glycylglycine buffers, and the like. Other pharmaceutically acceptable carriers for parenteral administration may include ethanol, glycerol, propylene glycol, cyclodextrin and cyclodextrin derivatives, vegetable oils, and the like.

In some embodiments, pharmaceutical compositions for injection and/or infusion contain preservatives present in amounts that effectively prevent or reduce microbial contamination or degradation. Various agents, e.g., phenol, m-cresol, benzyl alcohol, parabens, chlorobutanol, methotrexate, sorbic acid, thimerosol, ethyl hydroxybenzoate, bismuth tribromophenate, methyl hydroxybenzoate, bacitracin, propyl hydroxybenzoate, erythromycin, 5-fluorouracil, doxorubicin, mitoxantrone, rifamycin, chlorocresol, benzalkonium chlorides, may be used to prevent or reduce contamination.

In some embodiments, sterile solutions are prepared by incorporating a crystalline form of metopimazine mesylate (e.g., metopimazine mesylate Crystal Form A or metopimazine mesylate Crystal Form B) in the required amount in the appropriate solvent with various other ingredients as described herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain methods of preparation include but are not limited to vacuum-drying and freeze-drying techniques which yield a powder of the active ingredient plus any additional desired ingredient from a previously sterile-filtered solution thereof.

In some embodiments, the pharmaceutical composition is formulated for topical and/or transdermal delivery. Compositions of the present application can be formulated into preparations in liquid, semi-solid, or solid forms suitable for local or topical administration. Examples of forms suitable for topical or local administration include but are not limited to, gels, water soluble jellies, creams, lotions, suspensions, foams, powders, slurries, ointments, oils, pastes, suppositories, solutions, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical composition may comprise suitable solid or gel phase carriers, which are compounds that allow increased penetration of, or assist in the delivery of, therapeutic molecules across the stratum corneum barrier of the skin. There are many of these penetration-enhancing molecules known to those skilled in the art of topical formulation. Examples of such carriers and excipients include, but are not limited to, alcohols (e.g., ethanol), fatty acids (e.g., oleic acid), humectants (e.g., urea), glycols (e.g., propylene glycol), surfactants (e.g., isopropyl myristate and sodium lauryl sulfate), glycerol monolaurate, sulfoxides, pyrrolidones, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present application employs transdermal delivery devices ("patches"). Such transdermal patches may be used to provide continuous or discontinuous infusion of a crystalline form of metopimazine mesylate (e.g., metopimazine mesylate Crystal Form A or metopimazine mesylate Crystal Form B) as described herein in controlled amounts, either with or without an additional agent. The construction and use of transdermal patches for the delivery of pharmaceutical agents is well known in the art. See, e.g., U.S. Pat. Nos. 5,023,252; 4,992,445; and 5,001,139; which are herein incorporated by reference.

In some embodiments, the application provides a pharmaceutical composition comprising an effective amount of a crystalline form of metopimazine mesylate (e.g., metopimazine mesylate Crystal Form A or metopimazine mesylate Crystal Form B) as described herein for transdermal delivery, and a pharmaceutical excipient suitable for delivery by inhalation. Compositions for inhalation include solutions and suspensions in pharmaceutically acceptable, aqueous or organic solvents, or mixtures thereof, and powders. The liquid or solid compositions may contain suitable pharmaceutically acceptable excipients as described herein. The compositions may be administered by the oral or nasal respiratory route for systemic effect. In some embodiments, compositions in preferably pharmaceutically acceptable solvents may be nebulized by use of inert gases. In some embodiments, nebulized solutions may be inhaled directly from the nebulizing device. In other embodiments, nebulizing device may be attached to a face mask tent or intermittent positive pressure breathing machine. Solution, suspension, or powder compositions may be administered, preferably orally or nasally, from devices that deliver the formulation in an appropriate manner.

Other Pharmaceutical Compositions

The pharmaceutical compositions employed in the present application may be formulated for intraocular (ophthalmic), rectal, sublingual, buccal, or intranasal (e.g., intrapulmonary) administration. Formulations suitable for intraocular administration include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w. Formulations suitable for sublingual administration, typically are formulated to dissolve rapidly upon placement in the mouth, allowing the active ingredient to be absorbed via blood vessels under the tongue. Exemplary sublingual formulations include, e.g., lozenges comprising the active ingredient in a flavored basis, usually sucrose and acacia or tragacanth; pastilles comprising the active ingredient in an inert basis such as gelatin and glycerin, or sucrose and acacia; mouthwashes comprising the active ingredient in a suitable liquid carrier; orally disintegrating tablets which may, for example, disintegrate in less than 90 seconds upon placement in the mouth; and thin films. Such disintegration can be measured by an in vitro dissolution test. Formulations for buccal administration can include, e.g., buccal tablets, bioadhesive particles, wafers, lozenges, medicated chewing gums, adhesive gels, patches, films, which may be delivered as an aqueous solution, a paste, an ointment, or aerosol, to name a few. Formulations for rectal administration may be presented as a suppository with a suitable base comprising for example cocoa butter or a salicylate. Formulations suitable for intrapulmonary or nasal administration can have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of cancerous infections as described below. A pharmacological formulation of the present application can be administered to the patient in an injectable formulation containing any compatible carrier, such as various vehicle, adjuvants, additives, and diluents; or the metopimazine mesylate utilized in the present application can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present application include: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

Preparations for such pharmaceutical compositions are described in, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins., 2000; Martindale, The Extra Pharmacopoeia, Thirty-Second Edition (The Pharmaceutical Press, London, 1999); all of which are incorporated by reference herein in their entirety.

Exemplary Modes of Administration

Administration of a pharmaceutical composition as described herein can be performed by any method that enables delivery of the crystalline form of metopimazine mesylate (e.g., metopimazine mesylate Crystal Form A or metopimazine mesylate Crystal Form B) to the site of action. The composition may be administered orally, parenterally, enterally, intraperitoneally, topically, transdermally, ophthalmically, intranasally, locally, non-orally, via spray, subcutaneously, intravenously, intratonsillary, intramuscularly, buccally, sublingually, rectally, intra-arterially, by infusion, or intrathecally. In some embodiments, the composition is administered orally. In some cases, the oral administration may comprise administration of any of the oral dosage forms as described herein. The effective amount of a crystalline form of metopimazine mesylate (e.g., metopimazine mesylate Crystal Form A or metopimazine mesylate Crystal Form B) administered will be dependent on the subject being treated, the severity of the disorder or condition, the rate of administration, the disposition of the crystalline form of metopimazine mesylate (e.g., metopimazine mesylate Crystal Form A or metopimazine mesylate Crystal Form B) and the discretion of the prescribing physician.

A subject can be administered a daily dosage of a crystalline form of metopimazine mesylate (e.g., metopimazine mesylate Crystal Form A or metopimazine mesylate Crystal Form B) as described herein for the treatment of an enteric nervous system disorder. The daily dosage can be from about 0.01 mg/kg to about 500 mg/kg of body weight per day.

In some embodiments, administration may comprise infusion. In some cases, infusion may involve chronic, steady dosing. Devices for chronic, steady dosing, e.g., by a controlled pump, are known in the art, (examples may be described in U.S. Pat. Nos. 7,341,577, 7,351,239, 8,058,251, herein incorporated by reference).

Administration of the crystalline form of metopimazine mesylate (e.g., metopimazine mesylate Crystal Form A or metopimazine mesylate Crystal Form B) may continue as long as necessary. In some embodiments, the crystalline form of metopimazine mesylate (e.g., metopimazine mesylate Crystal Form A or metopimazine mesylate Crystal Form B) is administered for more than 1, 2, 3, 4, 5, 6, 7, 14, or 28 days. In particular embodiments, the crystalline form of metopimazine mesylate (e.g., metopimazine mesylate Crystal Form A or metopimazine mesylate Crystal Form B) is administered for more than 5 days. In some embodiments, the crystalline form of metopimazine mesylate (e.g., metopimazine mesylate Crystal Form A or metopimazine mesylate Crystal Form B) is administered for more than 12 weeks. In some embodiments, the crystalline form of metopimazine mesylate (e.g., metopimazine mesylate Crystal Form A or metopimazine mesylate Crystal Form B) is administered for more than 1 month, more than 2 months, more than 4 months, more than 6 months, more than 1 year, more than 2 years, or more than 5 years. In some embodiments, the crystalline form of metopimazine mesylate (e.g., metopimazine mesylate Crystal Form A or metopimazine mesylate Crystal Form B) is administered for less than five days.

Exemplary Combination Therapies

In some embodiments, the method comprises co-administration of an additional agent. Additional agents may be: small molecules, nutraceuticals, vitamins, e.g., vitamin D, drugs, pro-drugs, biologics, peptides, peptide mimetics, antibodies, antibody fragments, cell or tissue transplants, vaccines, polynucleotides, DNA molecules, RNA molecules, (i.e.-siRNA, miRNA), antibodies conjugated to drugs, toxins, fusion proteins. Agents may be delivered by vectors, including but not limited to: plasmid vectors, viral vectors, non-viral vectors, liposomal formulations, nanoparticle formulations, toxins, therapeutic radioisotopes, etc.

In some embodiments, a method of the application comprises co-administration of a peripherally restricted dopamine decarboxylase inhibitor and a pharmaceutical composition as described herein. For example, an application method may comprise co-administration of carbidopa and a pharmaceutical composition as described herein.

The additional agent can be an agent for use in the treatment of an enteric nervous system disorder. In some embodiments, the additional agent is an additional anti-emetic agent (e.g., used for the treatment of nausea and/or vomiting). The additional anti-emetic agent can be, by way of non-limiting example only, a 5-HT3 receptor antagonist, a dopamine receptor antagonist, an NK1 receptor antagonist, an antihistamine, a cannabinoid, a benzodiazepine, an anticholinergic agent, a steroid, or other anti-emetic. Exemplary 5-HT3 receptor antagonists include, but are not limited to, Odansetron, Tropisetron, Granisetron, Palonosetron, Dolasetron. Exemplary dopamine receptor antagonists include, e.g., Metoclopramide (Reglan), Domperidone (Motilium), Olanzapine (Zyprexa) Droperidol, haloperidol, chlorpromazine, promethazine, prochlorperazine, Alizapride, Prochlorperazine, Sulpiride. Exemplary NK1 receptor antagonists include, e.g., Aprepitant, Tradipitant or Casopitant. Exemplary antihistamines include, e.g., Cyclizine, Diphenhydramine (Benadryl), Dimenhydrinate (Gravol, Dramamine), Doxylamine, Meclozine (Bonine, Antivert), Promethazine (Pentazine, Phenergan, Promacot), and Hydroxyzine (Vistaril), Cimetidine, Famotidine, Lafutidine, Nizatidine, Ranitidine, Roxatidine, Tiotidine. Exemplary cannabinoids include, e.g., Cannabis, Sativex, tetrahydrocannabinol, Dronabinol, and synthetic cannabinoids such as Nabilone. Exemplary benzodiazepines include, e.g., midazolam or lorazepam. Exemplary anticholinergic agents include, e.g., scopolamine. Other exemplary anti-emetics include, e.g., Trimethobenzamide, Ginger, Emetrol, Propofol, Peppermint, erythromycin, Muscimol, botulinum toxin A (e.g., injected into the stomach to relax the pyloric muscle), and Ajwain.

The additional agent can be an agent for treatment of another disease or clinical syndrome associated with gastroparesis. Exemplary other diseases and clinical syndromes are described herein. The additional agent can be an agent for treatment of diabetes. Exemplary agents for the treatment of diabetes include, e.g., insulin. Other agents for the treatment of diabetes are described in, for example, U.S. Pat. Nos. 6,274,549, 8,349,818, 6,184,209, US Patent Application Publication No. US20070129307, and PCT Application Publication No. WO/2004/082667A1, all of which are hereby incorporated by reference.

The additional agent can be for treatment of upper and lower dysmotility disorders associated with Parkinson's disease. The additional agent can be for treatment of Parkinson's disease. Exemplary agents for the treatment of Parkinson's disease include, e.g., dopaminergic agents, MAO-A or B inhibitors such as, e.g., selegiline, COMT inhibitors such as entacapone, amantadine, stem cell transplant, and neuroprotective agents. Exemplary dopaminergic agents include, but are not limited to levodopa, bromocriptine, pergolide, pramipexole, cabergoline, ropinorole, apomorphine or a combination thereof.

The additional agent can be for treatment of hypothyroidism, hyperthyroidism, or hyperparathyroidism. Exemplary agents for the treatment of such diseases include, e.g., beta-adrenergic blockers ("beta blockers"), levothyroxine calcimimetics, estrogen, progesterone, bisphosphonates.

The additional agent can be for treatment of adrenal insufficiency. Exemplary agents for treatment of adrenal insufficiency include, e.g., corticosteroid hormones (for example, aldosterone, fludrocortisones, and cortisol).

The additional agent can be for treatment of gastroesophageal reflux. Exemplary agents for treatment of gastroesophageal reflux include, e.g., antacids such as, for example, proton pump inhibitors such as omeprazole, H2 receptor antagonists such as ranitidine, antacids, mosapride, sucralfate, and baclofen.

The additional agent can be for treatment of scleroderma. For example, the additional agent can be D-penicillamine, colchicine, PUVA, relaxin, cyclosporine, and EPA (omega-3 oil derivative), immunosupressants such as, e.g., methotrexate, cyclophosphamide, azathioprine, and mycophenolate. The additional agent can be for treatment of polymyositis. For example, the additional agent can be a corticosteroid, e.g., prednisone, or can be an immunosuppressant.

The additional agent can be for treatment of muscular dystrophy. For example, the additional agent can be, e.g., a glucocorticoid receptor antagonist. Exemplary glucocorticoid receptor antagonists include, but are not limited to, mifepristone, 11β-(4-dimethylaminoethoxyphenyl)-17α-propynyl-17β-hydroxy-4,9 estradien-3-one, 17β-hydroxy-17α-19-(4-methylphenyl)androsta-4,9(11)-dien-3-one, 4α(S)-Benzyl-2(R)-prop-1-ynyl-1,2,3,4,4α,9,10,10α(R)-octahydro-phenanthrene-2,7-diol and 4α(S)-Benzyl-2(R)-chloroethynyl-1,2,3,4,4α,9,10,10α(R)-octahydro-phenanthrene-2,7-diol, and (11β,17β)-11-(1,3-benzodioxo-5-yl)-17-hydroxy-17-(1-propynyl)estra-4,9-dien-3-one.

The additional agent can be for treatment of amyloidosis. For example, the additional agent can be an amyloid beta sheet mimic, an antioxidant, molecular chaperone, or other agent. Exemplary agents for the treatment of amyloidosis are described in, e.g., WO/2008/141074. Exemplary molecular chaperones include, e.g., HSP60, HSP70, HSP90, HSP100, BiP, GRP94, GRP170, calnexin and calreticulin, Protein disulfide isomerase (PDI), Peptidyl prolyl cis-transisomerase (PPI), trimethylamine N-oxide (TMAO), betaine, glycine betaine, glycero-phosphorylcholine, carbohydrates such as, e.g., glycerol, sorbitol, arabitol, myo-inositol and trehalose, choline, 4-Phenyl butyric acid, and taurine-conjugated ursodeoxycholic acid.

The additional agent can be for treatment of chronic idiopathic pseudoobstruction. For example, the additional agent can be Prucalopride, Pyridostigmine, Metoclopramide, cisapride, linaclotide, octreotide, cannabinoids, and erythromycin.

The additional agent can be for treatment of dermatomyositis. For example, the additional agent can be Prednisolone, Methotrexate, Mycophenolate (CellCept/Myfortic), intravenous immunoglobulins, Azathioprine (Imuran), Cyclophosphamide, Rituximab, and Acthar Gel.

The additional agent can be for treatment of systemic lupus erytematosus. For example, the additional agent can be renal transplant, corticosteroids, immunosupressants, Hydroxychloroquine, Cyclophosphamide, Mycophenolic acid, immunosupressants, analgesics, intravenous immunoglobins, and the like.

The additional agent can be for treatment of anorexia and/or bulimia. For example, the additional agent can be olanzapine, a tricyclic antidepressant, an MAO inhibitor, mianserin, a selective serotonin reuptake inhibitor, e.g., fluoxetine, lithium carbonate, trazodone, and bupropion, phenytoin, carbamazepine, and valproic acid, opiate antagonists such as, e.g., naloxone and naltrexone, and topiramate.

The additional agent can be for treatment of depression. For example, the additional agent can be a selective serotonin reuptake inhibitor, a serotonin and norepinephrine reuptake inhibitor, bupropion, a tricyclic antidepressant, a monoamine oxidase inhibitor, and the like. The additional agent can be for treatment of paraneoplastic syndrome. The additional agent can be for treatment of a high cervical cord lesion. For example, the additional agent can be a corticosteroid or other anti-inflammatory medication. The additional agent can be for treatment of multiple sclerosis. For example, the additional agent can be interferon beta-lb, interferon beta-la, Glatiramer acetate, Mitoxantrone, natalizumab, fingolimod, teriflunomide, or cladribine.

The additional therapeutic agent can be selected from the group consisting of serotonin agonists, serotonin antagonists, selective serotonin reuptake inhibitors, anticonvulsants, opioid receptor agonists, bradykinin receptor antagonists, NK receptor antagonists, adrenergic receptor agonists, benzodiazepines, gonadotropin-releasing hormone analogues, calcium channel blockers, and somatostatin analogs.

Dosages of the additional agent and of a pharmaceutical composition as described herein for use in the treatment of an enteric nervous system disorder can vary depending on the type of additional therapeutic agent employed, on the disease or condition being treated and so forth. Sub-therapeutic amounts of one or both of the additional agent and the pharmaceutical composition as described herein can be used. The sub-therapeutic amount of one or both of the additional agent and the pharmaceutical composition as described herein can be a synergistically effective amount. Therapeutically effective amounts of one or both of the additional agent and the pharmaceutical composition as described herein can be used. The pharmaceutical composition as described herein and the additional agent may be administered either simultaneously or sequentially. If administered sequentially, the attending physician or caretaker can decide on the appropriate sequence of administering the pharmaceutical composition as described herein and the additional therapeutic agent.

In some embodiments, a method comprising administering any of the pharmaceutical compositions described herein further comprises combination therapy with an additional therapeutic regimen. The additional therapeutic regimen can comprise implantation of a medical device. The medical device can be implanted in the stomach and/or abdomen, e.g., in the duodenum. The medical device can be an electrical device. The medical device can be a pacemaker. Such a pacemaker can utilize electrical current to induce stomach and/or duodenal contractions, thereby promoting gastrointestinal motility. Such medical devices, and methods of using them, are disclosed in U.S. Pat. No. 8,095,218, hereby incorporated by reference.

Embodiments of the application are further described in detail by reference to the following examples. These examples are provided for the purpose of illustration only, and are not intended to be limiting unless otherwise specified. Thus, the application should in no way be construed as being limited to the following examples, but rather, should be construed to encompass any and all variations which become evident as a result of the teaching provided herein.

EXAMPLES

The following examples are offered to illustrate but not to limit the application.

Example 1: Synthesis of Metopimazine Mesylate Crystal Form A

One of skill in the art will recognize that the following synthetic reactions and schemes may be modified by choice of suitable conditions and reagents in order to access metopimazine mesylate, 1-(3-(2-(methylsulfonyl)-10H-phenothiazin-10-yl)propyl)piperidine-4-carboxamide methanesulfonic acid, from metopimazine, 1-(3-(2-(methylsulfonyl)-10H-phenothiazin-10-yl)propyl)piperidine-4-carboxamide. Metopimazine, and methods of making metopimazine, are described in DE1092476, hereby incorporated by reference. Metopimazine can be obtained from a variety of commercial sources (CAS registry number 001400844-7). By way of example only, metopimazine can be obtained from ABI Chemicals (# AC2A0SHFH), AKos (# AKOS005065914), Biochempartner (# BCP9000716) Molport (# MolPort-003-808-703), Santa Cruz Biotechnology (# sc-211901), and Tractus Company Limited (# TX-013443).

Scheme 1: Preparation of Metopimazine Mesylate Crystal Form A from Metopimazine

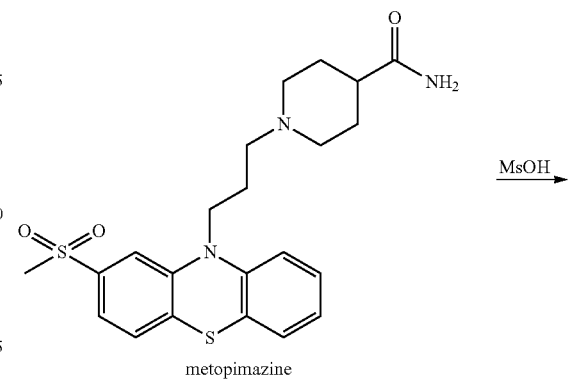

metopimazine

-continued

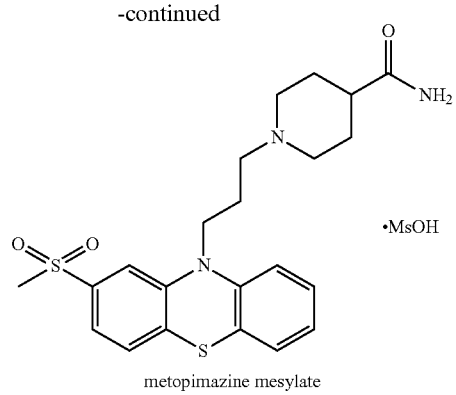

metopimazine mesylate

To metopimazine (50 g) was added dimethyl sulfoxide (DMSO) (150 mL) followed by methanesulfonic acid (MsOH) (11.3 g) over 10 min at 20-25° C. to give a clear solution. Acetone (50 mL) was then added and the solution was filtered over a filter paper. The filtrate was warmed to 68° C. and charged with acetone (175 mL) over 15 min at 68° C. The solution was then cooled to 60° C. over 30 minutes and then agitated at 60° C. for one hour at which time the solution became cloudy. The slurry was cooled to 0° C. over 1.5 hours and then agitated at 0° C. for 1 hour. The solid was collected by filtration and the filter cake reslurried with acetone (200 mL) for 30 minutes. The solid was collected by filtration and the remaining filter cake again reslurried with acetone (200 mL) for 30 minutes. The solid was again collected by filtration. The filter cake was dried under vacuum at 50° C. for 6 hours to afford a yellow solid, metopimazine mesylate Crystal Form A, 40 g, 66% yield.

Similarly, a large scale preparation was performed as follows. To metopimazine (1500 g) was added DMSO (4.5 L) followed by MsOH (341 g) over 30 min at 20-25° C. to give a clear solution. Acetone (1.5 L) was then added and the solution was filtered over a filter paper. The filtrate was warmed to 68° C. and charged with acetone (5.25 L) over 30 min at 68° C. Seed crystals (15 g) were added to the solution. The cloudy solution was then agitated at 68° C. for one hour. The slurry was cooled to 0° C. over 6 hours and the mixture agitated at 0° C. for 14 hour. The solid was collected by filtration and the filter cake washed with acetone (4.5 L). The filter cake was agitated with acetone (6 L) for 30 minutes. The solid was collected by filtration, and the filter cake was agitated with acetone (6 L) for 30 minutes. The solid was collected by filtration. The filter cake was dried under vacuum at 50° C. for 7 hours to afford a yellow solid, metopimazine mesylate Crystal Form A, 1558 g, 85% yield.

The structure of metopimazine mesylate was confirmed by high resolution mass spectrometry ([M+H]+=446.16), $^1$H NMR (Table 3), and $^{13}$C NMR (Table 4).

TABLE 3

$^1$H NMR of Metopimazine Mesylate; 400 MHz $^1$HNMR; DMSO-d6

| Chemical Shift (ppm) | Integration | Multiplicity | Coupling Constant (J, Hz) |
|---|---|---|---|
| 9.15 | 1H | s | — |
| 6.91-7.48 | 9H | m | — |
| 4.06 | 2H | t | 6.6 |
| 3.46 | 2H | d | 11.2 |
| 3.41 | 3H | s | — |
| 3.17 | 2H | m | — |
| 2.88 | 2H | dd | 22.8, 11.2 |
| 2.37 | 4H | m | — |
| 2.08 | 2H | m | — |
| 1.90 | 2H | m | — |
| 1.72 | 2H | dd | 24.4, 12.0 |

TABLE 4

$^{13}$C NMR of Metopimazine Mesylate; 400 MHz $^{13}$CNMR; DMSO-d6

| Chemical Shift | Multiplicity |
|---|---|
| 174.80 | s |
| 145.41 | s |
| 143.38 | s |
| 140.28 | s |
| 131.31 | s |
| 128.26 | s |
| 127.85 | s |
| 127.56 | s |
| 123.68 | s |
| 122.99 | s |
| 121.12 | s |
| 116.74 | s |
| 113.59 | s |
| 53.80 | s |
| 51.41 | s |
| 43.93 | s |
| 43.49 | s |
| 38.53 | s |
| 25.86 | s |
| 21.26 | s |

The structure of the single crystal was determined successfully. The crystal system was Monoclinic, the space group was Pn. The unit cell dimensions of the structure were as follows: a=11.90502(6) Å, b=5.57773(3) Å, c=19.47543(12) Å, α=90°, β=103.5908(6°), γ=90°, V=1257.014(13) Å3. The asymmetric unit was found to contain one Metopimazine cation and one Mesylate anion, which indicated Form A is an anhydrate. The final refinement parameters are listed below in Table 5.

TABLE 5

Crystallographic data and refinement parameters

| | |
|---|---|
| Identification code | 818114-01-A |
| Empirical formula | $C_{23}H_{31}N_3O_6S_3$ |
| Formula weight | 541.69 |
| Temperature | 100.01(10) K |
| Wavelength | CuKα (λ = 1.54184 Å) |
| Crystal system, space group | Monoclinic, Pn |
| Unit cell dimensions | a = 11.90502(6) Å |
| | b = 5.57773(3) Å |
| | c = 19.47543(12) Å |
| | α = 90° |
| | β = 103.5908(6)° |
| | γ = 90° |
| Volume | 1257.014(13) Å$^3$ |
| Z, Calculated density | 2, 1.431 g/cm$^3$ |
| Absorption coefficient | 3.077 mm$^{-1}$ |
| F(000) | 572.0 |
| Crystal size | 0.12 × 0.08 × 0.05 mm$^3$ |
| 2 Theta range for data collection | 7.964 to 149.606 |

TABLE 5-continued

Crystallographic data and refinement parameters

| | |
|---|---|
| Limiting indices | $-14 \leq h \leq 14$ |
| | $-6 \leq k \leq 5$ |
| | $-24 \leq l \leq 23$ |
| Reflections collected/ | 41976/4970 [$R_{int}$ = 0.0425, |
| Independent reflections | $R_{sigma}$ = 0.0215] |
| Refinement method | Full-matrix least-squares on $F^2$ |
| Data/restraints/parameters | 4970/2/330 |
| Goodness-of-fit on $F^2$ | 1.046 |
| Final R indices [I ≥ 2sigma(I)] | $R_1$ = 0.0225, $wR_2$ = 0.0557 |
| Final R indices [all data] | $R_1$ = 0.0230, $wR_2$ = 0.0561 |
| Largest diff. peak and hole | 0.17/-0.31 e.Å$^{-3}$ |

The peak list of the calculated XRPD of the single crystal for Metopimazine Mesylate Crystal Form A is provided in Table 6.

TABLE 6

Peak List of the Calculated XRPD of the Single Crystal

| Pos. [°2 Th.] | Height [cts] |
|---|---|
| 7.957 | 82.639 |
| 9.336 | 2364.303 |
| 9.841 | 143.466 |
| 14.310 | 238.385 |
| 15.301 | 4263.465 |
| 15.953 | 6407.846 |
| 16.555 | 1744.832 |
| 17.505 | 1459.676 |
| 17.781 | 4685.051 |
| 18.451 | 865.592 |
| 18.727 | 4592.584 |
| 19.119 | 6048.643 |
| 19.759 | 691.551 |
| 20.827 | 4974.073 |
| 21.251 | 7494.354 |
| 21.433 | 4760.087 |
| 21.845 | 4066.813 |
| 22.129 | 340.111 |
| 22.579 | 215.487 |
| 23.364 | 493.197 |
| 23.718 | 472.990 |
| 24.028 | 2541.677 |
| 24.469 | 10199.890 |
| 24.637 | 3353.198 |
| 25.447 | 680.649 |
| 26.412 | 1432.003 |
| 26.645 | 695.484 |
| 26.975 | 274.768 |
| 27.574 | 219.672 |
| 28.004 | 986.973 |
| 28.208 | 1092.305 |
| 28.467 | 377.833 |
| 28.902 | 450.327 |
| 29.408 | 292.149 |
| 29.648 | 385.100 |
| 29.823 | 152.139 |
| 30.079 | 108.698 |
| 30.723 | 885.873 |
| 30.887 | 972.559 |
| 31.403 | 403.286 |
| 31.892 | 742.574 |
| 32.130 | 481.241 |
| 32.422 | 283.382 |
| 32.575 | 162.015 |
| 33.107 | 579.165 |
| 33.470 | 655.390 |
| 33.617 | 368.145 |
| 33.864 | 416.154 |
| 34.203 | 679.729 |
| 34.451 | 214.356 |
| 34.883 | 276.078 |
| 35.141 | 264.082 |
| 35.270 | 273.631 |

TABLE 6-continued

Peak List of the Calculated XRPD of the Single Crystal

| Pos. [°2 Th.] | Height [cts] |
|---|---|
| 35.759 | 193.775 |
| 36.027 | 936.252 |
| 36.528 | 111.915 |
| 36.896 | 648.189 |
| 37.494 | 276.960 |
| 37.994 | 541.559 |
| 38.137 | 408.057 |
| 38.798 | 73.631 |
| 39.461 | 393.184 |
| 39.779 | 580.681 |
| / | / |

For XRPD analysis, PANalytical X-ray powder diffract meters were used. Samples were prepared by putting a layer of sample (approx. 5 mg) on the center of a silicon wafer. The XRPD parameters used are listed in Table 7. The XRPD pattern is provide in FIG. 1, and the peaks provided in Table 1 above.

TABLE 7

Parameters for XRPD test

| Parameters | X' Pert3 |
|---|---|
| Mode | Reflection mode |
| X-Ray wavelength | Cu*, Kα, |
| | Kα1 (Å): 1.540598, |
| | Kα2 (Å): 1.544426 |
| | Kα2/Kα1 intensity ratio: 0.50 |
| X-Ray tube setting | 45 kV, 40 mA |
| Divergence slit | 1/8° |
| Scan mode | Continuous |
| Scan range (2Θ/°) | 3°-40° |
| Step size (2Θ/°) | 46.7 |
| Scan step time (s) | 0.0263 |
| Test Time (s) | 5 min 04s |

*Filter: Beta-filter nickel

TGA data were collected using a TA Q5500 TGA from TA Instruments and DSC was performed using a TA Q2500 DSC from TA Instruments. Detailed parameters used are listed in Table 8. Sample was prepared by adding sample (approximately 2 mg) in the pan. The TGA plot is provided in FIG. 2. Metopimazine mesylate Crystal Form A exhibited minimal weight loss by TGA (0.4% up to 150.0° C.). The DSC plot is provided in FIG. 3. Metopimazine mesylate Crystal Form A exhibited a clear melt with onset at 209.9° C. (melt=213.1° C.; enthalpy=97.47 J/g).

TABLE 8

Parameters for TGA and DSC test

| Parameters | TGA | DSC |
|---|---|---|
| Method | Ramp | Ramp |
| Sample pan | Aluminum, open | Aluminum, crimped |
| Temperature | RT-350° C. | RT-300° C. |
| Heating rate | 10° C./min | 10° C./min |
| Purge gas | $N_2$ | $N_2$ |

Example 2: Synthesis of Metopimazine Mesylate Crystal Form B

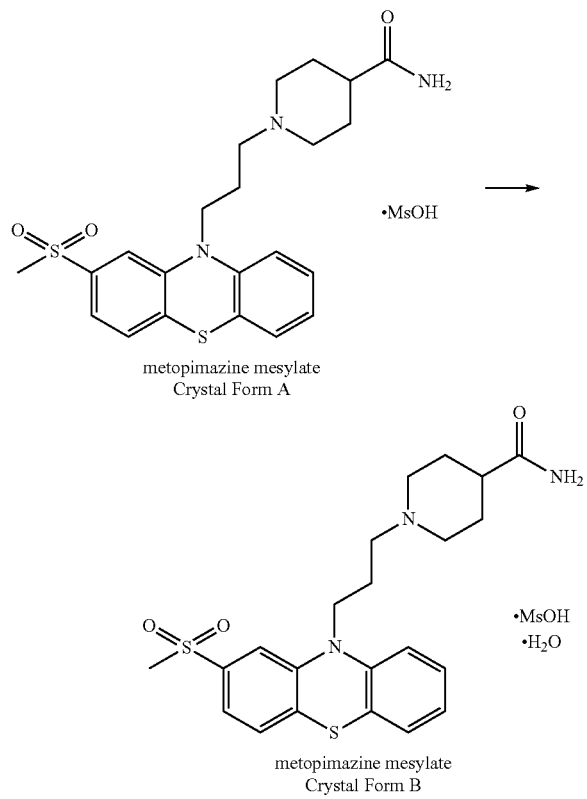

Scheme 2: Preparation of Metopimazine Mesylate Crystal Form B from Metopimazine Mesylate Crystal Form A A glass beaker containing a thin layer of metopimazine mesylate Crystal Form A (10 g) was allowed to sit at room temperature and 100% relative humidity for approximately 3-5 days to provide metopimazine mesylate Crystal Form B as an off-white solid. The structure of metopimazine mesylate Crystal Form B was confirmed by $^1$H NMR (Table 9).

TABLE 9

$^1$H NMR of Metopimazine Mesylate Crystal Form B; 400 MHz $^1$HNMR; DMSO-d6

| Chemical Shift (ppm) | Integration | Multiplicity | Coupling Constant (J, Hz) |
|---|---|---|---|
| 8.96 | 1H | s | — |
| 6.91-7.52 | 9H | m | — |
| 4.06 | 2H | t | 6.7 |
| 3.46 | 2H | d | 11.4 |
| 3.24 | 3H | s | — |
| 3.15 | 2H | m | — |
| 2.89 | 2H | dd | 10.6, 22.9 |
| 2.33 | 4H | m | — |
| 2.09 | 2H | m | — |
| 1.89 | 2H | m | — |
| 1.69 | 2H | dd | 14.6, 27.4 |

Figure 4:
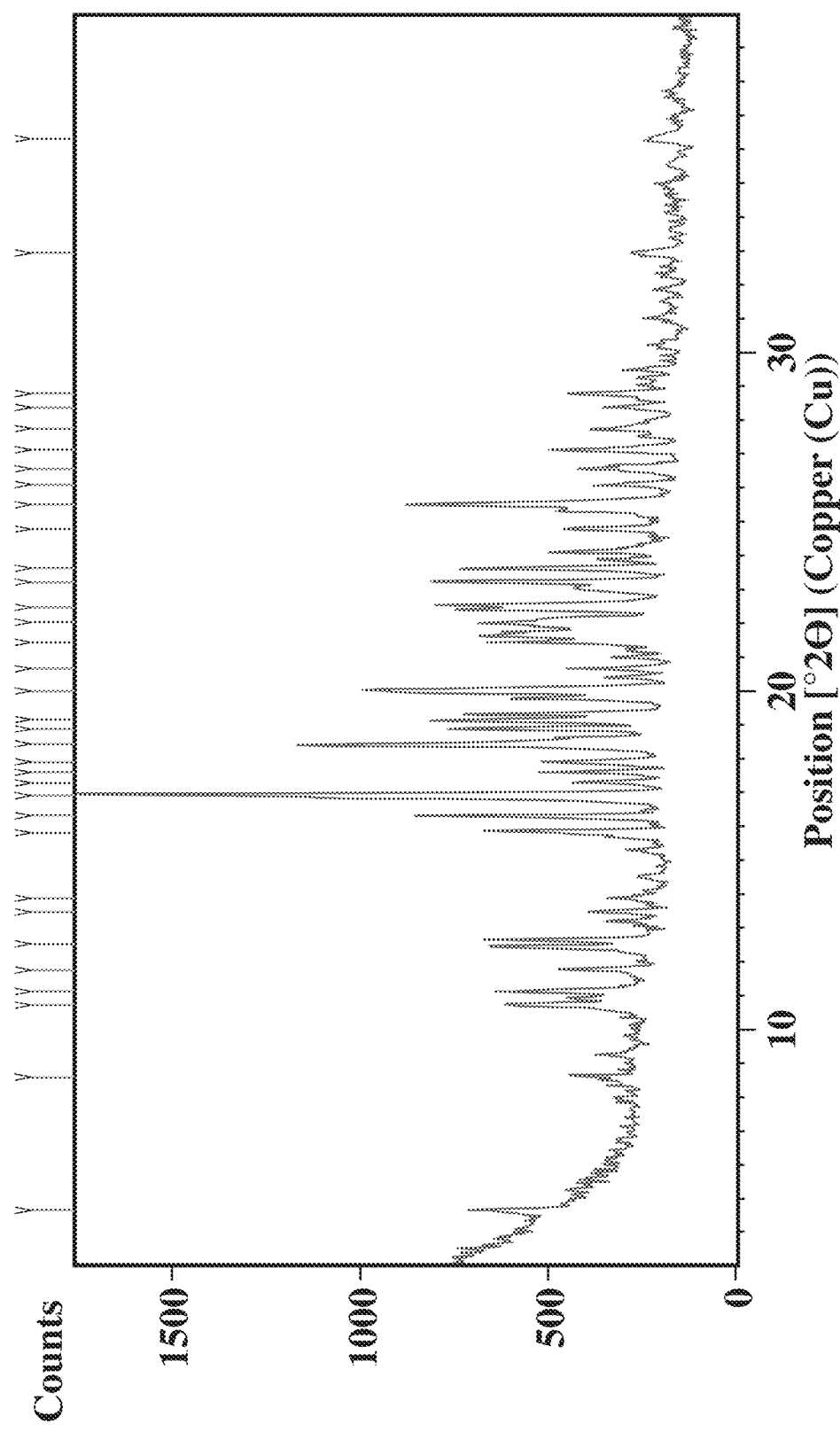
FIG. 4 depicts the X-ray powder diffractogram (XRPD) of metopimazine mesylate Crystal Form B.

For XRPD analysis, PANalytical X-ray powder diffract meters were used. Sample was prepared by putting a layer of sample (approx. 5 mg) on the center of a silicon wafer. The XRPD parameters used are listed in Table 6 above. The XRPD pattern is provide in FIG. 4, and the peaks provided in Table 2 above.

TGA data were collected using a TA Q5500 TGA from TA Instruments and DSC was performed using a TG Q2000 DSC from TA Instruments. Detailed parameters used are listed in Table 7 above. Sample was prepared by adding sample (approximately 2 mg) in the pan. The TGA/DSC plot is provided in FIG. 5. A weight loss of 5.8% was observed up to 180° C., and two endothermic peaks at 123.5 and 208.6° C. (onset temperature) (melt=126.1° C. and 211.2° C., respectively; enthalpy=83.47 J/g and 84.48 J/g, respectively) and one exothermic peak at 144.6° C. (peak temperature) were observed.

Example 3: Pharmacokinetic Analysis of Metopimazine Mesylate Crystal Form A

A clinical comparative pharmacokinetic study was performed to understand the pharmacokinetic profile of metopimazine mesylate Crystal Form A in comparison to the free base of metopimazine. This study was as a 3-period, crossover design with 3 administrations of single doses: oral formulation of metopimazine mesylate Crystal Form A fasting, oral formulation of metopimazine mesylate Crystal Form A after a high-fat breakfast, and oral formulation of metopimazine free base fasting, with a wash-out period of 48 hours between each administration. Fifteen subjects were enrolled and received each of the 3 treatment. Plasma samples from each subject were analyzed for various pharmacokinetic parameters. Mixed model repeated measures (MMRM) analysis was performed on each sample. The comparison of metopimazine mesylate Form A and metopimazine free base showed that $T_{max}$ values for metopimazine mesylate Form A had a statistically significantly lower variance than metopimazine free base. The results are shown in Table 10 below.

TABLE 10

$T_{max}$ Analysis

| Treatment | Parameter | $T_{max}$ (h) |
|---|---|---|
| Metopimazine free base, 15 mg, n =15; fasted | Mean | 1.27 |
| | SD | 0.98 |
| | CV % | 77.33 |
| | Min | 0.50 |
| | Median | 1.00 |
| | Max | 4.00 |
| Metopimazine mesylate Crystal Form A, 15 mg, n = 15; fasted | Mean | 0.87 |
| | SD | 0.30***[1] |
| | CV % | 34.25 |
| | Min | 0.50 |
| | Median | 0.75 |
| | Max | 1.50 |

***[1]p < 0.0001

The above results demonstrate that metopimazine mesylate Crystal Form A provides a more predictable onset of action as compared to metopimazine free base. The lower variance in $T_{max}$ for metopimazine mesylate Crystal Form A provides an important benefit to the population of subjects suffering from gastroparesis as that population requires a treatment that can be taken before meal time so as to reduce the symptoms that invariably are worsened by eating.

The second objective of this study was to compare the pharmacokinetics of metopimazine mesylate Crystal Form A administered as an oral administration of a single dose of 15 mg orally in 15 human subjects either in a fasted state or after a high fat breakfast. Plasma samples from each subject were analyzed for various pharmacokinetic parameters. The geometric mean difference in $C_{max}$ was slightly but significantly lower, whereas there was not statistical difference in the geometric mean AUC. Both $C_{max}$ and AUC are well within the 90% confidence interval. The results are shown in Table 11 below.

A minor reduction in $C_{max}$ of approximately 15% was seen when metopimazine mesylate Crystal Form A was administered with food, but there was no notable change in AUC (well within the 90% upper and lower intervals which define bioequivalence). This slight difference in $C_{max}$ is not of clinical significance (FDA Guidance for the industry: Food-Effect Bioavailability and Fed Bioequivalence Studies). These results are in contrast with previously published data indicating a food effect for metopimazine free base which resulted in a 58% reduction in $C_{max}$ and a 23% reduction in AUC following administration of metopimazine free base before and after a high fat breakfast (Herrstedt et al. 1990).

TABLE 11

$C_{max}$ and AUC Analysis

| Treatment | $C_{max}$ Geometric Least Square Mean (GLSM) (ng/mL) | $AUC_{0-inf}$ Geometric Least Square Mean (GLSM) (ng · h/mL) |
| --- | --- | --- |
| Metopimazine Mesylate Crystal Form A 15 mg n = 15; fasted | 18.16 | 63.96 |
| Metopimazine Mesylate Crystal Form A 15 mg n = 15; fed high fat breakfast (1030 kcal, 16% protein, 61% fat, 23% carbohydrate) | 15.26 | 59.89 |
| Ratio fasted vs fed (%) | 84.07 | 93.63 |
| Lower CI % | 63.82 | 86.00* |
| Upper CI % | 110.75 | 101.93* |

*Bioequivalence

The lack of food effect for metopimazine mesylate Crystal Form A provides a benefit to the population of subjects suffering from gastroparesis as that population displays delayed gastric emptying and residual gastric food contents for extended periods of time which could exacerbate the PK variability of a drug sensitive to food such as metopimazine free base.

While preferred embodiments of the present application have been shown and described herein, it will be obvious to those skilled in the art that such embodiments are provided by way of example only. Numerous variations, changes, and substitutions will now occur to those skilled in the art without departing from the application. It should be understood that various alternatives to the embodiments of the application described herein may be employed in practicing the application. It is intended that the following claims define the scope of the application and that methods and structures within the scope of these claims and their equivalents be covered thereby.

INCORPORATION BY REFERENCE

All references cited in this application, and their references, are incorporated by reference herein in their entirety where appropriate for teachings of additional or alternative details, features, and/or technical background.

The invention claimed is:

1. A crystalline form of metopimazine mesylate characterized by an X-ray powder diffraction pattern comprising two or more of the following 2θ values: 9.37°, 9.87°, 14.33°, 15.26°, 15.91°, 16.55°, 17.52°, 17.75°, 18.75°, 19.09°, 19.72°, 20.80°, 21.22°, 21.77°, 23.29°, 23.91°, 24.44°, 25.37°, 26.39°, 26.92°, 27.96°, 28.23°, 28.78°, 29.27°, 29.64°, 30.67°, 31.29°, 31.84°, 32.09°, 32.99°, 33.40°, 33.99°, 35.91°, 36.80°, 37.41°, 37.92°, and 39.27°.

2. The crystalline form of claim 1, characterized by an X-ray powder diffraction pattern comprising two or more of the following 2θ values: 9.37°, 15.26°, 15.91°, 18.75°, 19.09°, 20.80°, 21.22°, 21.77°, and 24.44°.

3. The crystalline form of claim 2, characterized by an X-ray powder diffraction pattern comprising three or more of the following 2θ values: 9.37°, 15.26°, 15.91°, 18.75°, 19.09°, 20.80°, 21.22°, 21.77°, and 24.44°.

4. The crystalline form of claim 1, characterized by an X-ray powder diffraction pattern comprising peaks at the following 2θ values: 15.91° and 18.75°.

5. The crystalline form of claim 1, characterized by an X-ray powder diffraction pattern comprising peaks at the following 2θ values: 15.91°, 18.75°, and 24.44°.

6. A crystalline form of metopimazine mesylate characterized by a differential scanning calorimetry pattern comprising a single endotherm comprising an onset temperature range of 208° C. to 212° C.

7. The crystalline form of claim 6, wherein the single endotherm comprises an onset temperature range of 208° C. to 211° C.

8. The crystalline form of claim 6, wherein the single endotherm comprises an onset temperature range of 209° C. to 210° C.

9. The crystalline form of claim 6, wherein the single endotherm comprises a peak temperature range of 213° C. to 214° C.

10. The crystalline form of claim 6, wherein the single endotherm comprises an enthalpy of transition of 95-100 J/g.

11. The crystalline form of claim 10, wherein the single endotherm comprises an enthalpy of transition of 96-98 J/g.

12. The crystalline form of claim 10, wherein the single endotherm comprises an enthalpy of transition of 97-98 J/g.

13. A crystalline form of metopimazine mesylate characterized by a thermogravimetric analysis profile comprising a total weight loss of 0.4% up to 150.0° C.

14. A pharmaceutical composition comprising the crystalline form of claim 1 and a pharmaceutically acceptable excipient.

15. The pharmaceutical composition of claim 14, wherein the pharmaceutical composition comprises less than 10 wt. % of other crystalline forms of metopimazine mesylate.

16. The pharmaceutical composition of claim 15, wherein the pharmaceutical composition comprises less than 1 wt. % of other crystalline forms of metopimazine mesylate.

17. The pharmaceutical composition of claim 14, wherein the composition comprises less than 10 wt. % of amorphous forms of metopimazine mesylate.

18. The pharmaceutical composition of claim 17, wherein the composition comprises less than 1 wt. % of amorphous forms of metopimazine mesylate.

19. The pharmaceutical composition of claim 14, wherein the pharmaceutical composition is suitable for administering orally, intraduodenally, intracolonically, enterally, topically, intranasally, non-orally, buccally, sublingually, by inhalation, or rectally.

20. The pharmaceutical composition of claim 19, wherein the composition is suitable for administering orally.

21. The pharmaceutical composition of claim 19, wherein the composition is suitable for administering sublingually.

22. The pharmaceutical composition of claim 14, wherein the pharmaceutical composition is formulated as a tablet, a capsule, a paste, a powder, a suspension, a suppository, an extended-release formulation, or a modified-release formulation.

23. The pharmaceutical composition of claim 22, wherein the composition is formulated as an extended release formulation.

24. The pharmaceutical formulation of claim 22, wherein the composition is formulated as a capsule.

* * * * *